US008324252B2

(12) United States Patent
Davies et al.

(10) Patent No.: US 8,324,252 B2
(45) Date of Patent: Dec. 4, 2012

(54) PYRAZOLYLAMINOPYRIDINE DERIVATIVES USEFUL AS KINASE INHIBITORS

(75) Inventors: Audrey Davies, Waltham, MA (US); Michelle Lamb, Belmont, MA (US); Paul Lyne, Arlington, MA (US); Tao Wang, Sudbury, MA (US); Dingwei Yu, Natick, MA (US); Peter Mohr, Boulder, CO (US); Bin Wang, Longmont, CO (US)

(73) Assignee: Astrazeneca AB, Sodertalje (SE)

( * ) Notice: Subject to any disclaimer, the term of this patent is extended or adjusted under 35 U.S.C. 154(b) by 836 days.

(21) Appl. No.: 11/815,140

(22) PCT Filed: Feb. 1, 2006

(86) PCT No.: PCT/GB2006/000334
§ 371 (c)(1),
(2), (4) Date: Jan. 10, 2008

(87) PCT Pub. No.: WO2006/082392
PCT Pub. Date: Aug. 10, 2006

(65) Prior Publication Data
US 2008/0139561 A1    Jun. 12, 2008

Related U.S. Application Data

(60) Provisional application No. 60/650,053, filed on Feb. 4, 2005, provisional application No. 60/653,329, filed on Feb. 16, 2005, provisional application No. 60/721,633, filed on Sep. 29, 2005.

(51) Int. Cl.
*A61K 31/44*    (2006.01)
*C07D 401/14*   (2006.01)

(52) U.S. Cl. ...................................... 514/333; 546/256

(58) Field of Classification Search .................. 546/256; 514/333
See application file for complete search history.

(56) References Cited

U.S. PATENT DOCUMENTS

| | | | |
|---|---|---|---|
| 2005/0054638 A1* | 3/2005 | Barlaam et al. ............ 514/227.8 |
| 2007/0142413 A1 | 6/2007 | Block et al. | |
| 2008/0004302 A1 | 1/2008 | Theoclitou et al. | |
| 2008/0108633 A1 | 5/2008 | Claesson | |
| 2008/0108669 A1 | 5/2008 | Claesson | |
| 2008/0176872 A1 | 7/2008 | Lamb et al. | |
| 2008/0194606 A1 | 8/2008 | Scott et al. | |
| 2008/0287437 A1 | 11/2008 | Wang et al. | |
| 2008/0287475 A1 | 11/2008 | Feng et al. | |
| 2009/0005396 A1 | 1/2009 | Claesson | |

FOREIGN PATENT DOCUMENTS

| | | |
|---|---|---|
| EP | 1876178 A1 | 1/2008 |
| WO | 9941253 A1 | 8/1999 |
| WO | 0063182 A2 | 10/2000 |
| WO | 0117995 A1 | 3/2001 |
| WO | 0147921 A1 | 7/2001 |
| WO | 0160816 A1 | 8/2001 |
| WO | 0185699 A2 | 11/2001 |
| WO | 0218346 A1 | 3/2002 |
| WO | 0222601 A1 | 3/2002 |
| WO | 0222602 A2 | 3/2002 |
| WO | 0222603 A1 | 3/2002 |
| WO | 0222604 A1 | 3/2002 |
| WO | 0222605 A1 | 3/2002 |
| WO | 0222606 A1 | 3/2002 |
| WO | 0222607 A1 | 3/2002 |
| WO | 0222608 A1 | 3/2002 |
| WO | 0250065 A2 | 6/2002 |
| WO | 0250071 A1 | 6/2002 |
| WO | 02064096 A2 | 8/2002 |
| WO | WO 02/066461 | 8/2002 |
| WO | 2004037814 A1 | 5/2004 |
| WO | 2005016893 A2 | 2/2005 |
| WO | 2005103010 A2 | 11/2005 |
| WO | 2006037117 A1 | 4/2006 |
| WO | 2006067614 A2 | 6/2006 |
| WO | 2006074057 A2 | 7/2006 |
| WO | 2006087538 A1 | 6/2007 |
| WO | 2007071348 A1 | 6/2007 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
20050054638, US, Mar. 10, 2005, Feb. 11, 2008 Office Action.
20050054638, US, Mar. 10, 2005, Jun. 20, 2008 Office Action.
20050054638, US, Mar. 10, 2005, Aug. 23, 2007 Office Action.
20050054638, US, Mar. 10, 2005, Oct. 31, 2008 Notice of Allowance.
Kenneth Thress et al, Identification and Preclinical Characterization of AZ-23, a Novel, Selective, and Orally Bioavailable Inhibitor of the Trk Kinase Pathway, 1Division of Pediatrics, University of Texas M. D. Anderson Cancer Center, Houston, Texas.
Tao Wang et al, Identification of 4-Aminopyrazolylpyrimidines as Potent Inhibitors of Trk Kinases, Journal of Medicinal Chemistry, 2008, 4672-4684, 51, 15, ACS Publications, DC, US.
Wang T et al. Trk Kinase Inhibitors as New Treatments for Cancer and Pain, Expert Opinion Therapy, Patents (2009); pp. 305-319, 19(3).
International Search Report for corresponding PCT application No. PCT/GB2006/000334.

* cited by examiner

*Primary Examiner* — Shawquia Young
(74) *Attorney, Agent, or Firm* — Dechert LLP

(57) ABSTRACT

This invention relates to novel compounds having the Formula (I) to their pharmaceutical compositions and to their methods of use. These novel compounds provide a treatment for cancer.

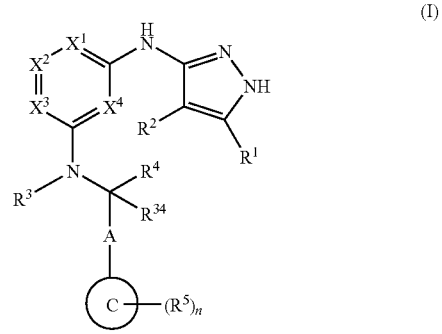

3 Claims, No Drawings

PYRAZOLYLAMINOPYRIDINE DERIVATIVES USEFUL AS KINASE INHIBITORS

CROSS-REFERENCE TO RELATED APPLICATIONS

This application is a U.S. National Stage under 35 U.S.C §371 of International Application No. PCT/GB2006/000334 (filed Feb. 1, 2006) which claims priority under 35 U.S.C. §119(e) to U.S. Provisional Application No. 60/650,053 filed on Feb. 4, 2005; to U.S. Provisional Application No. 60/653,329, filed on Feb. 16, 2005; and to U.S. Provisional Application No. 60/721,633, filed on Sep. 29, 2005.

FIELD OF THE INVENTION

The present invention relates to novel pyrazole derivatives, their pharmaceutical compositions and methods of use. In addition, the present invention relates to therapeutic methods for the treatment and prevention of cancers and to the use of these pyrazole derivatives in the manufacture of medicaments for use in the treatment and prevention of cancers.

BACKGROUND OF THE INVENTION

Receptor tyrosine kinases (RTK's) are a sub-family of protein kinases that play a critical role in cell signalling and are involved in a variety of cancer related processes including cell proliferation, survival, angiogenesis and metastasis. Currently up to 100 different RTK's including tropomyosin-related kinases (Trk's) have been identified.

Trk's are the high affinity receptors activated by a group of soluble growth factors called neurotrophins (NT). The Trk receptor family has three members—TrkA, TrkB and TrkC. Among the NTs there are (i) nerve growth factor (NGF) which activates TrkA, (ii) brain-derived growth factor (BDNF) and NT-4/5 which activate TrkB and (iii) NT3 which activates TrkC. Each Trk receptor contains an extra-cellular domain (ligand binding), a trans-membrane region and an intra-cellular domain (including kinase domain). Upon binding of the ligand, the kinase catalyzes auto-phosphorylation and triggers downstream signal transduction pathways.

Trk's are widely expressed in neuronal tissue during its development where Trk's are critical for the maintenance and survival of these cells. A post-embryonic role for the Trk/neurotrophin axis (or pathway), however, remains in question. There are reports showing that Trk's play important role in both development and function of the nervous system (Patapoutian, A. et al *Current Opinion in Neurobiology*, 2001, 11, 272-280).

In the past decade, a considerable number of literature documentations linking Trk signalling with cancer have published. For example, while Trk's are expressed at low levels outside the nervous system in the adult, Trk expression is increased in late stage prostate cancers. Both normal prostate tissue and androgen-dependent prostate tumours express low levels of Trk A and undetectable levels of Trk B and C. However, all isoforms of Trk receptors as well as their cognate ligands are up-regulated in late stage, androgen-independent prostate cancer. There is additional evidence that these late stage prostate cancer cells become dependent on the Trk/neurotrophin axis for their survival. Therefore, Trk inhibitors may yield a class of apoptosis-inducing agents specific for androgen-independent prostate cancer (Weeraratna, A. T. et al *The Prostate*, 2000, 45, 140-148).

Furthermore, very recent literature also shows that over-expression, activation, amplification and/or mutation of Trk's are associated with secretory breast carcinoma (*Cancer Cell*, 2002, 2, 367-376), colorectal cancer (Bardelli et al *Science*, 2003, 300, 949-949) and ovarian cancer (Davidson, B. et al *Clinical Cancer Research*, 2003, 9, 2248-2259).

There are a few reports of selective Trk tyrosine kinase inhibitors. Cephalon described CEP-751, CEP-701 (George, D. et al *Cancer Research*, 1999, 59, 2395-2341) and other indolocarbazole analogues (WO0114380) as Trk inhibitors. It was shown that CEP-701 and/or CEP751, when combined with surgically or chemically induced androgen ablation, offered better efficacy compared with mono-therapy alone. GlaxoSmithKline disclosed certain oxindole compounds as Trk A inhibitors in WO0220479 and WO0220513. Recently, Japan Tobacco reported pyrazolyl condensed cyclic compounds as Trk inhibitors (JP2003231687A).

In addition to the above, Vertex Pharmaceuticals have described pyrazole compounds as inhibitors of GSK3, Aurora, etc. in WO0250065, WO0262789, WO03027111 and WO200437814; and AstraZeneca have reported pyrazole compounds as inhibitors against IGF-1 receptor kinase (WO03048133).

SUMMARY OF THE INVENTION

In accordance with the present invention, the applicants have hereby discovered novel pyrazole compounds, or pharmaceutically acceptable salts thereof, which possess Trk kinase inhibitory activity and are accordingly useful for their anti-proliferation and/or proapoptotic (such as anti-cancer) activity and in methods of treatment of the human or animal body. The invention also relates to processes for the manufacture of said pyrazole compounds, or pharmaceutically acceptable salts thereof, to pharmaceutical compositions containing them and to their use in the manufacture of medicaments for use in the production of an anti-proliferation and/or proapoptotic effect in warm-blooded animals such as man.

Also in accordance with the present invention the applicants provide methods of using such pyrazole compounds, or pharmaceutically acceptable salts thereof, in the treatment of cancer.

The properties of the compounds claimed in this invention are expected to be of value in the treatment of disease states associated with cell proliferation such as cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

Furthermore, the compounds, or pharmaceutically acceptable salts thereof, of the invention are expected to be of value in the treatment or prophylaxis of cancers selected from congenital fibrosarcoma, mesoblastic nephroma, mesothelioma, acute myeloblastic leukemia, acute lymphocytic leukemia, multiple myeloma, melanoma, oesophageal cancer, myeloma, hepatocellular, pancreatic, cervical cancer, Ewings sarcoma, neuroblastoma, Kaposi sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma, thyroid cancer including papillary thyroid cancer, mesothelioma and leukaemia; particularly ovarian cancer, breast cancer, colorectal cancer, prostate cancer and lung cancer—NSCLC and SCLC; more particularly prostate cancer; and more particularly hormone refractory prostate cancer.

DETAILED DESCRIPTION OF THE INVENTION

Accordingly, the present invention provides a compound of formula (I):

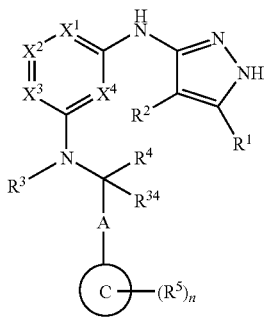

(I)

wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$-amino, $C_{1-6}$alkanoylamino, N—$(C_{1-6}$alkyl)carbamoyl, N,N—$(C_{1-6}$alkyl)$_2$-carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =CR$^8$—, =CR$^9$— and =CR$^{10}$—;

$R^3$ is hydrogen or optionally substituted $C_{1-6}$alkyl; wherein said optional substituents are selected from one or more $R^{11}$;

$R^4$ and $R^{34}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl or heterocyclyl; wherein $R^4$ and $R^{34}$ may be independently optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl-$R^{37}$— or heterocyclyl-$R^{38}$—; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl-$R^{25}$— or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, carbocyclyl-$R^{27}$— or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an —NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl; wherein $R^7$, $R^{13}$, $R^{15}$, $R^{17}$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—$(C_{1-6}$alkyl)amino, N,N—$(C_{1-6}$alkyl)$_2$amino, $C_{1-6}$alkanoylamino, N—$(C_{1-6}$alkyl)carbamoyl, N,N—$(C_{1-6}$alkyl)$_2$carbamoyl, $C_{1-6}$alkylS(O)$_a$ wherein a is 0 to 2, $C_{1-6}$alkoxycarbonyl, N—$(C_{1-6}$alkyl)sulphamoyl, N,N—$(C_{1-6}$alkyl)$_2$sulphamoyl, $C_{1-6}$alkylsulphonylamino, $C_{1-6}$alkylsulphonyl-N—$(C_{1-6}$alkyl)amino, carbocyclyl-$R^{35}$— or heterocyclyl-$R^{36}$—; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$, $R^{28}$, $R^{35}$, $R^{36}$, $R^{37}$ and $R^{38}$ are independently selected from a direct bond, —O—, —N($R^{29}$)—, —C(O)—, —N($R^{30}$)C(O)—, —C(O)N($R^{31}$)—, —S(O)$_s$—, —NH=CH—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl or phenyl; and $R^{24}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

According to a further feature of the present invention there is provided a compound of formula (I) which is a compound of formula (Ia):

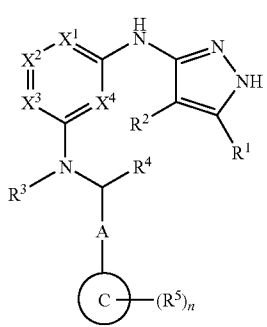

(Ia)

wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =CR$^8$—, =CR$^9$— and =CR$^{10}$—;

$R^3$ is hydrogen or optionally substituted $C_{1-6}$alkyl; wherein said optional substituents are selected from one or more $R^{11}$;

$R^4$ is selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^4$ may be optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{25}$— or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{27}$— or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an —NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^{13}$, $R^{15}$, $R^{17}$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$ and $R^{28}$ are independently selected from a direct bond, —O—, —N($R^{29}$)—, —C(O)—, —N($R^{30}$)C(O)—, —C(O)N($R^{31}$)—, —S(O)$_s$—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{24}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

Accordingly to a further feature of the present invention there is provided a compound of formula (I) wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =C$R^8$—, =C$R^9$— and =C$R^{10}$—;

$R^3$ is hydrogen or optionally substituted $C_{1-6}$alkyl; wherein said optional substituents are selected from one or more $R^{11}$;

$R^4$ and $R^{34}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^4$ and $R^{34}$ may be independently optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{25}$— or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{27}$— or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an —NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^3$, $R^{15}$, $R^{17}$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$ and $R^{28}$ are independently selected from a direct bond, —O—, —N($R^{29}$)—, —C(O)—, —N($R^{30}$)C (O)—, —C(O)N($R^{31}$)—, —S(O)$_s$—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl or N-methyl-N-ethylsulphamoyl; and $R^{24}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt thereof.

According to a further feature of the invention there is provided a compound of formula (I) wherein:

$R^1$ and $R^2$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^1$ and $R^2$ independently of each other may be optionally substituted on carbon by one or more $R^6$; and wherein if said heterocyclyl contains an —NH— moiety that nitrogen may be optionally substituted by a group selected from $R^7$;

one of $X^1$, $X^2$, $X^3$ and $X^4$ is =N—, the other three are independently selected from =CR$^8$—, =CR$^9$— and =CR$^{10}$—;

$R^3$ is hydrogen or optionally substituted $C_{1-6}$alkyl; wherein said optional substituents are selected from one or more $R^{11}$;

$R^4$ and $R^{34}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^4$ and $R^{34}$ may be independently optionally substituted on carbon by one or more $R^{12}$; and wherein if said heterocyclyl contains an —NH— moiety that nitrogen may be optionally substituted by a group selected from $R^{13}$;

A is a direct bond or $C_{1-2}$alkylene; wherein said $C_{1-2}$alkylene may be optionally substituted by one or more $R^{14}$;

Ring C is carbocyclyl or heterocyclyl; wherein if said heterocyclyl contains an —NH— moiety that nitrogen may be optionally substituted by a group selected from $R^{15}$;

$R^5$ is selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl or heterocyclyl; wherein $R^5$ may be optionally substituted on carbon by one or more $R^{16}$; and wherein if said heterocyclyl contains an —NH— moiety that nitrogen may be optionally substituted by a group selected from $R^{17}$;

n is 0, 1, 2 or 3; wherein the values of $R^5$ may be the same or different;

$R^8$, $R^9$ and $R^{10}$ are independently selected from hydrogen, halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{25}$— or heterocyclyl-$R^{26}$—; wherein $R^8$, $R^9$ and $R^{10}$ independently of each other may be optionally substituted on carbon by one or more $R^{18}$; and wherein if said heterocyclyl contains an —NH— moiety that nitrogen may be optionally substituted by a group selected from $R^{19}$;

$R^6$, $R^{11}$, $R^{12}$, $R^{14}$, $R^{16}$ and $R^{18}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, carbocyclyl-$R^{27}$— or heterocyclyl-$R^{28}$—; wherein $R^6$, $R^{11}$, $R^{12}$, $R^{14}$, $R^{16}$ and $R^{18}$ independently of each other may be optionally substituted on carbon by one or more $R^{20}$; and wherein if said heterocyclyl contains an —NH— moiety that nitrogen may be optionally substituted by a group selected from $R^{21}$;

$R^7$, $R^{13}$, $R^{15}$, $R^{17}$, $R^{19}$ and $R^{21}$ are independently selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl; wherein $R^7$, $R^{13}$, $R^{15}$, $R^7$, $R^{19}$ and $R^{21}$ independently of each other may be optionally substituted on carbon by on or more $R^{22}$;

$R^{20}$ and $R^{22}$ are independently selected from halo, nitro, cyano, hydroxy, trifluoromethoxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, $C_{1-6}$alkylsulphonylamino, $C_{1-6}$alkylsulphonyl-N—($C_{1-6}$alkyl)amino, carbocyclyl-$R^{35}$— or heterocyclyl-$R^{36}$—; wherein $R^{20}$ and $R^{22}$ independently of each other may be optionally substituted on carbon by one or more $R^{23}$; and wherein if said heterocyclyl contains an —NH— moiety that nitrogen may be optionally substituted by a group selected from $R^{24}$;

$R^{25}$, $R^{26}$, $R^{27}$, $R^{28}$, $R^{35}$ and $R^{36}$ are independently selected from a direct bond, —O—, —N($R^{29}$)—, —C(O)—, —N($R^{30}$)C(O)—, —C(O)N($R^{31}$)—, —S(O)$_s$—, —NH=CH—, —SO$_2$N($R^{32}$)— or —N($R^{33}$)SO$_2$—; wherein $R^{29}$, $R^{30}$, $R^{31}$, $R^{32}$ and $R^{33}$ are independently selected from hydrogen or $C_{1-6}$alkyl and s is 0-2;

$R^{23}$ is selected from halo, nitro, cyano, hydroxy, trifluoromethoxy, trifluoromethyl, amino, carboxy, carbamoyl, mercapto, sulphamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulphinyl, ethylsulphinyl, mesyl, ethylsulphonyl, methoxycarbonyl, ethoxycarbonyl, N-methylsulphamoyl, N-ethylsulphamoyl, N,N-dimethylsulphamoyl, N,N-diethylsulphamoyl, N-methyl-N-ethylsulphamoyl or phenyl; and $R^{24}$ is selected from $C_{1-6}$alkyl, $C_{1-6}$alkanoyl, $C_{1-6}$alkylsulphonyl, $C_{1-6}$alkoxycarbonyl, carbamoyl, N—$(C_{1-6}$alkyl)carbamoyl, N,N—$(C_{1-6}$alkyl)carbamoyl, benzyl, benzyloxycarbonyl, benzoyl and phenylsulphonyl;

or a pharmaceutically acceptable salt thereof.

Particular values of the variable groups contained in formula (I) are as follows. Such values may be used, where appropriate, with any of the definitions, claims or embodiments defined hereinbefore or hereinafter.

$R^1$ is $C_{1-6}$alkoxy or carbocyclyl.

$R^1$ is $C_{1-6}$alkyl, $C_{1-6}$alkoxy and cyclopropyl.

$R^1$ is isopropoxy or cyclopropyl.

$R^1$ is $C_{1-6}$alkoxy.

$R^1$ is cyclopropyl.

$R^1$ is isopropoxy.

$R^1$ is methyl, t-butyl, isopropoxy or cyclopropyl.

$R^1$ is hydrogen.

$R^1$ and $R^2$ are independently selected from hydrogen, $C_{1-6}$alkoxy and carbocyclyl.

$R^1$ and $R^2$ are independently selected from hydrogen, $C_{1-6}$alkyl, $C_{1-6}$alkoxy and carbocyclyl.

$R^1$ and $R^2$ are independently selected from hydrogen, $C_{1-6}$alkoxy and cyclopropyl.

$R^1$ and $R^2$ are independently selected from hydrogen, $C_{1-6}$alkyl, $C_{1-6}$alkoxy and cyclopropyl.

$R^1$ and $R^2$ are independently selected from hydrogen, isopropoxy and cyclopropyl.

$R^1$ and $R^2$ are independently selected from hydrogen, methyl, t-butyl, isopropoxy and cyclopropyl.

$R^1$ is $C_{1-6}$alkoxy or carbocyclyl and $R^2$ is hydrogen.

$R^1$ is $C_{1-6}$alkyl, $C_{1-6}$alkoxy or carbocyclyl and $R^2$ is hydrogen.

$R^1$ is $C_{1-6}$alkoxy and cyclopropyl and $R^2$ is hydrogen.

$R^1$ is $C_{1-6}$alkyl, $C_{1-6}$alkoxy and cyclopropyl and $R^2$ is hydrogen.

$R^1$ is $C_{1-6}$alkoxy and $R^2$ is hydrogen.

$R^1$ is isopropoxy and $R^2$ is hydrogen.

$R^1$ is cyclopropyl and $R^2$ is hydrogen.

$R^1$ is isopropoxy or cyclopropyl and $R^2$ is hydrogen.

$R^1$ is methyl, t-butyl, isopropoxy or cyclopropyl and $R^2$ is hydrogen.

$X^1$ is =N—, $X^2$ is =$CR^8$—, $X^3$ is =$CR^9$— and $X^4$ is =$CR^{10}$—.

$X^2$ is =N—, $X^1$ is =$CR^8$—, $X^3$ is =$CR^9$— and $X^4$ is =$CR^{10}$—.

$X^3$ is =N—, $X^2$ is =$CR^8$—, $X^1$ is =$CR^9$— and $X^4$ is =$CR^{10}$—.

$X^4$ is =N—, $X^2$ is =$CR^8$—, $X^3$ is =$CR^9$— and $X^4$ is =$CR^{10}$—.

$X^3$ or $X^4$ is =N—, $X^1$ and $X^2$ and the other of $X^3$ and $X^4$ are independently selected from =$CR^8$—, =$CR^9$— and =$CR^{10}$—.

$R^3$ is hydrogen.

$R^3$ is optionally substituted $C_{1-6}$alkyl; wherein said optional substituents are selected from one or more $R^{11}$.

$R^4$ is not hydrogen.

$R^4$ is selected from hydrogen or $C_{1-6}$alkyl; wherein $R^4$ may be optionally substituted on carbon by one or more $R^{12}$; wherein $R^{12}$ is selected from hydroxy.

$R^4$ is selected from hydrogen or $C_{1-6}$alkyl; wherein $R^4$ may be optionally substituted on carbon by one or more $R^{12}$; wherein $R^{12}$ is selected from hydroxy and $R^{34}$ is hydrogen.

$R^4$ and $R^{34}$ are independently selected from hydrogen or $C_{1-6}$alkyl; wherein $R^4$ and $R^{34}$ may be independently optionally substituted on carbon by one or more $R^{12}$; wherein $R^{12}$ is selected from hydroxy.

$R^4$ is selected from hydrogen or methyl; wherein $R^4$ may be optionally substituted on carbon by one or more $R^{12}$; wherein $R^{12}$ is selected from hydroxy.

$R^4$ is selected from hydrogen or methyl; wherein $R^4$ may be optionally substituted on carbon by one or more $R^{12}$; wherein $R^{12}$ is selected from hydroxy and $R^{34}$ is hydrogen.

$R^4$ and $R^{34}$ are independently selected from hydrogen or methyl; wherein $R^4$ and $R^{34}$ may be independently optionally substituted on carbon by one or more $R^{12}$; wherein $R^{12}$ is selected from hydroxy.

$R^4$ is selected from hydrogen, methyl or hydroxymethyl.

$R^4$ is selected from hydrogen, methyl or hydroxymethyl and $R^{34}$ is hydrogen.

$R^4$ and $R^{34}$ are independently selected from hydrogen, methyl or hydroxymethyl.

$R^{34}$ is selected from hydrogen.

$R^{34}$ is selected from hydrogen or hydroxymethyl.

$R^4$ is selected from methyl or hydroxymethyl.

$R^4$ is selected from methyl or hydroxymethyl and $R^{34}$ is hydrogen.

$R^4$ is selected from methyl and $R^{34}$ is hydrogen.

$R^4$ is selected from hydroxymethyl and $R^{34}$ is hydrogen.

A is a direct bond.

A is $C_{1-2}$alkylene; wherein said $C_{1-2}$alkylene may be optionally substituted by one or more $R^{14}$.

Ring C is carbocyclyl.

Ring C is or heterocyclyl; wherein if said heterocyclyl contains an —NH— moiety that nitrogen may be optionally substituted by a group selected from $R^{15}$;

Ring C is carbocyclyl or heterocyclyl.

Ring C is phenyl, pyridyl or pyrimidinyl.

Ring C is phenyl, pyrid-2-yl, pyrid-3-yl or pyrimidin-2-yl.

Ring C is phenyl.

Ring C is pyridyl.

Ring C is pyrid-2-yl.

$R^5$ is selected from halo, $C_{1-6}$alkanoylamino, $C_{1-6}$alkylsulphonylamino or carbocyclyl-$R^{37}$—; wherein $R^{37}$ is —C(O)N($R^{31}$)—; wherein $R^{31}$ is hydrogen.

$R^5$ is halo.

$R^5$ is selected from fluoro, acetylamino, mesylamino or cyclopropyl-$R^{37}$—; wherein $R^{37}$ is —C(O)N($R^{31}$)—; wherein $R^{31}$ is hydrogen.

$R^5$ is fluoro.

$R^5$ is selected from fluoro, acetylamino, mesylamino or cyclopropylcarbonylamino.

n is 0.

n is 1.

n is 1 or 2; wherein the values of $R^5$ may be the same or different.

n is 2; wherein the values of $R^5$ may be the same or different.

n is 3; wherein the values of $R^5$ may be the same or different.

Ring C and $(R^5)_n$ together form 4-fluorophenyl; wherein the fluoro group is para to the A group of formula (I).

Ring C and $(R^5)_n$ together form 4-fluorophenyl, 5-fluoropyrid-2-yl, 3,5-difluoropyrid-2-yl, 5-fluoropyrimidin-2-yl, 4-fluoro-3-mesylaminophenyl, 6-fluoropyrid-3-yl, 4-fluoro-3-acetylaminophenyl and 4-fluoro-3-cyclopropylcabonylamino.

Ring C and $(R^5)_n$ together form 5-fluoropyrid-2-yl; wherein the fluoro group is para to the A group of formula (I).

$R^8$, $R^9$ and $R^{10}$ are independently selected from hydrogen, halo, nitro, cyano, amino, carboxy, carbamoyl, $C_{1-6}$alkyl, $C_{1-6}$alkanoyl, N—($C_{1-6}$alkyl)amino or carbocyclyl-$R^{25}$—; wherein $R^8$, $R^9$ and $R^{10}$ independently of each other may be optionally substituted on carbon by one or more $R^{18}$;

$R^{18}$ is selected from hydroxy, amino, N—($C_{1-6}$alkyl)amino, $C_{1-6}$alkanoylamino, $C_{1-6}$alkylsulphonylamino, carbocyclyl-$R^{27}$— or heterocyclyl-$R^{28}$—; wherein $R^{18}$ may be optionally substituted on carbon by one or more $R^{20}$; and wherein if said heterocyclyl contains an —N—H— moiety that nitrogen may be optionally substituted by a group selected from $R^{21}$;

$R^{20}$ is selected from halo, amino, $C_{1-6}$alkyl, N,N—($C_{1-6}$alkyl)$_2$amino, $C_{1-6}$alkylsulphonyl-N—($C_{1-6}$alkyl)amino, carbocyclyl-$R^{35}$— or heterocyclyl-$R^{36}$—; wherein $R^{20}$ may be optionally substituted on carbon by one or more $R^{23}$;

$R^{21}$ is selected from $C_{1-6}$alkylsulphonyl;

$R^{23}$ is dimethylamino or phenyl; and $R^{27}$, $R^{28}$, $R^{35}$ and $R^{36}$ are independently selected from a direct bond, —C(O)N($R^{31}$)—, —NH=CH— or —SO$_2$N($R^{32}$)—; wherein $R^{31}$ and $R^{32}$ are independently selected from hydrogen or $C_{1-6}$alkyl.

$R^8$, $R^9$ and $R^{10}$ are independently selected from hydrogen, halo, nitro, cyano, amino, carbamoyl and $C_{1-6}$alkyl; wherein $R^8$, $R^9$ and $R^{10}$ independently of each other may be optionally substituted on carbon by one or more $R^{18}$; wherein $R^{18}$ is selected from amino, $C_{1-6}$alkanoylamino, $C_{1-6}$alkylsulphonylamino or heterocyclyl-$R^{28}$—; wherein $R^{18}$ may be optionally substituted on carbon by one or more $R^{20}$;

$R^{20}$ is amino; and $R^{28}$ is —C(O)N($R^{31}$)—; wherein $R^{31}$ is hydrogen.

$R^8$, $R^9$ and $R^{10}$ are independently selected from hydrogen, fluoro, chloro, iodo, nitro, cyano, amino, carboxy, carbamoyl, methyl, isopropyl, formyl, methylamino, isopropylamino or cyclopropyl-$R^{25}$—; wherein $R^8$, $R^9$ and $R^{10}$ independently of each other may be optionally substituted on carbon by one or more $R^{18}$;

$R^{18}$ is selected from hydroxy, amino, methylamino, acetylamino, propionylamino, 3-methylbutanoylamino, mesylamino, cyclopropyl-$R^{27}$—, phenyl-$R^{27}$—, tetrahydrofuran-2-yl-$R^{28}$—, furan-2-yl-$R^{28}$—, pyrrol-2-yl-$R^{28}$—, isoxaxol-5-yl-$R^{28}$—, isoxaxol-4-yl-$R^{28}$—, piperidin-4-yl-$R^{28}$—, thien-2-yl-$R^{28}$—, pyrid-3-yl-$R^{28}$—, pyrid-4-yl-$R^{28}$—, tetrahydro-2H-thiopyran-4-yl-$R^{28}$—, morpholino-$R^{28}$— or 2-oxopyrrolidin-5-yl-$R^{28}$—; wherein $R^{18}$ may be optionally substituted on carbon by one or more $R^{20}$; and wherein if said heterocyclyl contains an —NH— moiety that nitrogen may be optionally substituted by a group selected from $R^{21}$;

$R^{20}$ is selected from fluoro, amino, methyl, dimethylamino, N-(isopropyl)-N-(mesyl)amino, N-(ethyl)-N-(mesyl)amino, phenyl-$R^{35}$—, thien-2-yl-$R^{36}$—, thien-3-yl-$R^{36}$—, pyrid-3-yl-$R^{36}$— or morpholino-$R^{36}$—; wherein $R^{20}$ may be optionally substituted on carbon by one or more $R^{23}$;

$R^{21}$ is selected from mesyl;

$R^{23}$ is dimethylamino or phenyl; and $R^{27}$, $R^{28}$, $R^{35}$ and $R^{36}$ are independently selected from a direct bond, —C(O)N($R^{31}$)—, —NH=CH— or —SO$_2$N($R^{32}$)—; wherein $R^{31}$ and $R^{32}$ are independently selected from hydrogen or methyl.

$R^8$, $R^9$ and $R^{10}$ are independently selected from hydrogen, fluoro, chloro, nitro, cyano, amino, carbamoyl and methyl; wherein $R^8$, $R^9$ and $R^{10}$ independently of each other may be optionally substituted on carbon by one or more $R^{18}$; wherein $R^{18}$ is selected from amino, acetylamino, mesylamino or 2-oxopyrrolidin-5-yl-$R^{28}$—; wherein $R^{18}$ may be optionally substituted on carbon by one or more $R^{20}$;

$R^{20}$ is amino; and $R^{28}$ is —C(O)N($R^{31}$)—; wherein $R^{31}$ is hydrogen.

$R^8$, $R^9$ and $R^{10}$ are independently selected from hydrogen, fluoro, chloro, iodo, nitro, cyano, amino, carboxy, carbamoyl, formyl, methylamino, hydroxymethyl, acetylaminomethyl, (2-aminoacetyl)aminomethyl, (2-morpholinoacetyl)aminomethyl, (R)-2-oxopyrrolidin-5-yl-carbonylaminomethyl, (S)-2-oxopyrrolidin-5-yl-carbonylaminomethyl, (R,S)-2-oxopyrrolidin-5-yl-carbonylaminomethyl, isoxaxol-5-yl-carbonylaminomethyl, mesylaminomethyl, morpholinomethyl, benzoylaminomethyl, pyrid-3-yl-carbonylaminomethyl, 6-dimethylaminopyrid-3-yl-carbonylaminomethyl, 6-morpholinopyrid-3-yl-carbonylaminomethyl, pyrid-4-yl-carbonylaminomethyl, 5-methylisoxaxol-4-yl-carbonylaminomethyl, thien-2-yl-carbonylaminomethyl, 4-dimethylaminobenzylcarbonylaminomethyl, 2-(N-(isopropyl)-N-(mesyl)amino)acetylaminomethyl, 2-(N-(phenethyl)-N-(mesyl)amino)acetylaminomethyl, 1-mesylpiperidin-1-ylcarbonylaminomethyl, 2-(pyrid-3-yl)acetylaminomethyl, tetrahydro-2H-thiopyran-4-yl-carbonylaminomethyl, 2-(thien-2-yl)acetylcarbonylaminomethyl, 2-(thien-3-yl)acetylcarbonylaminomethyl, 3-phenylpropionylaminomethyl, 2-(N-benzoyl-N-methylamino)acetylaminomethyl, 4-dimethylaminobenzoylaminomethyl, phenylsulphonylaminomethyl, 2-amino-3-methylbutanoylaminomethyl, cyclopropylcarbonylaminomethyl, pyrrol-2-yl-carbonylaminomethyl, tetrahydrofuran-2-yl-carbonylaminomethyl, furan-2-yl-carbonylaminomethyl, cyclopropylsulphonylaminomethyl, (cyclopropylimino)methyl, methylaminomethyl, trifluoromesylaminomethyl, isopropyl, isopropylamino or methylamino.

$R^8$, $R^9$ and $R^{10}$ are independently selected from hydrogen, fluoro, chloro, nitro, cyano, amino, carboxy, carbamoyl, formyl, methylamino, hydroxymethyl, acetylaminomethyl, (2-aminoacetyl)aminomethyl, (2-morpholinoacetyl)aminomethyl, (R)-2-oxopyrrolidin-5-yl-carbonylaminomethyl, (S)-2-oxopyrrolidin-5-yl-carbonylaminomethyl, (R,S)-2-oxopyrrolidin-5-yl-carbonylaminomethyl, isoxaxol-5-yl-carbonylaminomethyl, mesylaminomethyl, morpholinomethyl, benzoylaminomethyl, pyrid-3-yl-carbonylaminomethyl, 6-dimethylaminopyrid-3-yl-carbonylaminomethyl, 6-morpholinopyrid-3-yl-carbonylaminomethyl, pyrid-4-yl-carbonylaminomethyl, 5-methylisoxaxol-4-yl-carbonylaminomethyl, thien-2-yl-carbonylaminomethyl, 4-dimethylaminobenzylcarbonylaminomethyl, 2-(N-(isopropyl)-N-(mesyl)amino)acetylaminomethyl, 2-(N-(phenethyl)-N-(mesyl)amino)acetylaminomethyl, 1-mesylpiperidin-1-ylcarbonylaminomethyl, 2-(pyrid-3-yl)acetylaminomethyl, tetrahydro-2H-thiopyran-4-yl-carbonylaminomethyl, 2-(thien-2-yl)acetylcarbonylaminomethyl, 2-(thien-3-yl)acetylcarbonylaminomethyl, 3-phenylpropionylaminomethyl, 2-(N-benzoyl-N-methylamino)acetylaminomethyl, 4-dimethylaminobenzoylaminomethyl, phenylsulphonylaminomethyl, 2-amino-3-methylbutanoylaminomethyl, cyclopropylcarbonylaminomethyl, pyrrol-2-yl-carbonylaminomethyl, tetrahydrofuran-2-yl-carbonylaminomethyl, furan-2-yl-carbonylaminomethyl, cyclopropylsulphonylaminomethyl, (cyclopropylimino)methyl, methylaminomethyl, trifluoromesylaminomethyl, isopropyl, isopropylamino or methylamino.

$R^8$, $R^9$ and $R^{10}$ are independently selected from hydrogen, fluoro, chloro, nitro, cyano, amino, carbamoyl, aminomethyl, acetylaminomethyl, mesylaminomethyl, 2-oxopyrrolidin-5-ylcarbonylaminomethyl and (2-aminoacetyl)aminomethyl.

$R^8$, $R^9$ and $R^{10}$ are independently selected from hydrogen, fluoro and cyano.

Therefore in a further aspect of the invention there is provided a compound of formula (I) (as depicted herein above) wherein:

$R^1$ and $R^2$ are independently selected from hydrogen, $C_{1-6}$alkoxy and carbocyclyl;

$X^3$ or $X^4$ is =N—, $X^1$ and $X^2$ and the other of $X^3$ and $X^4$ are independently selected from =CR$^8$—, =CR$^9$— and =CR$^{10}$—;

$R^3$ is hydrogen;

$R^4$ is selected from hydrogen or $C_{1-6}$alkyl; wherein $R^4$ may be optionally substituted on carbon by one or more $R^{12}$;

$R^{34}$ is hydrogen;

A is a direct bond;

Ring C is carbocyclyl;

$R^5$ is halo;

n is 1;

$R^8$, $R^9$ and $R^{10}$ are independently selected from hydrogen, halo, nitro, cyano, amino, carbamoyl and $C_{1-6}$alkyl; wherein $R^8$, $R^9$ and $R^{10}$ independently of each other may be optionally substituted on carbon by one or more $R^{18}$;

$R^{12}$ is selected from hydroxy;

$R^{18}$ is selected from amino, $C_{1-6}$alkanoylamino, $C_{1-6}$alkylsulphonylamino or heterocyclyl-$R^{28}$—; wherein $R^{18}$ may be optionally substituted on carbon by one or more $R^{20}$;

$R^{20}$ is amino; and $R^{28}$ is —C(O)N($R^{31}$)—; wherein $R^{31}$ is hydrogen;

or a pharmaceutically acceptable salt thereof.

Therefore in a further aspect of the invention there is provided a compound of formula (I) (as depicted herein above) wherein:

$R^1$ and $R^2$ are independently selected from hydrogen, $C_{1-6}$alkyl, $C_{1-6}$alkoxy and carbocyclyl;

$X^3$ or $X^4$ is =N—, $X^1$ and $X^2$ and the other of $X^3$ and $X^4$ are independently selected from =CR$^8$—, =CR$^9$— and =CR$^{10}$—;

$R^3$ is hydrogen;

$R^4$ and $R^{34}$ are independently selected from hydrogen or $C_{1-6}$alkyl; wherein $R^4$ and $R^{34}$ may be independently optionally substituted on carbon by one or more $R^{12}$;

A is a direct bond;

Ring C is carbocyclyl;

$R^5$ is halo;

n is 1;

$R^8$, $R^9$ and $R^{10}$ are independently selected from hydrogen, halo, nitro, cyano, amino, carbamoyl and $C_{1-6}$alkyl; wherein $R^8$, $R^9$ and $R^{10}$ independently of each other may be optionally substituted on carbon by one or more $R^{18}$;

$R^{12}$ is selected from hydroxy;

$R^{18}$ is selected from amino, $C_{1-6}$alkanoylamino, $C_{1-6}$alkylsulphonylamino or heterocyclyl-$R^{28}$—; wherein $R^{18}$ may be optionally substituted on carbon by one or more $R^{20}$;

$R^{20}$ is amino; and $R^{28}$ is —C(O)N($R^{31}$)—; wherein $R^{31}$ is hydrogen;

or a pharmaceutically acceptable salt thereof.

Therefore in a further aspect of the invention there is provided a compound of formula (I) (as depicted herein above) wherein:

$R^1$ is $C_{1-6}$alkyl, $C_{1-6}$alkoxy or carbocyclyl;

$R^2$ is hydrogen;

$X^3$ or $X^4$ is =N—, $X^1$ and $X^2$ and the other of $X^3$ and $X^4$ are independently selected from =CR$^8$—, =CR$^9$— and =CR$^{10}$—;

$R^3$ is hydrogen;

$R^4$ and $R^{34}$ are independently selected from hydrogen or $C_{1-6}$alkyl; wherein $R^4$ and $R^{34}$ may be independently optionally substituted on carbon by one or more $R^{12}$; wherein $R^{12}$ is selected from hydroxy;

A is a direct bond;

Ring C is carbocyclyl;

$R^5$ is halo;

n is 1;

$R^8$, $R^9$ and $R^{10}$ are independently selected from hydrogen, halo, nitro, cyano, amino, carboxy, carbamoyl, $C_{1-6}$alkyl, $C_{1-6}$alkanoyl, N—($C_{1-6}$alkyl)amino or carbocyclyl-$R^{25}$—; wherein $R^8$, $R^9$ and $R^{10}$ independently of each other may be optionally substituted on carbon by one or more $R^{18}$;

$R^{18}$ is selected from hydroxy, amino, N—($C_{1-6}$alkyl)amino, $C_{1-6}$alkanoylamino, $C_{1-6}$alkylsulphonylamino, carbocyclyl-$R^{27}$— or heterocyclyl-$R^{28}$—; wherein $R^{18}$ may be optionally substituted on carbon by one or more $R^{20}$; and wherein if said heterocyclyl contains an —NH— moiety that nitrogen may be optionally substituted by a group selected from $R^1$;

$R^{20}$ is selected from halo, amino, $C_{1-6}$alkyl, N,N—($C_{1-6}$alkyl)$_2$amino, $C_{1-6}$alkylsulphonyl-N—($C_{1-6}$alkyl)amino, carbocyclyl-$R^{35}$— or heterocyclyl-$R^{36}$—; wherein $R^{20}$ may be optionally substituted on carbon by one or more $R^3$;

$R^{21}$ is selected from $C_{1-6}$alkylsulphonyl;

$R^{23}$ is dimethylamino or phenyl; and $R^{27}$, $R^{28}$, $R^{35}$ and $R^{36}$ are independently selected from a direct bond, —C(O)N($R^{31}$)—, —NH=CH— or —SO$_2$N($R^{32}$)—; wherein $R^{31}$ and $R^{32}$ are independently selected from hydrogen or $C_{1-6}$alkyl;

or a pharmaceutically acceptable salt thereof.

Therefore in a further aspect of the invention there is provided a compound of formula (I) (as depicted herein above) wherein:

$R^1$ is $C_{1-6}$alkyl, $C_{1-6}$alkoxy or carbocyclyl;
$R^2$ is hydrogen;
$X^3$ or $X^4$ is =N—, $X^1$ and $X^2$ and the other of $X^3$ and $X^4$ are independently selected from =$CR^8$—, =$CR^9$— and =$CR^{10}$—;
$R^3$ is hydrogen;
$R^4$ and $R^{34}$ are independently selected from hydrogen or $C_{1-6}$alkyl; wherein $R^4$ and $R^{34}$ may be independently optionally substituted on carbon by one or more $R^{12}$; wherein $R^{12}$ is selected from hydroxy;
A is a direct bond;
Ring C is carbocyclyl or heterocyclyl;
$R^5$ is selected from fluoro, acetylamino, mesylamino or cyclopropyl-$R^{37}$—; wherein $R^{37}$ is —C(O)N($R^{31}$)—; wherein $R^{31}$ is hydrogen;
n is 1 or 2; wherein the values of $R^5$ may be the same or different;
$R^8$, $R^9$ and $R^{10}$ are independently selected from hydrogen, halo, nitro, cyano, amino, carboxy, carbamoyl, $C_{1-6}$alkyl, $C_{1-6}$alkanoyl, N—($C_{1-6}$alkyl)amino or carbocyclyl-$R^{25}$—; wherein $R^8$, $R^9$ and $R^{10}$ independently of each other may be optionally substituted on carbon by one or more $R^{18}$;
$R^{18}$ is selected from hydroxy, amino, N—($C_{1-6}$alkyl)amino, $C_{1-6}$alkanoylamino, $C_{1-6}$alkylsulphonylamino, carbocyclyl-$R^{27}$— or heterocyclyl-$R^{28}$—; wherein $R^{18}$ may be optionally substituted on carbon by one or more $R^{20}$; and wherein if said heterocyclyl contains an —NH— moiety that nitrogen may be optionally substituted by a group selected from $R^{21}$;
$R^{20}$ is selected from halo, amino, $C_{1-6}$alkyl, N,N—($C_{1-6}$alkyl)$_2$amino, $C_{1-6}$alkylsulphonyl-N—($C_{1-6}$alkyl)amino, carbocyclyl-$R^{35}$— or heterocyclyl-$R^{36}$—; wherein $R^{20}$ may be optionally substituted on carbon by one or more $R^{23}$;
$R^{21}$ is selected from $C_{1-6}$alkylsulphonyl;
$R^{23}$ is dimethylamino or phenyl; and
$R^{27}$, $R^{28}$, $R^{35}$ and $R^{36}$ are independently selected from a direct bond, —C(O)N($R^{31}$)—, —NH=CH— or —SO$_2$N($R^{32}$)—; wherein $R^{31}$ and $R^{32}$ are independently selected from hydrogen or $C_{1-6}$alkyl;
or a pharmaceutically acceptable salt thereof.

Therefore in a further aspect of the invention there is provided a compound of formula (I) (as depicted herein above) wherein:

$R^1$ is isopropoxy or cyclopropyl;
$R^2$ is hydrogen;
$X^3$ or $X^4$ is =N—, $X^1$ and $X^2$ and the other of $X^3$ and $X^4$ are independently selected from =$CR^8$—, =$CR^9$— and =$CR^{10}$—;
$R^3$ is hydrogen;
$R^4$ is selected from hydrogen, methyl or hydroxymethyl;
$R^{34}$ is hydrogen;
A is a direct bond;
Ring C is phenyl;
$R^5$ is fluoro;
n is 1; and
$R^8$, $R^9$ and $R^{10}$ are independently selected from hydrogen, fluoro, chloro, nitro, cyano, amino, carbamoyl, aminomethyl, acetylaminomethyl, mesylaminomethyl, 2-oxopyrrolidin-5-ylcarbonylaminomethyl and (2-aminoacetyl)aminomethyl;
or a pharmaceutically acceptable salt thereof.

Therefore in a further aspect of the invention there is provided a compound of formula (I) (as depicted herein above) wherein:

$R^1$ is methyl, t-butyl, isopropoxy or cyclopropyl;
$R^2$ is hydrogen;
$X^3$ or $X^4$ is =N—, $X^1$ and $X^2$ and the other of $X^3$ and $X^4$ are independently selected from =$CR^8$—, =$CR^9$— and =$CR^{10}$—;
$R^3$ is hydrogen;
$R^4$ is selected from hydrogen, methyl or hydroxymethyl;
$R^{34}$ is selected from hydrogen or hydroxymethyl;
A is a direct bond;
Ring C is phenyl;
$R^5$ is fluoro;
n is 1; and
$R^8$, $R^9$ and $R^{10}$ are independently selected from hydrogen, fluoro, chloro, nitro, cyano, amino, carbamoyl, aminomethyl, acetylaminomethyl, mesylaminomethyl, 2-oxopyrrolidin-5-ylcarbonylaminomethyl and (2-aminoacetyl)aminomethyl;
or a pharmaceutically acceptable salt thereof.

Therefore in a further aspect of the invention there is provided a compound of formula (I) (as depicted herein above) wherein:

$R^1$ is methyl, t-butyl, isopropoxy or cyclopropyl;
$R^2$ is hydrogen;
$X^3$ or $X^4$ is =N—, $X^1$ and $X^2$ and the other of $X^3$ and $X^4$ are independently selected from =$CR^8$—, =$CR^9$— and =$CR^{10}$—;
$R^3$ is hydrogen;
$R^4$ and $R^{34}$ are independently selected from hydrogen, methyl or hydroxymethyl;
A is a direct bond;
Ring C is phenyl;
$R^5$ is fluoro;
n is 1;
$R^8$, $R^9$ and $R^{10}$ are independently selected from hydrogen, fluoro, chloro, nitro, cyano, amino, carboxy, carbamoyl, formyl, methylamino, hydroxymethyl, acetylaminomethyl, (2-aminoacetyl)aminomethyl, (2-morpholinoacetyl)aminomethyl, (R)-2-oxopyrrolidin-5-yl-carbonylaminomethyl, (S)-2-oxopyrrolidin-5-yl-carbonylaminomethyl, (R,S)-2-oxopyrrolidin-5-yl-carbonylaminomethyl, isoxaxol-5-yl-carbonylaminomethyl, mesylaminomethyl, morpholinomethyl, benzoylaminomethyl, pyrid-3-yl-carbonylaminomethyl, 6-dimethylaminopyrid-3-yl-carbonylaminomethyl, 6-morpholinopyrid-3-yl-carbonylaminomethyl, pyrid-4-yl-carbonylaminomethyl, 5-methylisoxaxol-4-yl-carbonylaminomethyl, thien-2-yl-carbonylaminomethyl, 4-dimethylaminobenzylcarbonylaminomethyl, 2-(N-(isopropyl)-N-(mesyl)amino)acetylaminomethyl, 2-(N-(phenethyl)-N-(mesyl)amino)acetylaminomethyl, 1-mesylpiperidin-1-ylcarbonylaminomethyl, 2-(pyrid-3-yl)acetylaminomethyl, tetrahydro-2H-thiopyran-4-yl-carbonylaminomethyl, 2-(thien-2-yl)acetylcarbonylaminomethyl, 2-(thien-3-yl)acetylcarbonylaminomethyl, 3-phenylpropionylaminomethyl, 2-(N-benzoyl-N-methylamino)acetylaminomethyl, 4-dimethylaminobenzoylaminomethyl, phenylsulphonylaminomethyl, 2-amino-3-methylbutanoylaminomethyl, cyclopropylcarbonylaminomethyl, pyrrol-2-yl-carbonylaminomethyl, tetrahydrofuran-2-yl-carbonylaminomethyl, furan-2-yl-carbonylaminomethyl, cyclopropylsulphonylaminomethyl, (cyclopropylimino)methyl, methylaminomethyl, trifluoromesylaminomethyl, isopropyl, isopropylamino or methylamino;
or a pharmaceutically acceptable salt thereof.

Therefore in a further aspect of the invention there is provided a compound of formula (I) (as depicted herein above) wherein:

$R^1$ is methyl, t-butyl, isopropoxy or cyclopropyl;
$R^2$ is hydrogen;
$X^3$ or $X^4$ is =N—, $X^1$ and $X^2$ and the other of $X^3$ and $X^4$ are independently selected from =$CR^8$—, =$CR^9$— and =$CR^{10}$—;
$R^3$ is hydrogen;
$R^4$ and $R^{34}$ are independently selected from hydrogen, methyl or hydroxymethyl;
A is a direct bond;
Ring C is phenyl, pyrid-2-yl, pyrid-3-yl or pyrimidin-2-yl;
$R^5$ is selected from fluoro, acetylamino, mesylamino or cyclopropylcarbonylamino;
n is 1 or 2; wherein the values of $R^5$ may be the same or different;
$R^8$, $R^9$ and $R^{10}$ are independently selected from hydrogen, fluoro, chloro, iodo, nitro, cyano, amino, carboxy, carbamoyl, formyl, methylamino, hydroxymethyl, acetylaminomethyl, (2-aminoacetyl)aminomethyl, (2-morpholinoacetyl)aminomethyl, (R)-2-oxopyrrolidin-5-yl-carbonylaminomethyl, (S)-2-oxopyrrolidin-5-yl-carbonylaminomethyl, (R,S)-2-oxopyrrolidin-5-yl-carbonylaminomethyl, isoxaxol-5-yl-carbonylaminomethyl, mesylaminomethyl, morpholinomethyl, benzoylaminomethyl, pyrid-3-yl-carbonylaminomethyl, 6-dimethylaminopyrid-3-yl-carbonylaminomethyl, 6-morpholinopyrid-3-yl-carbonylaminomethyl, pyrid-4-yl-carbonylaminomethyl, 5-methylisoxaxol-4-yl-carbonylaminomethyl, thien-2-yl-carbonylaminomethyl, 4-dimethylaminobenzylcarbonylaminomethyl, 2-(N-(isopropyl)-N-(mesyl)amino)acetylaminomethyl, 2-(N-(phenethyl)-N-(mesyl)amino)acetylaminomethyl, 1-mesylpiperidin-1-ylcarbonylaminomethyl, 2-(pyrid-3-yl)acetylaminomethyl, tetrahydro-2H-thiopyran-4-yl-carbonylaminomethyl, 2-(thien-2-yl)acetylcarbonylaminomethyl, 2-(thien-3-yl)acetylcarbonylaminomethyl, 3-phenylpropionylaminomethyl, 2-(N-benzoyl-N-methylamino)acetylaminomethyl, 4-dimethylaminobenzoylaminomethyl, phenylsulphonylaminomethyl, 2-amino-3-methylbutanoylaminomethyl, cyclopropylcarbonylaminomethyl, pyrrol-2-yl-carbonylaminomethyl, tetrahydrofuran-2-yl-carbonylaminomethyl, furan-2-yl-carbonylaminomethyl, cyclopropylsulphonylaminomethyl, (cyclopropylimino)methyl, methylaminomethyl, trifluoromesylaminomethyl, isopropyl, isopropylamino or methylamino;
or a pharmaceutically acceptable salt thereof.

In a further aspect of the invention there is provided a compound of formula (Ia):

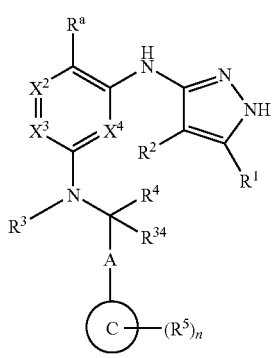

wherein $R^a$ is nitro or amino; and other variable groups are as defined herein above.

In a further aspect of the invention there is provided a compound of formula (Ib):

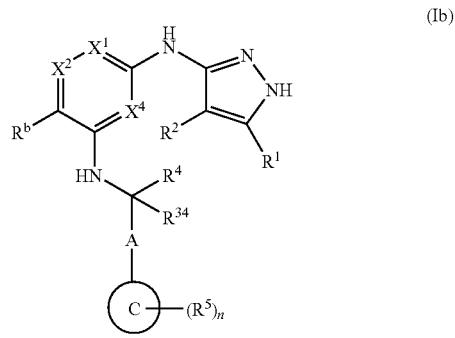

wherein $R^b$ is nitro or amino; and other variable groups are as defined herein above.

In another aspect of the invention, preferred compounds of the invention are any one of the Examples or a pharmaceutically acceptable salt thereof.

In another aspect of the invention, preferred compounds of the invention are any one of Examples 1, 6, 11, 16, 64, 110, 112, 113, 119 and 120 or a pharmaceutically acceptable salt thereof.

In an additional embodiment the present invention provides a compound of formula (I), or a pharmaceutically acceptable salt thereof, for use as a medicament.

In an additional embodiment the present invention provides a compound of formula (I), or a pharmaceutically acceptable salt thereof, for use in the manufacture of a medicament for use in the inhibition of Trk activity.

In an additional embodiment the present invention provides a compound of formula (I), or a pharmaceutically acceptable salt thereof, for use in the manufacture of a medicament for use in the treatment or prophylaxis of cancer.

In an additional embodiment the present invention provides a compound of the formula (I), or a pharmaceutically acceptable salt thereof, for use in the manufacture of a medicament for use in the treatment of cancer in a warm-blooded animal such as man.

In an additional embodiment the present invention provides a compound of the formula (a), or a pharmaceutically acceptable salt thereof, for use in the manufacture of a medicament for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the manufacture of a medicament for use in the production of an anti-proliferative effect.

In an additional embodiment the present invention provides a method of inhibiting Trk activity comprising administering to a host in need of such treatment a therapeutically effective amount of a compound of formula (a), or a pharmaceutically acceptable salt thereof.

In an additional embodiment the present invention provides a method for the treatment of cancer comprising administering to a host in need of such treatment a therapeutically effective amount of a compound of formula (a), or a pharmaceutically acceptable salt thereof.

In an additional embodiment the present invention provides a method for the treatment or prophylaxis of cancer comprising administering a therapeutically effective amount of a compound of formula (I) or a pharmaceutically acceptable salt thereof.

In an additional embodiment the present invention provides a method for the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man comprising administering a therapeutically effective amount of a compound of formula (I) or a pharmaceutically acceptable salt thereof.

In an additional embodiment the present invention provides a method of producing an anti-proliferative effect in a warm-blooded animal, such as man, in need of such treatment which comprises administering to said animal an effective amount of a compound of formula (I), or a pharmaceutically acceptable salt thereof.

In an additional embodiment the present invention provides a pharmaceutical composition comprising a compound of formula (I), or a pharmaceutically acceptable salt thereof, together with at least one pharmaceutically acceptable carrier, diluent or excipient.

In an additional embodiment the present invention provides a pharmaceutical composition comprising a compound of formula (I), or a pharmaceutically acceptable salt thereof, together with at least one pharmaceutically acceptable carrier, diluent or excipient for use in the inhibition of Trk activity.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancer.

In an additional embodiment the present invention provides a pharmaceutical composition comprising a compound of formula (I), or a pharmaceutically acceptable salt thereof, together with at least one pharmaceutically acceptable carrier, diluent or excipient for use in the treatment or prophylaxis of cancers (solid tumors and leukemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation.

In an additional embodiment the present invention provides a pharmaceutical composition comprising a compound of formula (I), or a pharmaceutically acceptable salt thereof, together with at least one pharmaceutically acceptable carrier, diluent or excipient for use in the production of an anti-proliferative effect in a warm-blooded animal such as man.

In an additional embodiment the present invention provides a compound of formula (I), or a pharmaceutically acceptable salt thereof, for use in the inhibition of Trk activity.

In an additional embodiment the present invention provides a compound of formula (I), or a pharmaceutically acceptable salt thereof, for use in the treatment or prophylaxis of cancer.

In an additional embodiment the present invention provides a compound of the formula (I), or a pharmaceutically acceptable salt thereof, for use in the treatment of cancer in a warm-blooded animal such as man.

In an additional embodiment the present invention provides a compound of the formula (I), or a pharmaceutically acceptable salt thereof, for use in the treatment or prophylaxis of cancers (solid tumours and leukaemia), fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases and ocular diseases with retinal vessel proliferation in a warm-blooded animal such as man.

In an additional embodiment the present invention provides a compound of formula (I), or a pharmaceutically acceptable salt thereof, for use in the production of an anti-proliferative effect.

In one embodiment where the inhibition of Trk activity is referred to particularly this refers to the inhibition of Trk A activity.

In another embodiment where the inhibition of Trk activity is referred to particularly this refers to the inhibition of Trk B activity.

Where the treatment (or prophylaxis) of cancer is referred to, particularly it refers to the treatment (or prophylaxis) of mesoblastic nephroma, mesothelioma, acute myeloblastic leukemia, acute lymphocytic leukemia, multiple myeloma, oesophageal cancer, myeloma, hepatocellular, pancreatic, cervical cancer, Ewings sarcoma, neuroblastoma, Kaposi sarcoma, ovarian cancer, breast cancer including secretory breast cancer, colorectal cancer, prostate cancer including hormone refractory prostate cancer, bladder cancer, melanoma, lung cancer—non small cell lung cancer (NSCLC), and small cell lung cancer (SCLC), gastric cancer, head and neck cancer, renal cancer, lymphoma thyroid cancer including papillary thyroid cancer, mesothelioma, leukaemia, tumours of the central and peripheral nervous system, melanoma, fibrosarcoma including congenital fibrosarcoma and osteosarcoma. More particularly it refers to prostate cancer. In addition, more particularly it refers to SCLC, NSCLC, colorectal cancer, ovarian cancer and/or breast cancer. In a further aspect it refers to hormone refractory prostate cancer.

In a further aspect of the present invention provides a process for preparing a compound of formula (I) or a pharmaceutically acceptable salt thereof which process (wherein variable groups are, unless otherwise specified, as defined in formula (I)) comprises of:

Process a) reaction of a compound of formula (II):

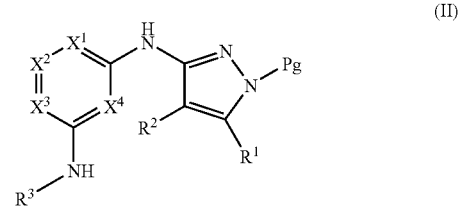

(II)

wherein Pg is a nitrogen protecting group; with a compound of formula (III):

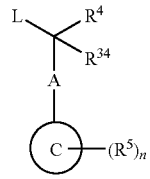 (III)

wherein L is a displaceable group;

Process b) for compounds of formula (I) wherein $R^4$ is hydroxymethyl and $R^{34}$ is hydrogen; reaction of a compound of formula (II) with an epoxide of formula (IV):

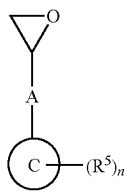 (IV)

Process c) reacting a compound of formula (V):

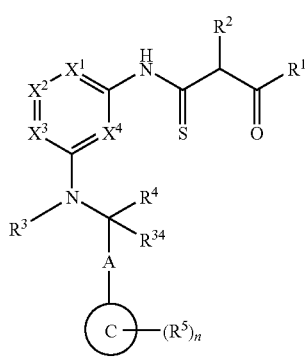 (V)

with hydrazine;

Process d) reacting a compound of formula (VI):

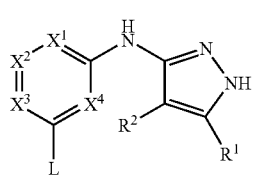 (VI)

wherein L is a displaceable group; with an amine of formula (VII):

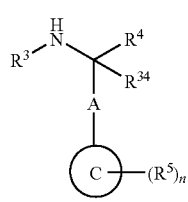 (VII)

Process e) reacting a compound of formula (VIII):

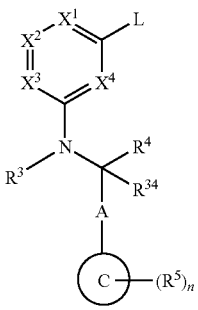 (VIII)

wherein L is a displaceable group; with an amine of formula (IX):

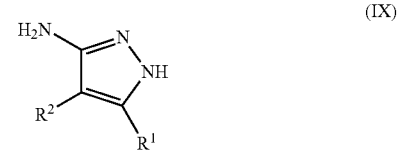 (IX)

Process f) reacting an amine of formula (X):

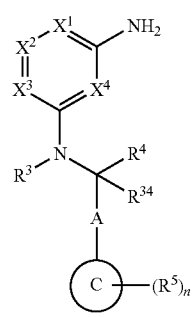 (X)

with a compound of formula (XI):

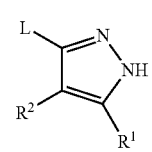 (XI)

wherein L is a displaceable group; and thereafter if necessary:
i) converting a compound of the formula (I) into another compound of the formula (I);
ii) removing any protecting groups;
iii) forming a pharmaceutically acceptable salt.

L is a displaceable group, suitable values for L are for example, a halo or sulphonyloxy group, for example a chloro, bromo, methanesulphonyloxy or toluene-4-sulphonyloxy group.

Pg is a nitrogen protecting group. Suitable values for Pg are described herein below.

Specific reaction conditions for the above reactions are as follows.

Process a) Compounds of formula (II) and (III) may be reacted together under standard nucleophilic addition reactions for example in the presence of a suitable base such as potassium carbonate and a suitable solvent such as DMF and at a temperature in the range from 25 to 100° C.

Compounds of the formula (II) may be prepared according to Scheme 1:

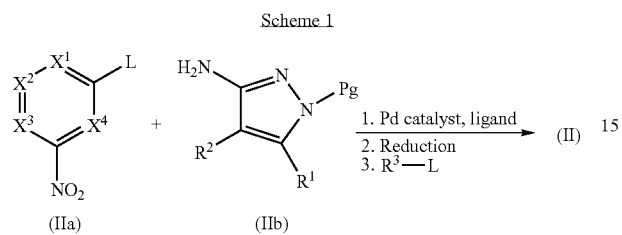

wherein Pg is a nitrogen protecting group. Suitable values for Pg are defined below; and wherein L is a displaceable group as defined above.

Compounds of formula (III), (IIa) and (IIb) are commercially available compounds, or they are known in the literature, or they are prepared by standard processes known in the art.

Process b) Compounds of formula (II) and (IV) may be reacted together under epoxide ring opening reaction conditions for example in the presence of a suitable catalyst such as $LiClO_4$, $NaClO_4$, $Mg(ClO_4)_2$ and a suitable solvent such as $CH_3CN$ and at a temperature in the range from 25 to 80° C.

Compounds of formula (IV) are commercially available compounds, or they are known in the literature, or they are prepared by standard processes known in the art.

Process c) The s reaction may be carried out in a suitable solvent, for example, an alcohol such as ethanol or butanol at a temperature in the range from 50-120° C., in particular in the range from 70-100° C.

Compounds of the formula (V) may be prepared according to Scheme 2:

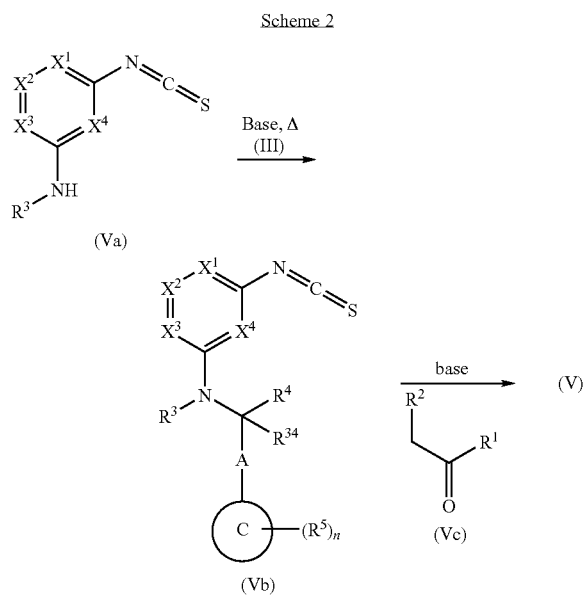

Compounds of the formula (Va) are commercially available compounds, or they are known in the literature, or they are prepared by standard processes known in the art.

Process d) Compounds of formula (VI) and (VII) may be reacted together under the conditions listed in Process a).

Compounds of formula (VI) may be prepared according to Scheme 3:

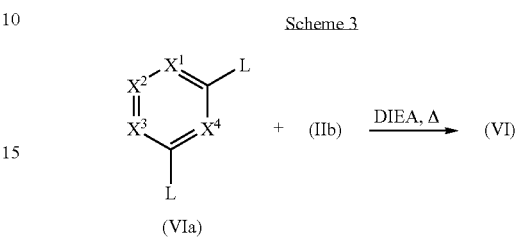

wherein L is a displaceable group as defined herein above.

Compounds of the formula (VIa) and (VII) are commercially available compounds, or they are known in the literature, or they are prepared by standard processes known in the art.

Process e) Compounds of formula (VIII) and (IX) may be reacted together under the conditions listed in Process a).

Compounds of formula (VIII) may be prepared according to Scheme 4:

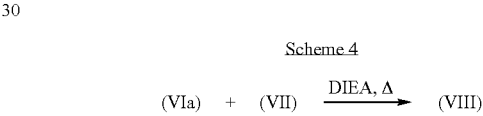

Compounds of the formula (IX) are commercially available compounds, or they are known in the literature, or they are prepared by standard processes known in the art.

Process f) Compounds of formula (X) and (XI) may be reacted together under the conditions listed in Process a).

Compounds of formula (X) may be prepared according to Scheme 5:

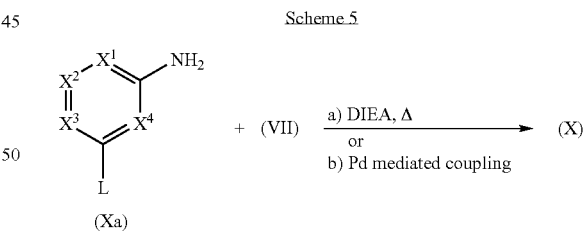

wherein L is a displaceable group as defined herein above.

Compounds of the formula (Xa) and (XI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Definitions

In this specification the term "alkyl" includes both straight and branched chain alkyl groups but references to individual alkyl groups such as "propyl" are specific for the straight chain version only. For example, "$C_{1-6}$alkyl" and "$C_{1-4}$alkyl" include methyl, ethyl, propyl, isopropyl and t-butyl. However, references to individual alkyl groups such as 'propyl' are specific for the straight-chained version only and references to individual branched chain alkyl groups such as 'isopropyl' are specific for the branched-chain version only. A similar convention applies to other radicals. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 4-12 atoms of which at least one atom is chosen from nitrogen, sulphur or oxygen, which may, unless otherwise specified, be carbon or nitrogen linked, wherein a —$CH_2$— group can optionally be replaced by a —C(O)—, and a ring sulphur atom may be optionally oxidised to form the S-oxides. Examples and suitable values of the term "heterocyclyl" are morpholino, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Further examples and suitable values of the term "heterocyclyl" are morpholino, piperazinyl and pyrrolidinyl. In one aspect of the invention a "heterocyclyl" is a saturated, partially saturated or unsaturated, mono or bicyclic ring containing 5 or 6 atoms of which at least one atom is chosen from nitrogen, sulphur or oxygen, it may, unless otherwise specified, be carbon or nitrogen linked, a —$CH_2$— group can optionally be replaced by a —C(O)— and a ring sulphur atom may be optionally oxidised to form the S-oxides. Further examples and suitable values of the term "heterocyclyl" are tetrahydrofuranyl, furanyl, pyrrolyl, isoxazolyl, piperidinyl, thienyl, pyridyl, tetrahydro-2H-thiopyranyl, morpholino and 2-oxopyrrolidinyl.

A "carbocyclyl" is a saturated, partially saturated or unsaturated, mono or bicyclic carbon ring that contains 3-12 atoms; wherein a —$CH_2$— group can optionally be replaced by a —C(O)—. Particularly "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl.

Where "one of $X^1$, $X^2$, $X^3$ and $X^4$ is =N—, the other three are independently selected from =$CR^8$—, =$CR^9$— and =$CR^{10}$—" it is to be understood that this means one of $X^1$, $X^2$, $X^3$ and $X^4$ is =N—, one of the other three is =$CR^8$—, one of the remaining two is =$CR^9$— and the last is =$CR^{10}$—. For example the scenario wherein $X^1$ is =N—, $X^2$ is =$CR^8$—, $X^3$ is =$CR^9$— and $X^4$ is =$CR^{10}$— is embraced by this definition as is $X^3$ is =N—, $X^1$ is =$CR^8$—, $X^2$ is =$CR^9$— and $X^4$ is =$CR^{10}$—. The ring containing $X^1$, $X^2$, $X^3$ and $X^4$ is thus a pyridine ring.

The term "$C_{m-n}$" or "$C_{m-n}$ group" used alone or as a prefix, refers to any group having m to n carbon atoms.

The term "optionally substituted" refers to either groups, structures, or molecules that are substituted and those that are not substituted.

An example of "$C_{1-6}$alkanoyloxy" is acetoxy. Examples of "$C_{1-6}$alkoxycarbonyl" include $C_{1-4}$alkoxycarbonyl, methoxycarbonyl, ethoxycarbonyl, n- and t-butoxycarbonyl. Examples of "$C_{1-6}$alkoxy" include $C_{1-4}$alkoxy, $C_{1-3}$alkoxy, methoxy, ethoxy and propoxy. Examples of "$C_{1-6}$alkoxyimino" include $C_{1-4}$alkoxyimino, $C_{1-3}$alkoxyimino, methoxyimino, ethoxyimino and propoxyimino. Examples of "$C_{1-6}$alkanoylamino" include formamido, acetamido and propionylamino. Examples of "$C_{1-6}$alkylS(O)$_a$ wherein a is 0 to 2" include $C_{1-4}$alkylsulphonyl, methylthio, ethylthio, methylsulphinyl, ethylsulphinyl, mesyl and ethylsulphonyl. Examples of "$C_{1-6}$alkylthio" include methylthio and ethylthio. Examples of "$C_{1-6}$alkylsulphonylamino" include methylsulphonylamino and ethylsulphsulphonylamino. Examples of "$C_{1-6}$alkanoyl" include $C_{1-4}$alkanoyl, formyl, propionyl and acetyl. Examples of "N—($C_{1-6}$alkyl)amino" include methylamino and ethylamino. Examples of "N,N—($C_{1-6}$alkyl)$_2$amino" include di-N-methylamino, di-(N-ethyl) amino and N-ethyl-N-methylamino. Examples of "$C_{2-6}$alkenyl" are vinyl, alkyl and 1-propenyl. Examples of "$C_{2-6}$alkynyl" are ethynyl, 1-propynyl and 2-propynyl. Examples of "N—($C_{1-6}$alkyl)sulphamoyl" are N-(methyl)sulphamoyl and N-(ethyl)sulphamoyl. Examples of "N—($C_{1-6}$alkyl)$_2$sulphamoyl" are N,N-(dimethyl)sulphamoyl and N-(methyl)-N-(ethyl)sulphamoyl. Examples of "N—($C_{1-6}$alkyl)carbamoyl" are N—($C_{1-4}$alkyl)carbamoyl, methylaminocarbonyl and ethylaminocarbonyl. Examples of "N,N—($C_{1-6}$alkyl)$_2$carbamoyl" are N,N—($C_{1-4}$alkyl)$_2$carbamoyl, dimethylaminocarbonyl and methylethylaminocarbonyl. Examples of "$C_{1-6}$alkylsulphonyl-N—($C_{1-6}$alkyl)amino" include N-mesyl-N-methylamino and N-mesyl-N-isopropylamino.

"RT" or "rt" means room temperature.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

It should be noted that the pyrazoles claimed in this invention are capable to exist in different resonance structures and thus the pyrazoles claimed herein include all possible resonance structures, for example optical isomers, diastereoisomers and geometric isomers and all tautomeric forms of the compounds of the formula (I).

It is also to be understood that certain compounds of the formula (I) can exist in solvated as well as unsolvated forms such as, for example, hydrated forms. It is to be understood that the invention encompasses all such solvated forms.

Formulations

Compounds of the present invention may be administered orally, parenterally, buccal, vaginal, rectal, inhalation, insufflation, sublingually, intramuscularly, subcutaneously, topically, intranasally, intraperitoneally, intrathoracially, intravenously, epidurally, intrathecally, intracerebroventricularly and by injection into the joints.

The dosage will depend on the route of administration, the severity of the disease, age and weight of the patient and other factors normally considered by the attending physician, when determining the individual regimen and dosage level as the most appropriate for a particular patient.

An effective amount of a compound of the present invention for use in therapy of cancer is an amount sufficient to symptomatically relieve in a warm-blooded animal, particularly a human the symptoms of cancer, to slow the progression of cancer, or to reduce in patients with symptoms of cancer the risk of getting worse.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet disintegrating agents; it can also be an encapsulating material.

In powders, the carrier is a finely divided solid, which is in a mixture with the finely divided active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

Suitable carriers include magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bicarbonate, bisulfate, butyrate, camphorate, camphorsulfonate, choline, citrate, cyclohexyl sulfamate, diethylenediamine, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, meglumine, 2-naphthalenesulfonate, nitrate, oxalate, pamoate, persulfate, phenylacetate, phosphate, diphosphate, picrate, pivalate, propionate, quinate, salicylate, stearate, succinate, sulfamate, sulfanilate, sulfate, tartrate, tosylate (p-toluenesulfonate), trifluoroacetate, and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Nontoxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

In addition to the compounds of the present invention, the pharmaceutical composition of this invention may also contain, or be co-administered (simultaneously or sequentially) with, one or more pharmacological agents of value in treating one or more disease conditions referred to herein.

The term composition is intended to include the formulation of the active component or a pharmaceutically acceptable salt with a pharmaceutically acceptable carrier. For example this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

Liquid form compositions include solutions, suspensions, and emulsions. Sterile water or water-propylene glycol solutions of the active compounds may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms.

Combinations

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as
N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and
6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

(x) other treatment regimes including: dexamethasone, proteasome inhibitors (including bortezomib), isotretinoin (13-cis retinoic acid), thalidomide, revemid, Rituxamab, ALIMTA, Cephalon's kinase inhibitors CEP-701 and CEP-2563, anti-Trk or anti-NGF monoclonal antibodies, targeted radiation therapy with 131I-metaiodobenzylguanidine (131I-MIBG), anti-G(D2) monoclonal antibody therapy with or without granulocyte-macrophage colony-stimulating factor (GM-CSF) following chemotherapy.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically-active agent within its approved dosage range.

Synthesis

The compounds, or pharmaceutically acceptable salts thereof, of the present invention can be prepared in a number of ways well known to one skilled in the art of organic synthesis. The compounds, or pharmaceutically acceptable salts thereof, of the present invention can be synthesized using the methods described below, together with synthetic methods known in the art of synthetic organic chemistry, or variations thereon as appreciated by those skilled in the art. Such methods include, but are not limited to, those described below. All references cited herein are hereby incorporated in their entirety by reference.

The novel compounds, or pharmaceutically acceptable salts thereof, of this invention may be prepared using the reactions and techniques described herein. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

EXAMPLES

The invention will now be further described with reference to the following illustrative examples in which, unless stated otherwise:

(i) temperatures are given in degrees Celsius (° C.); operations are carried out at room temperature or ambient temperature, that is, in a range of 18-25° C.;

(ii) organic solutions were dried over anhydrous magnesium sulfate; evaporation of organic solvent was carried out using a rotary evaporator under reduced pressure (4.5-30 mmHg) with a bath temperature of up to 60° C.;

(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;

(v) final products have satisfactory proton nuclear magnetic resonance (NMR) spectra and/or mass spectra data;

(vi) yields are given for illustration only and are not necessarily those which can be obtained by diligent process development; preparations were repeated if more material was required;

(vii) when given, NMR data is in the form of delta values for major diagnostic protons, given in part per million (ppm) relative to tetramethylsilane (TMS) as an internal standard, determined at 300 MHz in DMSO-$d_6$ unless otherwise stated;

(viii) chemical symbols have their usual meanings;

(ix) solvent ratio was given in volume:volume (v/v) terms.

(x) the following abbreviations have been used:

| | |
|---|---|
| EtOAc | ethyl acetate; |
| ether | diethyl ether; |
| EtOH | ethanol; |
| THF | tetrahydrofuran; |
| TFP | tetrafluorophenyl; |
| DIEA | diisopropylethylamine; |
| DMAP | 4-dimethylaminopyridine; |
| NMP | N-methylpyridinone; |
| MTBE | methyl tert-butyl ether; |
| DMF | N,N-dimethylformamide; |
| HBTU | 2-(1H-benzotriazole-1-yl)-1,1,3,3-tetramethyluronium hexafluorophosphate; |
| DCE | dichloroethane; |
| TFP resin | tetrafluorophenol resin; |
| MeOH | methanol; and |
| DCM | dichloromethane. |

Example 1

(S)-6-(5-Cyclopropyl-1H-pyrazol-3-ylamino)-5-fluoro-2-(1-(4-fluorophenyl)ethylamino) nicotinonitrile A portion of 2-chloro-6-(5-cyclopropyl-1H-pyrazol-3-ylamino)-5-fluoronicotinonitrile (Method 1; 0.8 g, 2.8 mmol) and (S)-1-(4-fluorophenyl)ethanamine (0.8 g, 5.6 mmol) were added to a solution of n-BuOH (4 ml) and DIEA (0.5 g, 3.7 mmol) in a sealed tube. The reaction was heated to 140° C. for 48 hrs, then cooled to 25° C. and concentrated. The resulting residue was purified by column chromatography (DCM-MeOH=50:1) to give the title compound (0.55 g, 50%). $^1$H NMR (400 MHz, CDCl$_3$) δ 8.44 (br s, 1H), 7.37-7.33 (m, 2H), 7.27 (d, J=9.6 Hz, 1H), 7.07-7.03 (m, 2H), 6.11 (s, 1H), 5.24-5.20 (m, 2H), 1.87-1.83 (m, 1H), 1.60 (d, J=6.2 Hz, 3H), 1.01-0.98 (m, 2H), 0.79-0.65 (m, 2H). MS: Calcd.: 380. Found: [M+H]$^+$ 381.

Example 2

(S)-6-(5-Cyclopropyl-1H-pyrazol-3-ylamino)-5-fluoro-2-(1-(4-fluorophenyl)ethylamino) nicotinamide To a solution of (S)-6-(5-cyclopropyl-1H-pyrazol-3-ylamino)-5-fluoro-2-(1-(4-fluorophenyl)ethylamino)nicotinonitrile (Example 1; 0.5 g, 1.3 mmol) in MeOH (50 ml), was added a 25% aqueous solution (2 ml) of KOH (400 mg) at 25° C., followed by the addition of 0.1 ml of 30% $H_2O_2$. The resulting dark red solution was heated to 65° C. for 1 h, cooled to 25° C., and concentrated. The resulting residue was dissolved in EtOAc (50 ml), washed with water (30 ml), dried, filtered and concentrated. The resulting solid was purified by column chromatography (DCM-MeOH=30:1) to give the title compound (0.30 g, 60%). $^1$H NMR (400 MHz, $CDCl_3$) δ 9.06 (d, J=7.0 Hz, 1H), 7.90 (br s, 1H), 7.35-7.32 (m, 2H), 7.25 (d, J=7.2 Hz, 1H), 7.00-6.95 (m, 2H), 6.00 (br s, 1H), 5.66 (br s, 2H), 5.21-5.17 (m, 1H), 1.86-1.82 (m, 1H), 1.54 (d, J=6.8 Hz, 3H), 0.96-0.92 (m, 2H), 0.69-0.67 (m, 2H). MS: Calcd.: 398. Found: $[M+H]^+$ 399.

Example 3

(S)-3-(Aminomethyl)-$N^6$-(5-cyclopropyl-1H-pyrazol-3-yl)-5-fluoro-$N^2$-(1-(4-fluorophenyl) ethyl)pyridine-2,6-diamine To a MeOH solution (5 ml) was added (S)-6-(5-cyclopropyl-1H-pyrazol-3-ylamino) -5-fluoro-2-(1-(4-fluorophenyl) ethylamino)nicotinonitrile (Example 1; 0.15 g, 0.4 mmol), conc. HCl (0.1 ml), and Pd (10 wt. %, dry basis, on activated carbon, 0.12 g). The mixture was then flushed with $N_2$, evacuated, and then placed under 40 psi of $H_2$ for 6 hrs. The reaction was then evacuated, flushed with $N_2$, filtered, washed with MeOH (3×30 ml), and concentrated. The resulting solid was dissolved in the mixture of DCM-MeOH (50:1, 100 ml), and a saturated aqueous solution of $Na_2CO_3$ (100 ml) was added, and the mixture was shaken vigorously for 30 min. The layers were then allowed to separate, and the aqueous layer was extracted with DCM (3×100 ml). The combined organic layers were dried, filtered and concentrated. The resulting solid was purified by column chromatography (DCM-MeOH=9:1) to give the title compound (0.09 g, 58%). $^1$H NMR (400 MHz, $CD_3OD$) δ 7.42-7.38 (m, 2H), 7.15 (d, J=11. Hz, 1H), 7.02-6.97 (m, 2H), 5.15-5.08 (m, 1H), 3.74 (s, 2H), 1.88-1.81 (m, 1H), 1.54 (d, J=7.0 Hz, 3H), 0.93-0.92 (m, 2H), 0.67-0.63 (m, 2H). MS: Calcd.: 384. Found: $[M+H]^+$ 385.

Example 4

(S)—N-((6-(5-Cyclopropyl-1H-pyrazol-3-ylamino)-5-fluoro-2-(1-(4-fluorophenyl)ethylamino) pyridin-3-yl)methyl)acetamide A round bottom flask was charged with (S)-3-(aminomethyl)-$N^6$-(5-cyclopropyl-1H-pyrazol -3-yl)-5-fluoro-$N^2$-(1-(4-fluorophenyl)ethyl)pyridine-2,6-diamine (Example 3; 0.08 g, 0.2 mmol) and acetic acid loaded TFP resin (1.4 mmol/g loading, 0.2 mmol) in mixture of THF-DCM (1:1, 3 ml) at 0° C. The resulting solution was shaken vigorously at 0° C. for 45 min and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.045 g, 50%). $^1$H NMR (400 MHz, $CD_3OD$) δ 7.34-7.33 (m, 2H), 7.11 (d, J=10.7 Hz, 1H), 7.01-6.97 (m, 2H), 5.14-5.04 (m, 1H), 4.30-4.17 (m, 2H), 1.99 (s, 3H), 1.88-1.81 (m, 1H), 1.50 (d, J=6.8 Hz, 3H), 0.94-0.92 (m, 2H), 0.67-0.63 (m, 2H). MS: Calcd.: 426. Found: $[M+H]^+$ 427.

Example 5

(S)—N-((6-(5-Cyclopropyl-1H-pyrazol-3-ylamino)-5-fluoro-2-(1-(4-fluoro-Phenyl)ethylamino) pyridin-3-yl)methyl)methanesulfonamide A round bottom flask was charged with (S)-3-(aminomethyl)-$N^6$-(5-cyclopropyl-1H-pyrazol -3-yl)-5-fluoro-$N^2$-(1-(4-fluorophenyl)ethyl)pyridine-2,6-diamine (Example 3; 0.025 g, 0.065 mmol), methanesulfonic acid loaded TFP resin (0.9 mmol/g loading, 0.065 mmol), DIEA (0.017 g, 0.13 mmol), DMAP (0.09 g, 0.072 mmol), and THF (5 ml). The resulting solution was shaken vigorously at 60° C. for 8 hrs. The reaction was filtered and the resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.016 g, 53%). $^1$H NMR (400 MHz, $CD_3OD$) δ 7.42-7.39 (m, 2H), 7.14 (d, J=10.7 Hz, 1H), 7.01-6.97 (m, 2H), 5.16-5.09 (m, 1H), 4.15-4.06 (m, 2H), 2.99 (s, 3H), 1.88-1.83 (m, 1H), 1.52 (d, J=6.8 Hz, 3H), 0.95-0.93 (m, 2H), 0.66-0.64 (m, 2H). MS: Calcd.: 462. Found: $[M+H]^+$ 463.

Example 6

(R)-6-(5-Cyclopropyl-1H-pyrazol-3-ylamino)-5-fluoro-2-(1-(4-fluorophenyl)-2-hydroxyethylamino) nicotinonitrile 2-Chloro-6-(5-cyclopropyl-1H-pyrazol-3-ylamino)-5-fluoronicotinonitrile (Method 1; 0.5 g, 1.8 mmol) and (R)-2-amino-2-(4-fluorophenyl)ethanol (0.6 g, 3.6 mmol) were added to a solution of n-BuOH (4 ml) and DIEA (0.3 g, 2.3 mmol) in a sealed tube. The reaction was heated to 140° C. for 48 hrs, then cooled to 25° C. and concentrated. The resulting residue was purified by column chromatography (DCM-MeOH=80:1) to give the title compound (0.3 g, 40%). $^1$H NMR (400 MHz, $CD_3OD$) δ 7.37-7.35 (m, 3H), 7.05-7.00 (m, 2H), 5.99 (s, 1H), 5.20-5.11 (m, 1H), 3.90-3.77 (m, 2H), 1.90-1.86 (m, 1H), 1.05-0.96 (m, 2H), 0.73-0.66 (m, 2H). MS: Calcd.: 396. Found: $[M+H]^+$ 397.

Example 7

(R)-6-(5-Cyclopropyl-1H-pyrazol-3-ylamino)-5-fluoro-2-(1-(4-fluorophenyl)-2-hydroxyethylamino) nicotinamide (R)-6-(5-Cyclopropyl-1H-pyrazol-3-ylamino)-5-fluoro-2-(1-(4-fluorophenyl)-2-hydroxyethylamino)nicotinonitrile (Example 6; 0.07 g, 0.2 mmol), was placed in MeOH (5 ml) at 25° C. A 25% aqueous solution (0.2 ml) of KOH (50 mg) was then added, followed by the addition of 0.05 ml of 30% $H_2O_2$. The resulting dark red solution was heated to 65° C. for 1 h, cooled to 25° C., and concentrated. The resulting residue was dissolved in EtOAc (50 ml), washed with water (30 ml), dried, filtered, and concentrated. The resulting solid was purified by column chromatography (DCM-MeOH=30:1) to give the title compound (0.065 g, 90%). $^1$H NMR (400 MHz, $CD_3OD$) δ 7.69 (d, J=12.1 Hz, 1H), 7.39-7.36 (m, 2H), 7.04-7.00 (m, 2H), 5.94 (s, 1H), 5.22-5.16 (m, 1H), 3.87-3.75 (m, 2H), 1.91-1.84 (m, 1H), 0.98-0.96 (m, 2H), 0.74-0.69 (m, 2H). MS: Calcd.: 414. Found: $[M+H]^+$ 415.

Example 8

(R)-2-(3-(Aminomethyl)-6-(5-cyclopropyl-1H-pyrazol-3-ylamino)-5-fluoropyridin-2-ylamino)-2-(4-fluorophenyl)ethanol The mixture of (R)-6-(5-cyclopropyl-1H-pyrazol-3-ylamino)-5-fluoro-2-(1-(4-fluorophenyl)-2-hydroxyethylamino)nicotinonitrile (Example 6; 0.13 g, 0.33 mmol), conc. HCl (0.1 ml), and Pd (10 wt. %, dry basis, on activated carbon, 0.12 g) in MeOH (5 ml) was flushed with $N_2$, evacuated, and then placed under $H_2$ (40 psi) for 6 hrs. The reaction was then evacuated, flushed with $N_2$, filtered, washed with MeOH (3×30 ml), and concentrated. The resulting solid was dissolved in the mixture of DCM-MeOH (50:1, 100 ml), and a saturated aqueous solution of $Na_2CO_3$ (100 ml) was added. The mixture was shaken vigorously for 30 min and allowed to separate. The aqueous layer was extracted with DCM (3×100 ml). The combined organic layer was dried, filtered and concentrated. The resulting solid was purified by reverse-phase column chromatography (5-50% $CH_3CN$ in $H_2O$ over 400 ml) to give the title compound (0.074, 57%). $^1$H NMR (400 MHz, $CD_3OD$) δ 7.45-7.42 (m, 2H), 7.17 (d, J=11.1 Hz, 1H), 7.04-7.00 (m, 2H), 5.72 (br s, 1H), 5.18-5.08 (m, 1H), 3.89-3.72 (m, 4H), 1.87-1.83 (m, 1H), 0.94-0.92 (m, 2H), 0.69-0.65 (m, 2H). MS: Calcd.: 400. Found: $[M+H]^+$ 401.

Example 9

(R)—N-((6-(5-Cyclopropyl-1H-pyrazol-3-ylamino)-5-fluoro-2-(1-(4-fluorophenyl)-2-hydroxyethylamino)pyridin-3-yl)methyl)acetamide (R)-2-(3-(Aminomethyl)-6-(5-cyclopropyl-1H-pyrazol-3-ylamino)-5-fluoropyridin-2-ylamino)-2-(4-fluorophenyl)ethanol (Example 8; 0.034 g, 0.085 mmol) and acetic acid loaded TFP resin (1.4 mmol/g loading, 0.085 mmol) were placed in a THF-DCM solution (1:1, 3 ml) at 0° C. The resulting suspension was shaken vigorously at 0° C. for 45 min. The reaction was filtered and the resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.018 g, 48%). $^1$H NMR (400 MHz, $CD_3OD$) δ 7.42-7.36 (m, 2H), 7.12 (d, J=9.6 Hz, 1H), 7.04-6.99 (m, 2H), 6.09 (br s, 1H), 5.19-5.02 (m, 1H), 4.36-4.17 (m, 2H), 3.83-3.71 (m, 2H), 1.99 (s, 3H), 1.88-1.83 (m, 1H), 0.98-0.87 (m, 2H), 0.72-0.66 (m, 2H). MS: Calcd.: 442. Found: $[M+H]^+$ 443.

Example 10

(R)—N-((6-(5-Cyclopropyl-1H-pyrazol-3-ylamino)-5-fluoro-2-(1-(4-fluorophenyl)-2-hydroxyethylamino)pyridin-3-yl)methyl)methanesulfonamide A round bottom flask was charged with (R)-2-(3-(aminomethyl)-6-(5-cyclopropyl-1H-pyrazol-3-ylamino)-5-fluoropyridin-2-ylamino)-2-(4-fluorophenyl)ethanol (Example 8; 0.20 g, 0.50 mmol), methanesulfonic acid loaded TFP resin (0.9 mmol/g loading, 0.50 mmol), DIEA (0.13 g, 1.00 mmol), DMAP (0.067 g, 0.067 mmol), and THF (10 ml). The resulting solution was shaken vigorously at 60° C. for 8 hrs. The reaction was filtered and the resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.075 g, 31%). $^1$H NMR (400 MHz, $CD_3OD$) δ 7.50-7.41 (m, 2H), 7.15 (d, J=9.1 Hz, 1H), 7.04-7.00 (m, 2H), 6.09 (br s, 1H), 5.22-5.03 (m, 1H), 4.20-4.07 (m, 2H), 3.86-3.74 (m, 2H), 2.98 (s, 3H), 1.89-1.85 (m, 1H), 1.04-0.92 (m, 2H), 0.78-0.66 (m, 2H). MS: Calcd.: 478; Found: $[M+H]^+$ 479.

Example 11

(R)-5-Fluoro-2-(1-(4-fluorophenyl)-2-hydroxyethylamino)-6-(5-isopropoxy-1H-pyrazol-3-ylamino)nicotinonitrile 2-Chloro-5-fluoro-6-(5-isopropoxy-1H-pyrazol-3-ylamino)nicotinonitrile (Method 2; 1.6 g, 5.0 mmol) and (R)-2-amino-2-(4-fluorophenyl)ethanol (2.0 g, 11.0 mmol) were added to a solution of n-BuOH (8 ml) and DIEA (0.8 g, 6.0 mmol) in a sealed tube. The reaction was heated to 135° C. for 72 hrs, cooled to 25° C., and concentrated. The resulting residue was purified by column chromatography (DCM-MeOH=50:1) to give the title compound (0.7 g, 31%). $^1$H NMR (400 MHz, $CD_3OD$) δ 7.49 (d, J=9.5 Hz, 1H), 7.41-7.38 (m, 2H), 7.07-7.02 (m, 2H), 5.40 (s, 1H), 5.10-5.01 (m, 1H), 4.62-4.55 (m, 1H), 3.91-3.79 (m, 2H), 1.33-1.31 (m, 6H). MS: Calcd.: 414. Found: $[M+H]^+$ 415.

Example 12

(R)-5-Fluoro-2-(1-(4-fluorophenyl)-2-hydroxyethylamino)-6-(5-isopropoxy-1H-pyrazol-3-ylamino)nicotinamide (R)-5-Fluoro-2-(1-(4-fluorophenyl)-2-hydroxyethylamino)-6-(5-isopropoxy-1H-pyrazol-3-ylamino)nicotinonitrile (Example 11; 0.06 g, 0.1 mmol) was placed in MeOH (5 ml) at 25° C. A 25% aqueous solution (0.2 ml) of KOH (0.05 g, 0.7 mmol) was then added, followed by the addition of 0.05 ml of 30% $H_2O_2$. The resulting dark red solution was heated to 65° C. for 1 h, cooled to 25° C., and concentrated. The resulting residue was dissolved in EtOAc (50 ml), washed with water (30 ml), dried, filtered, and concentrated. The resulting solid was purified by column chromatography (DCM-MeOH=30:1) to give the title compound (0.037 g, 60%). $^1$H NMR (400 MHz, $CD_3OD$) δ 7.75 (d, J=11.9 Hz, 1H), 7.43-7.39 (m, 2H), 7.06-7.02 (m, 2H), 5.37 (br s, 1H), 5.10-5.02 (m, 1H), 4.60-4.54 (m, 1H), 3.90-3.86 (m, 1H), 3.79-3.74 (m, 1H), 1.32 (d, J=6.0 Hz, 6H). MS: Calcd.: 432. Found: $[M+H]^+$ 433.

Example 13

(R)-2-(3-(Aminomethyl)-5-fluoro-6-(5-isopropoxy-1H-pyrazol-3-ylamino)pyridin-2-ylamino)-2-(4-fluorophenyl)ethanol A solution of (R)-5-fluoro-2-(1-(4-fluorophenyl)-2-hydroxyethylamino)-6-(5-isopropoxy-1H-pyrazol-3-ylamino)nicotinonitrile (Example 11; 0.60 g, 1.44 mmol), conc. HCl (0.3 ml), and Pd (10 wt. %, dry basis, on activated carbon, 0.3 g) in MeOH (8 ml) was flushed with $N_2$, evacuated, and then placed under of $H_2$ (40 psi) for 6 hrs. The reaction was then evacuated, flushed with $N_2$, filtered, washed with MeOH (3×30 ml), and concentrated. The resulting solid was dissolved in the mixture of DCM-MeOH (50:1, 100 ml) and treated with a saturated aqueous $Na_2CO_3$ solution (100 ml).

The resulting mixture was shaken vigorously for 30 min and allowed to separate. The aqueous layer was extracted with DCM (3×100 ml). The combined organic layers were dried, filtered and concentrated. The resulting solid was purified by reverse-phase column chromatography (5-50% $CH_3CN$ in $H_2O$ over 400 ml) to give the title compound (0.40 g, 66%). $^1H$ NMR (400 MHz, $CD_3OD$) δ 7.47-7.44 (m, 2H), 7.37 (d, J=10.7 Hz, 1H), 7.06-7.02 (m, 2H), 5.10-5.06 (m, 1H), 4.57-4.51 (m, 1H), 4.28 (d, J=14.2 Hz, 1H), 4.07 (d, J=14.2 Hz, 1H), 3.92-3.80 (m, 2H), 1.32 (d, J=3.7 Hz, 6H). MS: Calcd.: 418. Found: $[M+H]^+$ 419.

Example 14

(R)—N-((5-Fluoro-2-(1-(4-fluorophenyl)-2-hydroxyethylamino)-6-(5-isopropoxy-1H-pyrazol-3-ylamino)pyridin-3-yl)methyl)acetamide (R)-2-(3-(Aminomethyl)-5-fluoro-6-(5-isopropoxy-1H-pyrazol-3-ylamino)pyridin-2-ylamino)-2-(4-fluorophenyl)ethanol (Example 13; 0.175 g, 0.42 mmol) and acetic acid loaded TFP resin (1.4 mmol/g loading, 0.42 mmol) were placed in a THF-DCM solution (1:1, 5 ml) at 0° C. The resulting solution was shaken vigorously at 0° C. for 45 min and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.075 g, 39%). $^1H$ NMR (400 MHz, $CD_3OD$) δ 7.42-7.39 (m, 2H), 7.17 (d, J=10.7 Hz, 1H), 7.05-7.01 (m, 2H), 5.26 (s, 1H), 5.02-4.95 (m, 1H), 4.55-4.53 (m, 1H), 4.36 (d, J=15.0 Hz, 1H), 4.22 (d, J=15.0 Hz, 1H), 3.84-3.72 (m, 2H), 2.01 (s, 3H), 1.31 (d, J=6.0 Hz, 6H). MS: Calcd.: 460. Found: $[M+H]^+$ 461.

Example 15

(R)—N-((5-Fluoro-2-(1-(4-fluorophenyl)-2-hydroxyethylamino)-6-(5-isopropoxy-1H-pyrazol-3-ylamino)pyridin-3-yl)methyl)methanesulfonamide A round bottom flask was charged with (R)-2-(3-(aminomethyl)-5-fluoro-6-(5-isopropoxy-1H-pyrazol-3-ylamino)pyridin-2-ylamino)-2-(4-fluorophenyl)ethanol (Example 13; 0.10 g, 0.24 mmol), methanesulfonic acid loaded TFP resin (0.9 mmol/g loading, 0.24 mmol), DIEA (0.062 g, 0.48 mmol), DMAP (0.032 g, 0.26 mmol), and THF (5 ml). The resulting suspension was shaken vigorously at 60° C. for 8 hrs and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.075 g, 63%). $^1H$ NMR (400 MHz, $CD_3OD$) δ 7.48-7.45 (m, 2H), 7.20 (d, J=10.9 Hz, 1H), 7.05-7.01 (m, 2H), 5.30 (s, 1H), 5.04-5.01 (m, 1H), 4.56-4.53 (m, 1H), 4.20 (d, J=14.4 Hz, 1H), 4.12 (d, J=14.4 Hz, 1H), 3.86-3.73 (m, 2H), 3.01 (s, 3H), 1.32 (d, J=6.0 Hz, 3H). MS: Calcd.: 496. Found: $[M+H]^+$ 497.

Example 16

(S)-5-Fluoro-2-(1-(4-fluorophenyl)ethylamino)-6-(5-isopropoxy-1H-pyrazol-3-ylamino)nicotinonitrile 2-Chloro-5-fluoro-6-(5-isopropoxy-1H-pyrazol-3-ylamino)nicotinonitrile (Method 2; 1.4 g, 5.0 mmol) and (S)-1-(4-fluorophenyl)ethanamine (1.0 g, 9.0 mmol) were added to a solution of n-BuOH (8 ml) and DIEA (0.8 g, 6.0 mmol) in a sealed tube. The reaction was heated to 135° C. for 48 hrs, cooled to 25° C., and concentrated. The resulting residue was purified by column chromatography (DCM-MeOH=80:1) to give the title compound (0.90 g, 48%). $^1H$ NMR (400 MHz, $CD_3OD$) δ 7.43 (d, J=10.5 Hz, 1H), 7.39-7.35 (m, 2H), 7.04-6.99 (m, 2H), 5.47 (s, 1H), 5.12-5.11 (m, 1H), 4.60-4.51 (m, 1H), 1.56 (d, J=7.0 Hz, 3H), 1.33-1.30 (m, 6H). MS: Calcd.: 398. Found: $[M+H]^+$ 399.

Example 17

(S)-5-Fluoro-2-(1-(4-fluorophenyl)ethylamino)-6-(5-isopropoxy-1H-pyrazol-3-ylamino)nicotinamide (S)-5-Fluoro-2-(1-(4-fluorophenyl)ethylamino)-6-(5-isopropoxy-1H-pyrazol-3-ylamino)nicotinonitrile (Example 16; 0.15 g, 0.38 mmol), was placed in MeOH (7 ml) at 25° C. A 25% aqueous solution (0.4 ml) of KOH (0.11 g, 1.9 mmol) was then added, followed by the addition of 0.1 ml of 30% $H_2O_2$. The resulting dark red solution was heated to 65° C. for 1 h, cooled to 25° C., and concentrated. The resulting residue was dissolved in EtOAc (50 ml), washed with water (30 ml), dried, filtered, and concentrated. The resulting solid was purified by column chromatography (DCM-MeOH=25:1) to give the title compound (0.044 g, 28%). $^1H$ NMR (400 MHz, $CD_3OD$) δ 7.75 (d, J=11.7 Hz, 1H), 7.39-7.36 (m, 2H), 7.04-7.00 (m, 2H), 5.37 (s, 1H), 5.11-5.00 (m, 1H), 4.61-4.52 (m, 1H), 1.53 (d, J=7.0 Hz, 3H), 1.31 (m, 6H). MS: Calcd.: 416. Found: $[M+H]^+$ 417.

Example 18

(S)-3-(Aminomethyl)-5-fluoro-$N^2$-(1-(4-fluorophenyl)ethyl)-$N^6$-(5-isopropoxy-1H-pyrazol-3-yl)pyridine-2,6-diamine The mixture of (S)-5-fluoro-2-(1-(4-fluorophenyl)ethylamino)-6-(5-isopropoxy-1H-pyrazol-3-ylamino)nicotinonitrile (Example 16; 0.90 g, 2.26 mmol), conc. HCl (0.3 ml), and Pd (10 wt. %, dry basis, on activated carbon, 0.55 g) in MeOH (20 ml) was flushed with $N_2$, evacuated, and then placed under $H_2$ (40 psi) for 6 hrs. The reaction was then evacuated, flushed with $N_2$, filtered, washed with MeOH (3×30 ml), and concentrated. The resulting solid was dissolved in the mixture of DCM-MeOH (50:1, 100 ml) and treated with a saturated aqueous $Na_2CO_3$ solution (100 ml). The mixture was shaken vigorously for 30 min and allowed to separate. The aqueous layer was extracted with DCM (3×100 ml). The combined organic layers were dried, filtered and concentrated. The resulting solid was purified by reverse-phase column chromatography (5-50% $CH_3CN$ in $H_2O$ over 400 ml) to give the title compound (0.7 g, 77%). $^1H$ NMR (400 MHz, $CD_3OD$) δ 7.45-7.41 (m, 2H), 7.35 (d, J=10.9 Hz, 1H), 7.03-6.99 (m, 2H), 5.35 (s, 1H), 5.09-5.04 (m, 1H), 4.55-4.49 (m, 1H), 4.18 (d, J=14.2 Hz, 1H), 4.08 (d, J=14.2 Hz, 1H), 1.59 (d, J=6.8 Hz, 3H), 1.31 (d, J=8.3 Hz, 6H). MS: Calcd.: 402. Found: $[M+H]^+$ 403.

Example 19

(S)—N-((5-Fluoro-2-(1-(4-fluorophenyl)ethylamino)-6-(5-isopropoxy-1H-pyrazol-3-ylamino)pyridin-3-yl)methyl)acetamide (S)-3-(Aminomethyl)-5-fluoro-$N^2$-(1-(4-fluorophenyl)ethyl)-$N^6$-(5-isopropoxy-1H-pyrazol-3-yl)pyridine-2,6-diamine (Example 18; 0.20 g, 0.49 mmol) and acetic acid loaded TFP resin (1.4 mmol/g loading, 0.49 mmol) were placed in a THF-DCM solution (1:1, 6 ml) at 0° C. The resulting solution was shaken vigorously at 0° C. for 45 min and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.010 g, 49%). $^1H$ NMR (400 MHz, $CD_3OD$) δ 7.37-7.34 (m, 2H), 7.14 (d, J=10.9 Hz, 1H), 7.02-6.98 (m, 2H), 5.25 (s, 1H), 4.96-4.95 (m, 1H), 4.55-4.52 (m, 1H), 4.30 (d, J=14.8 Hz, 1H), 4.21 (d, J=14.8 Hz, 1H), 2.01 (s, 3H), 1.51 (d, J=6.8 Hz, 3H), 1.31 (d, J=6.0 Hz, 6H). MS: Calcd.: 444. Found: $[M+H]^+$ 445.

Example 20

(S)—N-((5-Fluoro-2-(1-(4-fluorophenyl)ethylamino)-6-(5-isopropoxy-1H-pyrazol-3-ylamino)pyridin-3-yl)methyl)methanesulfonamide A round bottom flask was charged with (S)-3-(aminomethyl)-5-fluoro-$N^2$-(1-(4-fluorophenyl)ethyl)-$N^6$-(5-isopropoxy-1H-pyrazol-3-yl)pyridine-2,6-diamine (Example 18; 0.10 g, 0.25 mmol), methanesulfonic acid loaded TFP resin (0.9 mmol/g loading, 0.25 mmol), DIEA (0.064 g, 0.50 mmol), DMAP (0.033 g, 0.27 mmol), and THF (5 ml). The resulting suspension was shaken vigorously at 60° C. for 8 hrs and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give (0.82 g, 67%). $^1H$ NMR (400 MHz, $CD_3OD$) δ 7.44-7.41 (m, 2H), 7.17 (d, J=10.7 Hz, 1H), 7.02-6.97 (m, 2H), 5.26 (s, 1H), 5.01-4.99 (m, 1H), 4.56-4.53 (m, 1H), 4.16-4.08 (m, 1H), 3.01 (s, 3H), 1.52 (d, J=7.0 Hz, 3H), 1.31 (d, J=6.0 Hz, 6H). MS: Calcd.: 480. Found: $[M+H]^+$ 481.

Example 21

(S)-3,5-Dichloro-$N^2$-(5-cyclopropyl-1H-pyrazol-3-yl)-$N^6$-(1-(4-fluorophenyl)ethyl)pyridine-2,6-diamine 3,5,6-Trichloro-N-(5-cyclopropyl-1H-pyrazol-3-yl)pyridin-2-amine (Method 3; 0.05 g, 0.2 mmol) and (S)-1-(4-fluorophenyl)ethanamine (0.05 g, 0.4 mmol) were dissolved in NMP (2 ml) with DIEA (0.03 g, 0.22 mmol). The reaction was heated in a microwave at 200° C. for 30 min. The reaction was cooled to 25° C., quenched with water (10 ml), and extracted with MTBE (4×30 ml). The combined organic fractions were then dried, filtered, and concentrated. The resulting solid was purified by reverse-phase column chromatography (5-50% $CH_3CN$ in $H_2O$ over 400 ml) to give the title compound (0.008 g, 11%). $^1H$ NMR (400 MHz, $CD_3OD$) δ 7.41 (s, 1H), 7.33-7.30 (m, 2H), 7.02-6.98 (m, 2H), 6.03 (s, 3H), 5.17 (q, J=6.8 Hz, 1H), 2.02-1.98 (m, 1H), 1.59 (d, J=6.8 Hz, 3H), 1.21-1.65 (m, 2H), 0.86-0.82 (m, 2H). MS: Calcd.: 406. Found: $[M+H]^+$ 407.

Example 22

N-(5-Cyclopropyl-1H-pyrazol-3-yl)-N'-[(1S)-1-(4-fluorophenyl)ethyl]pyridine-2,6-diamine tert-Butyl 5-cyclopropyl-3-[(6-{[(is)-1-(4-fluorophenyl)ethyl]amino}pyridin-2-yl)amino]-1H-pyrazole-1-carboxylate (Method 21; 146 mg) was dissolved in a solution of hydrogen chloride in ether (2.0 M, 2 ml, 4 mmol) and the reaction mixture was stirred at room temperature for 4 hours. The solvent was removed and semi-prep HPLC (Gilson) purification gave the title compound (37 mg, 25%). $^1H$ NMR ($CDCl_3$) δ 0.55 (m, 2H), 0.70 (m, 2H), 1.35 (m, 3H), 1.65 (m, 1H), 4.53 (m, 2H), 4.91 (br s, 1H), 6.10 (br s, 1H), 6.70 (m, 1H), 7.00 (m, 2H), 7.25 (m, 3H).

Example 23

(S)-2-Amino-N-((6-(5-cyclopropyl-1H-pyrazol-3-ylamino)-5-fluoro-2-(1-(4-fluorophenyl)ethylamino)pyridin-3-yl)methyl)acetamide To a solution of tert-butyl (2-{[(6-[(5-cyclopropyl-1H-pyrazol-3-yl)amino]-5-fluoro -2-{[(1S)-1-(4-fluorophenyl)ethyl]amino}pyridin-3-yl)methyl]amino}-2-oxoethyl)carbamate (Method 22; 0.035 g, 0.065 mmol) in dioxane (4 ml), was added an HCl/dioxane solution (4.0 M, 30 eq.). The resulting solution was stirred at 25° C. for 3 hrs. The reaction was then concentrated, re-dissolved in MeOH (0.5 ml), and quickly treated with ether (50 ml). The resulting solid was collected to give the HCl salt of the title compound (0.025 g, 87%). $^1H$ NMR (400 MHz, $CD_3OD$) δ 7.60 (d, J=10.7 Hz, 1H), 7.47-7.44 (m, 2H), 7.07-7.03 (m, 2H), 5.78 (s, 1H), 5.04 (q, J=6.6 Hz, 1H), 4.43-4.40 (m, 2H), 3.79 (s, 2H), 2.01-1.96 (m, 1H), 1.66 (d, J=6.6 Hz, 3H), 1.17-1.13 (m, 2H), 0.82-0.81 (m, 2H). MS: Calcd.: 441. Found: $[M+H]^+$ 442.

Example 24

N-((6-(5-Cyclopropyl-1H-pyrazol-3-ylamino)-5-fluoro-2-((S)-1-(4-fluorophenyl)ethylamino)pyridin-3-ylmethyl)-5-oxopyrrolidine-2-carboxamide A round bottom flask was charged with (S)-3-(aminomethyl)-N-(5-cyclopropyl-1H-pyrazol -3-yl)-5-fluoro-$N^2$-(1-(4-fluorophenyl)ethyl)pyridine-2,6-diamine (Example 3; 0.08 g, 0.2 mmol), 5-oxopyrrolidine-2-carboxylic acid loaded TFP resin (1.4 mmol/g loading, 0.2 mmol), and a THF-DCM solution (3 ml) at 0° C. The resulting solution was shaken vigorously at 0° C. for 45 min and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.013 g, 10%). $^1H$ NMR (400 MHz, $CD_3OD$) δ 7.41-7.32 (m, 2H), 7.21-7.13 (m, 1H), 7.05-6.97 (m, 2H), 6.05 (s, 1H), 5.21-5.02 (m, 1H), 4.34-4.19 (m, 3H), 2.44-2.28 (m, 3H), 2.11-1.98 (m, 1H), 1.88-1.81 (m, 1H), 1.51 (d, J=5.2 Hz, 3H), 0.99-0.86 (m, 2H), 0.69-0.61 (m, 2H). MS: Calcd.: 495 Found: $[M+H]^+$ 496.

Example 25

$N^4$-(5-Cyclopropyl-1H-pyrazol-3-yl)-$N^2$-[(S)-1-(4-fluoro-phenyl)-ethyl]-pyridine-2,4-diamine A mixture of (2-chloro-pyridin-4-yl)-(5-cyclopropyl-1H-pyrazole-3-yl)-amine (Method 4; 0.116 g, 0.49 mmol), DIEA (0.20 ml, 1.18 mmol), and (S)-1-(4-fluoro-phenyl)-ethylamine (1.0 ml, 7.4 mmol) was heated to 160° C. in a sealed tube for 2 days. The reaction mixture was concentrated under reduced pressure and purified by reverse-phase prep HPLC (column: mC-PACK-ODS-AQ, 250×20 nm, 3.0×50 mm; 5-95% gradient MeCN (0.05% TFA) in water (0.1% TFA); flow rate: 10.0 ml/min). $^1H$ NMR (400 MHz) δ 0.696 (m, 2H), 0.958 (m, 2H), 1.49 (m, 4H), 4.75 (q, 1H), 5.60 (s, 1H), 7.19

(t, 2H), 7.29 (t, 1H), 7.42 (t, 3H), 7.6 (s, 1H), 9.89 (s, 1H). MS: Calcd.: 337. Found: [M+H]+ 338.

Example 26

(S)—$N^6$-(5-Cyclopropyl-1H-pyrazol-3-yl)-$N^2$-(1-(4-fluorophenol)ethyl)-3-nitropyridine-2,6-diamine A mixture of (S)-6-chloro-N-(1-(4-fluorophenyl)ethyl)-3-nitropyridin-2-amine (Method 5; 1.74 g, 5.88 mmol), 5-cyclopropyl-1H-pyrazol-3-amine (0.91 g, 7.36 mmol), and DIEA (1.28 ml, 7.36 mmol) in n-BuOH (10 ml) was heated in a sealed tube at 160° C. for 60 hrs. The solvent was removed under reduced pressure and the residue was purified by chromatography (hexane-EtOAc=1:1) to give the title compound as a yellow solid (1.35 g, 60%). $^1$H NMR (400 MHz) δ 12.15 (s, 1H), 10.43 (br, 1H), 9.19 (br, 1H), 8.12 (d, J=9.2 Hz, 1H), 7.45 (m, 2H), 7.17 (m, 2H), 6.25 (br, 1H), 6.14 (br, 1H), 5.45 (m, 1H), 1.87 (m, 1H), 1.60 (d, J=6.8 Hz, 3H), 0.95 (m, 2H), 0.65 (m, 2H). MS: Calcd.: 382. Found: [M+H]+ 383.

Examples 27-30

Following a similar procedure to Example 26, the following compounds were synthesized from a chloronitropyridine by reacting it with an amine.

Example 31

(S)—$N^6$-(5-Cyclopropyl-1H-pyrazol-3-yl)-$N^2$-(1-(4-fluorophenyl)ethyl)pyridine-2,3,6-triamine To a suspension of (S)—$N^6$-(5-cyclopropyl-1H-pyrazol-3-yl)-$N^2$-(1-(4-fluorophenyl)ethyl)-3-nitropyridine-2,6-diamine (Example 26; 0.40 g, 1.05 mmol) and zinc dust (0.342 g, 5.23 mmol) in MeOH-THF (1:1, 16 ml) was slowly added a saturated aqueous ammonium chloride solution (2.5 ml). The mixture was stirred at 25° C. for 1 hr, then treated with saturated ammonium acetate solution (4 ml). The resulting mixture was stirred for another 30 min. The Zn dust was removed by filtration and the cake was washed with EtOAc (20 ml). The organic layer was separated, washed with brine (10 ml), and dried over $Na_2SO_4$. Removal of the solvent gave the title compound at quantitative yield. $^1$H NMR (400 MHz) δ 11.5 (br, 1H), 7.98 (br, 1H), 7.43 (m, 2H), 7.07 (m, 2H), 6.67 (d, J=8 Hz, 1H), 6.09 (s, 1H), 5.63-5.70 (m, 2H), 5.19 (m, 1H), 4.04 (br, 2H), 1.77 (m, 1H), 1.46 (d, J=6.8 Hz, 3H), 0.85 (m, 2H), 0.59 (m, 2H). MS: Calcd.: 352. Found: [M+H]+ 353.

Examples 32-35

Following a similar procedure to Example 31, the following compounds were synthesized from a nitropyridine by reacting it with zinc dust.

| Ex | Product | NMR/MS | Amine | SM |
|---|---|---|---|---|
| 27 | $N^6$-(5-Cyclopropyl-1H-pyrazol-3-yl)-$N^2$-(4-fluorobenzyl)-3-nitropyridine-2,6-diamine | (400 MHz) 12.10 (br s, 1H), 10.40 (br s, 1H), 9.43 (br, 1H), 8.09 (d, J = 6.8 Hz, 1H), 7.37 (m, 2H), 7.15 (m, 2H), 6.24 (br s, 1H), 6.04 (br s, 1H), 4.80 (d, J = 5.6 Hz, 2H), 1.772 (m, 1H), 0.85 (m, 2H), 0.46 (m, 2H). MS: Calcd.: 368; Found: [M + H]+ 369 | 5-cyclopropyl-1H-pyrazol-3-amine | Method 6 |
| 28 | (2R)-2-({6-[(5-Cyclopropyl-1H-pyrazol-3-yl)amino]-3-nitropyridin-2-yl}amino)-2-(4-fluorophenyl)ethanol | (400 MHz) 12.10 (s, 1H), 10.39 (br s, 1H), 9.57 (br s, 1H), 8.11 (d, J = 9.2 Hz, 1H), 7.28 (m, 2H), 7.15 (m, 2H), 6.23 (br s, 1H), 5.76 (s, 1H), 5.35 (br s, 1H), 5.19 (t, J = 4.8 Hz, 1H), 3.86 (m, 1H), 3.75 (m, 1H), 1.87 (m, 1H), 0.95 (m, 2H), 0.64 (m, 2H). MS: Calcd.: 398; Found: [M + H]+ 399 | 5-cyclopropyl-1H-pyrazol-3-amine | Method 7 |
| 29 | 2-({6-[(5-Cyclopropyl-1H-pyrazol-3-yl)amino]-3-nitropyridin-2-yl}amino)-2-(4-fluorophenyl)propane-1,3-diol | (400 MHz) 11.94 (s, 1H), 10.15 (br s, 1H), 9.85 (s, 1H), 8.12 (d, J = 9.2 Hz, 1H), 7.40 (m, 2H), 7.13 (m, 2H), 6.19 (br s, 1H), 2.86 (br s, 2H), 4.44 (m, 4H), 1.65 (m, 1H), 0.87 (m, 2H), 0.47 (m, 2H). MS: Calcd.: 428; Found: [M + H]+ 429. | 5-cyclopropyl-1H-pyrazol-3-amine | Method 8 |
| 30 | $N^6$-(5-Cyclopropyl-1H-pyrazol-3-yl)-$N^2$-[(1R)-1-(4-fluorophenyl)ethyl]-3-nitropyridine-2,6-diamine | MS: Calcd.: 382; Found: [M + H]+ 383. | 5-cyclopropyl-1H-pyrazol-3-amine | Method 9 |

| Ex | Product | MS | SM |
|---|---|---|---|
| 32 | $N^6$-(5-Cyclopropyl-1H-pyrazol-3-yl)-$N^2$-(4-fluorobenzyl)pyridine-2,3,6-triamine | Calcd.: 338; Found: $[M + H]^+$ 339 | Example 27 |
| 33 | (2R)-2-({3-Amino-6-[(5-cyclopropyl-1H-pyrazol-3-yl)amino]pyridin-2-yl}amino)-2-(4-fluorophenyl)ethanol | Calcd.: 368; Found: $[M + H]^+$ 369 | Example 28 |
| 34 | 2-({3-Amino-6-[(5-cyclopropyl-1H-pyrazol-3-yl)amino]pyridin-2-yl}amino)-2-(4-fluorophenyl)propane-1,3-diol | Calcd.: 398; Found: $[M + H]^+$ 399 | Example 29 |
| 35 | $N^6$-(5-Cyclopropyl-1H-pyrazol-3-yl)-$N^2$-[(1R)-1-(4-fluorophenyl)ethyl]pyridine-2,3,6-triamine | Calcd.: 352; Found: $[M + H]^+$ 353 | Example 30 |

Example 36

(S)-3-Chloro-$N^2$-(5-cyclopropyl-1H-pyrazol-3-yl)-$N^6$-(1-(4-fluorophenyl)ethyl)-5-nitropyridin-2,6-diamine A mixture of (S)-5,6-chloro-N-(1-(4-fluorophenyl)ethyl)-3-nitropyridin-2-amine (Method 13; 0.61 g, 79% pure, 1.46 mmol), 5-cyclopropyl-1H-pyrazol-3-amine (0.27 g, 2.19 mmol), and DIEA (0.38 ml, 2.19 mmol) in n-BuOH (5 ml) was heated in a sealed tube at 100° C. for 48 hours. The solvent was removed under reduced pressure and the residue was purified by column chromatography (hexane:EtOAc=2:1) to give the title compound as a yellow solid (0.57 g, 94%). NMR (400 MHz) 12.34 (s, 1H), 9.34 (s, 1H), 8.93 (d, J=7.6 Hz, 1H), 8.26 (s, 1H), 7.32 (m, 2H), 7.12 (m, 2H), 6.01 (s, 1H), 5.29 (m, 1H), 1.91 (m, 1H), 1.56 (d, J=7.2 Hz, 3H), 0.96 (m, 2H), 0.65 (m, 2H). MS: Calcd.: 416. Found: $[M+H]^+$ 417.

Examples 37-40

Following a similar procedure to Example 36, the following compounds were synthesized from a chloronitropyridine by reacting it with an amine.

Example 41

(S)-5-Chloro-$N^6$-(5-cyclopropyl-1H-pyrazol-3-yl)-$N^2$-(1-(4-fluorophenyl)ethyl)pyridine-2,3,6-triamine To a suspension of (S)-3-chloro-$N^2$-(5-cyclopropyl-1H-pyrazol-3-yl)-$N^6$-(1-(4-fluorophenyl)ethyl)-5-nitropyridin-2,6-diamine (Example 36; 0.57 g, 1.37 mmol) and zinc dust (0.447 g, 6.84 mmol) in MeOH:THF (1:1, 24 ml) was slowly added saturated ammonium chloride solution (3.5 ml). The reaction mixture was stirred at 25° C. for 2 hours, followed by addition of saturated ammonium acetate solution (5 ml). The resulting mixture was stirred for another 30 minutes. Zn dust was removed by filtration and washed with EtOAc (20 ml). The organic layer was separated, washed with brine (10 ml), dried over $Na_2SO_4$ and the solvent removed to give the title compound. MS: Calcd.: 386. Found: $[M+H]^+$ 387.

Examples 42-45

Following a similar procedure to Example 41, the following compounds were synthesized from a nitropyridine by reacting it with zinc dust.

| Ex | Product | NMR/MS | Amine | SM |
|---|---|---|---|---|
| 37 | (2R)-2-({5-Chloro-6-[(5-cyclopropyl-1H-pyrazol-3-yl)amino]-3-nitropyridin-2-yl}amino)-2-(4-fluorophenyl)ethanol | (400 MHz) 12.28 (s, 1H), 9.33 (d, J = 7.6 Hz, 1H), 9.28 (s, 1H), 8.27 (s, 1H), 7.30 (m, 2H), 7.13 (m, 1H), 5.94 (s, 1H), 5.22 (br s, 2H), 3.84-3.73 (m, 2H), 1.90 (m, 1H), 0.97 (m, 2H), 0.68 (m, 2H). MS: Calcd.: 432; Found: $[M + H]^+$ 433 | 5-cyclopropyl-1H-pyrazol-3-amine | Method 14 |
| 38 | (2R)-2-({5-Chloro-6-[(5-methyl-1H-pyrazol-3-yl)amino]-3-nitropyridin-2-yl}amino)-2-(4-fluorophenyl)ethanol | (400 MHz) 12.23 (s, 1H), 9.35 (d, J = 7.2 Hz, 1H), 9.30 (s, 1H), 8.27 (s, 1H), 7.32 (m 2H), 7.14 (m, 2H), 5.86 (s, 1H), 5.23 (t, J = 4.8 Hz, 1H), 5.18 (m, 1H), 3.81 (m, 1H), 3.74 (m, 1H), 2.23 (s, 3H). MS: Calcd.: 406; Found: $[M + H]^+$ 407 | 5-methyl-1H-pyrazol-3-amine | Method 14 |
| 39 | (2R)-2-({6-[(5-tert-Butyl-1H-pyrazol-3-yl)amino]-5-chloro-3-nitropyridin-2-yl}amino)-2-(4-fluorophenyl)ethanol | (400 MHz) 12.36 (s, 1H), 9.30 (s, 1H), 9.29 (d, J = 7.6 Hz, 1H), 8.27 (s, 1H), 7.26 (m 2H), 7.08 (m, 2H), 6.18 (s, 1H), 5.29 (m, 1H), 5.21 (t, J = 4.8 Hz, 1H), 3.81 (m, 2H), 1.28 (s, 9H). MS: Calcd.: 448; Found: $[M + H]^+$ 449 | 5-tert-butyl-1H-pyrazol-3-amine | Method 14 |
| 40 | 3-Chloro-$N^2$-(5-cyclopropyl-1H-pyrazol-3-yl)-$N^6$-(4-fluorobenzyl)-5-nitropyridine-2,6-diamine | (400 MHz) 12.33 (s, 1H), 9.32 (br s, 1H), 8.26 (s, 1H), 8.20 (br s, 1H), 7.53 (m, 2H), 7.11 (m, 1H), 5.96 (s, 1H), 4.69 (d, J = 6.0 Hz, 2H), 1.79 (m, 1H), 0.87 (m, 2H), 0.47 (m, 2H). sMS: Calcd.: 402; Found: $[M + H]^+$ 403 | (4-fluorophenyl)methanamine | Method 15 |

| Ex | Product | NMR/MS | SM |
|---|---|---|---|
| 42 | (2R)-2-({3-Amino-5-chloro-6-[(5-cyclopropyl-1H-pyrazol-3-yl)amino]pyridin-2-yl}amino)-2-(4-fluorophenyl)ethanol | MS: Calcd.: 402; Found: [M + H]$^+$ 403 | Example 37 |
| 43 | (2R)-2-({3-Amino-5-chloro-6-[(5-methyl-1H-pyrazol-3-yl)amino]pyridin-2-yl}amino)-2-(4-fluorophenyl)ethanol | MS: Calcd.: 376; Found: [M + H]$^+$ 377 | Example 38 |
| 44 | (2R)-2-({3-Amino-6-[(5-tert-butyl-1H-pyrazol-3-yl)amino]-5-chloropyridin-2-yl}amino)-2-(4-fluorophenyl)ethanol | MS: Calcd.: 418; Found: [M + H]$^+$ 419 | Example 39 |
| 45 | 5-Chloro-N$^6$-(5-cyclopropyl-1H-pyrazol-3-yl)-N$^2$-(4-fluorobenzyl)pyridine-2,3,6-triamine | MS: Calcd.: 372; Found: [M + H]$^+$ 373 | Example 40 |

Example 46

(S)-6-(5-Cyclopropyl-1H-pyrazol-3-ylamino)-5-fluoro-2-(1-(4-fluorophenyl)ethylamino) nicotinic acid (S)-6-(5-Cyclopropyl-1H-pyrazol-3-ylamino)-5-fluoro-2-(1-(4-fluorophenyl)ethylamino)nicotinamide (Example 2; 1.0 g, 2.5 mmol) was dissolved in a 10% aqueous EtOH solution (10 ml) at 25° C., followed by addition of solid KOH (2.8 g, 50.0 mmol). The reaction solution was heated to 95° C. for 4 days, cooled to 25° C., and extracted with DCM (2×50 ml). The aqueous layer was then acidified to pH 3. The resulting solid (0.55 g), was collected by filtration and dried under vacuum to give the title compound. MS: Calcd.: 399. Found: [M+H]$^+$ 400.

Example 47

(S)—N$^2$-(5-Cyclopropyl-1H-pyrazol-3-yl)-N$^6$-(1-(4-fluorophenyl)ethyl)-3-nitropyridine-2,6-diamine A mixture of 6-chloro-N-(5-cyclopropyl-1H-pyrazol-3-yl)-3-nitropyridin-2-amine (Method 16; 0.30 g, 1.07 mmol), (S)-1-(4-fluoro-phenyl)-ethylamine (0.23 g, 1.61 mmol), and DIEA (0.23 ml, 1.34 mmol) in n-BuOH (5 ml) was heated in a sealed tube at 165° C. for 18 hrs. The solvent was removed under reduced pressure and the residue was purified by column chromatography (hexane-EtOAc=1:1) to give the title compound as a yellow solid (0.41 g, 99%). $^1$H NMR (400 MHz) δ 12.22 (s, 1H), 10.98 (s, 1H), 8.70 (d, J=7.2 Hz, 1H), 8.10 (d, J=9.2 Hz, 1H), 7.39 (m, 2H), 7.18 (m, 2H), 6.22 (d, J=9.2 Hz, 1H), 6.17 (s, 1H), 5.27 (m, 1H), 1.89 (m, 1H), 1.52 (d, J=6.4 Hz, 3H), 0.95 (m, 2H), 0.64 (m 2H). MS: Calcd.: 382. Found: [M+H]$^+$ 383.

Examples 48-50

Following a similar procedure to Example 47, the following compounds were synthesized from 6-chloro-N-(5-cyclopropyl-1H-pyrazol-3-yl)-3-nitropyridin-2-amine (Method 16) and the appropriate amine.

| Ex. | Product | NMR/MS | Amine |
|---|---|---|---|
| 48 | N$^6$-(4-Fluorobenzyl)-N$^2$-(5-cyclopropyl-1H-pyrazol-3-yl)-3-nitropyridine-2,6-diamine | (400 MHz) 12.24 (s, 1H), 10.98 (s, 1H), 8.29 (br s, 1H), 8.11 (d, J = 9.2 Hz, 1H), 7.36 (m, 2H), 7.18 (m, 2H), 6.20 (d, J = 9.6 Hz, 1H), 6.19 (s, 1H), 4.66 (d, J = 5.2 Hz, 2H), 1.79 (m, 1H), 0.86 (m, 2H), 0.45 (m, 2H). MS: Calcd.: 368; Found: [M + H]$^+$ 369 | (4-fluorobenzyl)amine |
| 49 | (R)-2-[6-(5-Cyclopropyl-1H-pyrazol-3-ylamino)-5-nitropyridin-2-ylamino]-2-(4-fluorophenyl)ethanol | (400 MHz) 12.21 (s, 1H), 10.97 (s, 1H), 8.74 (d, J = 7.6 Hz, 1H), 8.09 (d, J = 9.6 Hz, 1H), 7.38 (m, 2H), 7.18 (m, 2H), 6.31 (d, J = 9.2 Hz, 1H), 6.20 (s, 1H), 5.21 (d, J = 5.6 Hz, 1H), 5.09 (t, J = 5.2 Hz, 1H), 3.64-3.75 (m, 2H), 1.91 (m, 1H), 0.98 (m, 2H), 0.66 (m, 2H). MS: Calcd.: 398; Found: [M + H]$^+$ 399. | (R)-2-amino-2-(4-fluorophenyl)ethanol |
| 50 | 2-[6-(5-Cyclopropyl-1H-pyrazol-3-ylamino)-5-nitropyridin-2-ylamino]-2-(4-fluorophenyl)propane-1,3-diol | (400 MHz) 12.02 (s, 1H), 10.95 (s, 1H), 8.07 (d, J = 9.2 Hz, 1H), 7.93 (s, 1H), 7.35 (m, 2H), 7.14 (m, 2H), 6.48 (d, J = 9.2 Hz, 1H), 5.04 (s, 1H), 4.81 (s, 2H), 4.04 (m, 2H), 3.90 (m, 2H), 1.68 (m, 1H), 0.90 (m, 2H), 0.51 (m, 2H). MS: Calcd.: 428; Found: [M + H]$^+$ 429. | 2-amino-2-(4-fluorophenyl)propane-1,3-diol |

Example 51

(S)-3-Chloro-N$^6$-(5-cyclopropyl-1H-pyrazol-3-yl)-N$^2$-[1-(4-fluorophenyl)ethyl]-5-nitropyridin-2,6-diamine A mixture of 5,6-chloro-N-(5-cyclopropyl-1H-pyrazol-3-yl)-3-nitropyridine-2-amine (Method 17; 0.26 g, 0.83 mmol), (S)-1-(4-fluoro-phenyl)ethylamine (0.17 g, 1.25 mmol), and DIEA (0.22 ml, 1.25 mmol) in n-BuOH (5 ml) was heated in a sealed tube at 165° C. for 3 hours. The solvent was removed under reduced pressure and the residue was purified by column chromatography (hexane:EtOAc=1:1) to give the title compound as a yellow solid (0.34 g, 99%). NMR (400 MHz) 12.29 (s, 1H), 10.68 (s, 1H), 8.27 (s, 1H), 8.24 (d, J=8.0 Hz, 1H), 7.39 (m, 2H), 7.16 (m, 2H), 6.11 (s, 1H), 5.42 (m, 1H), 1.89 (m, 1H), 1.60 (d, J=7.2 Hz, 3H), 0.95 (m, 2H), 0.61 (m, 2H). MS: Calcd.: 416. Found: [M+H]$^+$ 417.

Examples 52-54

Following a similar procedure to Example 51, the following compounds were synthesized from the appropriate starting material and amine.

| Ex. | Product | NMR/MS | SM | Amine 2 |
|---|---|---|---|---|
| 52 | N²-(4-Fluorobenzyl)-3-chloro-N⁶-(5-cyclopropyl-1H-pyrazol-3-yl)-5-nitropyridin-2,6-diamine | (400 MHz) 12.29 (s, 1H), 10.73 (s, 1H), 8.70 (t, J = 6.0 Hz, 1H), 8.12 (b, 1H), 7.30 (m, 2H), 7.16 (m, 2H), 6.02 (s, 1H), 4.71 (d, J = 6.0 Hz, 2H), 1.77 (m, 1H), 0.86 (m, 2H), 0.41 (m, 2H). MS: Calcd.: 402; Found: [M + H]⁺ 403. | Method 17 | (4-fluoro-phenyl)methanamine |
| 53 | (R)-2-[3-Chloro-6-(5-cyclopropyl-1H-pyrazol-3-ylamino)-5-nitropyridin-2-ylamino]-2-(4-fluorophenyl)ethanol | (400 MHz) 12.27 (s, 1H), 10.70 (s, 1H), 8.29 (d, J = 1.6 Hz, 1H), 8.03 (d, J = 7.6 Hz, 1H), 7.39 (m, 2H), 7.14 (m, 2H), 6.15 (s, 1H), 5.31 (m, 1H), 5.13 (t, J = 4.8 Hz, 1H), 3.32-3.86 (m, 2H), 1.92 (m, 1H), 0.98 (m, 2H), 0.68 (m, 2H). MS: Calcd.: 432; Found: [M + H]⁺ 433. | Method 18 | 5-cyclopropyl-1H-pyrazol-3-amine |
| 54 | (2R)-2-({3-Chloro-6-[(5-methyl-1H-pyrazol-3-yl)amino]-5-nitropyridin-2-yl}amino)-2-(4-fluorophenyl)ethanol | (400 MHz) 12.23 (s, 1H), 10.69 (s, 1H), 8.30 (s, 1H), 8.00 (d, J = 7.6 Hz, 1H), 7.41 (m 2H), 7.17 (m, 2H), 6.12-5.26 (m, 1H), 5.13 (t, J = 5.2 Hz, 1H), 3.73-3.86 (m, 2H), 2.25 (s, 3H). MS: Calcd.: 406; Found: [M + H]⁺ 407 | Method 18 | 5-methyl-1H-pyrazol-3-amine |

Example 55

(S)—N²-(5-Cyclopropyl-1H-pyrazol-3-yl)-N⁶-[1-(4-fluorophenyl)ethyl]pyridine-2,3,6-triamine To a suspension of (S)—N²-(5-cyclopropyl-1H-pyrazol-3-yl)-N⁶-[1-(4-fluorophenyl)ethyl]-3-nitropyridine-2,6-diamine (Example 47; 0.26 g, 0.68 mmol) and zinc dust (0.223 g, 3.41 mmol) in MeOH:THF (1:1, 12 ml) was slowly added saturated ammonium chloride solution (1.5 ml). The reaction mixture was stirred at 25° C. for 1 hour, to which was then added saturated ammonium acetate solution (5 ml). The resulting mixture was stirred for another 30 minutes. Zn dust was removed by filtration and washed with EtOAc (20 ml). The organic layer was separated, washed with brine (10 ml), dried over Na₂SO₄, and concentrated to give the title compound.

Examples 56-62

Following a similar procedure to Example 55, the following compounds were synthesized from a suitable nitro-pyridine.

| Ex. | Compound | NMR/MS | SM |
|---|---|---|---|
| 56 | N²-(5-Cyclopropyl-1H-pyrazol-3-yl)-N⁶-(4-fluorobenzyl)pyridine-2,3,6-triamine | MS: Calcd.: 338; Found: [M + H]⁺ 339 | Example 48 |
| 57 | (2R)-2-({5-Amino-6-[(5-cyclopropyl-1H-pyrazol-3-yl)amino]pyridin-2-yl}amino)-2-(4-fluorophenyl)ethanol | MS: Calcd.: 368; Found: [M + H]⁺ 369 | Example 49 |
| 58 | 2-({5-Amino-6-[(5-cyclopropyl-1H-pyrazol-3-yl)amino]pyridin-2-yl}amino)-2-(4-fluorophenyl)propane-1,3-diol | MS: Calcd.: 398; Found: [M + H]⁺ 399 | Example 50 |
| 59 | 5-Chloro-N²-(5-cyclopropyl-1H-pyrazol-3-yl)-N⁶-[(1S)-1-(4-fluorophenyl)ethyl]pyridine-2,3,6-triamine | MS: Calcd.: 386; Found: [M + H]⁺ 387 | Example 51 |
| 60 | 5-Chloro-N²-(5-cyclopropyl-1H-pyrazol-3-yl)-N⁶-(4-fluorobenzyl)pyridine-2,3,6-triamine | MS: Calcd.: 372; Found: [M + H]⁺ 373 | Example 52 |
| 61 | (2R)-2-({5-Amino-3-chloro-6-[(5-cyclopropyl-1H-pyrazol-3-yl)amino]pyridin-2-yl}amino)-2-(4-fluorophenyl)ethanol | MS: Calcd.: 402; Found: [M + H]⁺ 403 | Example 53 |
| 62 | (2R)-2-({5-Amino-3-chloro-6-[(5-methyl-1H-pyrazol-3-yl)amino]pyridin-2-yl}amino)-2-(4-fluorophenyl)ethanol | MS: Calcd.: 376; Found: [M + H]⁺ 377 | Example 54 |

Example 63

N-(5-Cyclopropyl-1H-pyrazol-3-yl)-N'-(4-fluorobenzyl)pyridine-2,6-diamine

To a flask was added Pd(OAc)₂ (22.4 mg, 0.1 mmol), (biphenyl-2-ylmethylene)bis(dimethylphosphine) (60 mg, 0.2 mmol) and sodium tert-butoxide (240 mg, 2.5 mmol). The flask was sealed and refilled with N₂. To the mixture was added a solution of 6-bromo-N-(4-fluorobenzyl)pyridin-2-amine (Method 19; 281 mg, 1.0 mmol) and 5-cyclopropyl-1H-pyrazol-3-amine (123 mg, 1.0 mmol) in toluene (5 ml). The reaction mixture was heated at 110° C. overnight. The solvent was removed and EtOAc was added and the mixture was washed with brine and was concentrated. Semi-prep HPLC (Gilson) purification gave the title compound (6.4 mg, 2%). ¹H NMR (CDCl₃) δ 0.65 (m, 2H), 0.95 (m, 2H), 1.80 (m, 1H), 4.43 (m, 2H), 4.91 (br s, 1H), 5.60 (br s, 1H), 5.80 (m, 1H), 6.18 (m, 1H), 6.73 (m, 1H), 7.00 (m, 2H), 7.25 (m, 3H).

Example 64

(S)-5-Chloro-6-(5-cyclopropyl-1H-pyrazol-3-ylamino)-2-(1-(5-fluoropyridin-2-yl)ethylamino)nicotinonitrile A solution of 2,5-dichloro-6-(5-cyclopropyl-1H-pyrazol-3-ylamino)nicotinonitrile (Method 43, 0.60 g, 2.04 mmol), DIEA (0.34 g, 2.65 mmol), and (S)-1-(5-fluoropyridin-2-yl)ethanamine (Method 33; 0.90 g, 6.12 mmol) in n-BuOH was heated to 120° C. for 9 hours. The reaction was then cooled to room temperature, diluted with water (20 ml), and extracted with DCM (2×50 ml). The combined organic fractions were dried over $Na_2SO_4$, filtered, and then concentrated. The resulting oil was purified by column chromatography (DCM-MeOH=100:1) to give the title compound (0.42 g, 52%). $^1$H NMR (400 MHz, $CD_3OD$) δ 8.42 (d, J=2.7 Hz, 1H), 7.61 (s, 1H), 7.51-7.49 (m, 1H), 7.38-7.32 (m, 1H), 6.06 (br s, 1H), 5.28-5.22 (m, 1H), 1.94-1.88 (m, 1H), 1.58 (d, J=6.9 Hz, 3H), 1.01 (br s, 2H), 0.76-0.75 (m, 2H). MS: Calcd.: 397. Found: [M+H]$^+$ 398.

Example 65

(S)—$N^2$-(5-Cyclopropyl-1H-pyrazol-3-yl)-3-fluoro-$N^6$-(1-(4-fluorophenyl)ethyl)-5-nitropyridine-2,6-diamine To a solution of (S)-5,6-difluoro-N-(1-(4-fluorophenyl)ethyl)-3-nitropyridin-2-amine (Method 23, 0.60 g, 2.0 mmol) in THF (10 ml) at room temperature was added 5-cyclopropyl-1H-pyrazol-3-amine (0.50 g, 4.0 mmol), and DIEA (0.26 g, 2.0 mmol). The reaction was then heated to 55° C. for 24 hours, cooled to room temperature, and quenched with water. The reaction was then extracted with DCM (2×75 ml), and the combined organic fractions were dried over $Na_2SO_4$, filtered, and then concentrated. The resulting oil was purified by column chromatography (DCM-MeOH=100:1) to give the title compound (0.53 g, 66%). $^1$H NMR (400 MHz, $CD_3OD$) δ 8.00 (d, J=11.1 Hz, 1H), 7.38-7.35 (m, 2H), 7.07-7.02 (m, 2H), 6.17 (s, 1H), 5.41-5.39 (m, 1H), 1.93-1.87 (m, 1H), 1.61 (d, J=7.0 Hz, 3H), 1.02-1.00 (m, 2H), 0.69-0.66 (m, 2H). MS: Calcd.: 400. Found: [M+H]$^+$ 401.

Example 66

(S)-3-Fluoro-$N^6$-(1-(4-fluorophenyl)ethyl)-$N^2$-(5-isopropoxy-1H-pyrazol-3-yl)-5-nitropyridine-2,6-diamine To a solution of (S)-5,6-difluoro-N-(1-(4-fluorophenyl)ethyl)-3-nitropyridin-2-amine (Method 23; 0.60 g, 2.0 mmol) in THF (10 ml) at room temperature was added 5-isopropoxy-1H-pyrazol-3-amine (0.50 g, 3.0 mmol), and DIEA (0.29 g, 2.2 mmol). The reaction was then heated to 55° C. for 24 hours, cooled to room temperature, and quenched with water. The reaction was then extracted with DCM (2×75 ml), and the combined organic fractions were dried over $Na_2SO_4$, filtered, and then concentrated. The resulting oil was purified by column chromatography (DCM-MeOH=100:1) to give the title compound (0.34 g, 40%). $^1$H NMR (400 MHz, $CD_3OD$) δ 8.00 (d, J=10.9 Hz, 1H), 7.45-7.35 (m, 2H), 7.07-7.03 (m, 2H), 5.88-5.71 (m, 1H), 5.48-5.30 (m, 1H), 4.58-4.29 (m, 1H), 1.68-1.56 (m, 3H), 1.34-1.28 (m, 6H). MS: Calcd.: 418. Found: [M+H]$^+$ 419.

Example 67

(R)-2-(6-(5-Cyclopropyl-1H-pyrazol-3-ylamino)-5-fluoro-3-nitropyridin-2-ylamino)-2-(4-fluorophenyl)ethanol To a solution of (S)-2-(5,6-difluoro-3-nitropyridin-2-ylamino)-2-(4-fluorophenyl)ethanol (Method 25, 0.40 g, 1.3 mmol) in THF (10 ml) at room temperature was added 5-cyclopropyl-1H-pyrazol-3-amine (0.31 g, 2.6 mmol), and DIEA (0.18 g, 1.4 mmol). The reaction was then heated to 55° C. for 12 hours, cooled to room temperature, and quenched with water. The reaction was then extracted with DCM (2×75 ml), and the combined organic fractions were dried over $Na_2SO_4$, filtered, and then concentrated. The resulting oil was purified by column chromatography (DCM-MeOH=100:1) to give the title compound (0.45 g, 85%). $^1$H NMR (400 MHz, $CDCl_3$) δ 10.84 (s, 1H), 8.02 (d, J=10.7 Hz, 1H), 7.35-7.31 (m, 2H), 7.10-7.06 (m, 2H), 6.21-6.19 (m, 1H), 5.80 (br s, 1H), 4.07 (dd, J=11.3, 3.9 Hz, 1H), 3.99 (dd, J=11.3, 6.4 Hz, 1H), 1.88-1.86 (m, 1H), 1.62 (br s, 1H), 0.98-0.95 (m, 2H), 0.70-0.68 (m, 2H). MS: Calcd.: 416. Found: [M+H]$^+$ 417.

Example 68

(R)-2-(5-Fluoro-6-(5-methyl-1H-pyrazol-3-ylamino)-3-nitropyridin-2-ylamino)-2-(4-fluorophenyl)ethanol To a solution of (S)-2-(5,6-difluoro-3-nitropyridin-2-ylamino)-2-(4-fluorophenyl)ethanol (Method 25; 0.60 g, 1.9 mmol) in THF (10 ml) at room temperature was added 5-methyl-1H-pyrazol-3-amine (0.37 g, 3.8 mmol), and DIEA (0.27 g, 2.1 mmol). The reaction was heated to 55° C. for 12 hours, cooled to room temperature, and quenched with water. The reaction was then extracted with DCM (2×75 ml), and the combined organic fractions were dried over $Na_2SO_4$, filtered, and then concentrated. The resulting oil was purified by column chromatography (DCM-MeOH=100:1) to give the title compound (0.51 g, 68%). $^1$H NMR (400 MHz, $CDCl_3$) δ 10.85 (br s, 1H), 8.02 (d, J=10.5 Hz, 1H), 7.34-7.31 (m, 2H), 7.10-7.06 (m, 2H), 6.26-6.25 (m, 1H), 5.86 (br s, 1H), 5.30-5.27 (m, 1H), 4.07 (dd, J=11.3 and 3.9 Hz, 1H), 3.97 (dd, J=11.1, 6.2 Hz, 1H), 2.27 (s, 3H), 1.61 (br s, 1H). MS: Calcd.: 390. Found: [M+H]$^+$ 391.

Example 69

(S)-3-Chloro-$N^2$-(1-(4-fluorophenol)ethyl)-$N^6$-(5-isopropoxy-1H-pyrazol-3-yl)-5-nitropyridine-2,6-diamine A mixture of 5,6-dichloro-N-(5-isopropoxy-1H-pyrazol-3-yl)-3-nitropyridin-2-amine (Method 26, 0.25 g, 0.75 mmol), (S)-1-(4-fluoro-phenyl)-ethylamine (0.13 g, 0.90 mmol) and DIEA (0.16 ml, 0.94 mmol) in n-BuOH (3 ml) was heated in a sealed tube at 145° C. for 4 hours. The solvent was removed under reduced pressure and the residue was purified by column chromatography (hexane-EtOAc=1:1) to give the title compound as a yellow solid (0.32 g, 98%). $^1$H NMR (400 MHz) δ 12.16 & 11.72 (s, 1H), 10.64 & 10.58 (s, 1H), 8.30 (m, 2H), 7.37 & 7.31 (m, 2H), 7.16 & 7.08 (m, 2H), 5.81 & 5.71 (s, 1H), 5.48 & 5.33 (m, 1H), 4.60 & 4.21 (m, 1H), 1.61 & 1.57 (d, J=6.8 Hz, 3H), 1.25 (m, 6H). MS: Calcd.: 434. Found: [M+H]$^+$ 435.

Example 70

(S)-3-Chloro-N⁶-(1-(4-fluorophenyl)ethyl)-N²-(5-isopropoxy-1H-pyrazol-3-yl)-5-nitropyridine-2,6-diamine A mixture of 3,6-dichloro-N-(5-isopropoxy-1H-pyrazol-3-yl)-5-nitropyridin-2-amine (Method 27, 0.25 g, 0.75 mmol), (s)-1-(4-fluoro-phenyl)-ethylamine (0.13 g, 0.90 mmol) and DIEA (0.16 ml, 0.94 mmol) in n-BuOH (3 ml) was heated in a sealed tube at 145° C. for 2 hours. The solvent was removed under reduced pressure and the residue was purified by column chromatography (hexane-EtOAc=1:1) to give the title compound as a yellow solid (0.32 g, 98%). $^1$H NMR (400 MHz) δ 12.22 & 11.40 (s, 1H), 9.74 & 9.37 (s, 1H), 8.93 (d, J=7.6 Hz, 1H), 8.33 & 8.27 (s, 1H), 7.34 & 7.27 (m, 2H), 7.12 & 7.05 (m, 2H), 5.75 & 5.62 (s, 1H), 5.35 & 5.25 (m, 1H), 4.66 & 4.03 (m, 1H), 1.55 (d, J=6.4 Hz, 3H), 1.29 (d, J=6.0 Hz, 6H). MS: Calcd.: 434. Found: [M+H]⁺ 435.

Example 71

(S)—N⁶-(1-(4-Fluorophenyl)ethyl)-N²-(5-isopropoxy-1H-pyrazol-3-yl)-3-nitropyridine-2,6-diamine A mixture of 6-chloro-N-(5-isopropoxy-1H-pyrazol-3-yl)-3-nitropyridin-2-amine (Method 28, 0.33 g, 1.1 mmol), (s)-1-(4-fluoro-phenyl)-ethylamine (0.16 g, 1.2 mmol) and DIEA (0.21 ml, 1.2 mmol) in n-BuOH (3 ml) was heated in a sealed tube at 165° C. for 4 hours. The solvent was removed under reduced pressure and the residue was purified by column chromatography (hexane-EtOAc=1:1) to give the title compound as a yellow solid (0.43 g, 97%). $^1$H NMR (400 MHz) δ 12.09, 12.05 & 11.64 (s, 1H), 10.94, 10.87 & 10.72 (s, 1H), 8.98, 8.76 & 8.70 (d, J=7.6 Hz, 1H), 8.16 & 8.11 (d, J=9.6 Hz, 1H), 7.40-7.33 (m, 2H), 7.22-7.10 (m, 2H), 6.25 & 6.04 (d, J=9.6 Hz, 1H), 6.23 & 5.86 (d, J=13.6 Hz, 1H), 5.31, 5.21 & 4.89 (m, 1H), 4.71, 4.59 & 4.27 (m, 1H), 1.52 (m, 3H), 1.26 (m, 6H). MS: Calcd.: 400. Found: [M+H]⁺ 401.

Example 72

(S)—N-((6-(5-Cyclopropyl-1H-pyrazol-3-ylamino)-5-fluoro-2-(1-(4-fluorophenyl)ethylamino) pyridin-3-yl)methyl)-2-morpholinoacetamide A solution of (S)-3-(aminomethyl)-N⁶-(5-cyclopropyl-1H-pyrazol-3-yl)-5-fluoro-N²-(1-(4-fluorophenyl)ethyl)pyridine-2,6-diamine (Example 3, 0.16 g, 0.42 mmol), 2-morpholinoacetic acid (0.06 g, 0.42 mmol), HBTU (0.16 g, 0.42 mmol) and DIEA (0.16 g, 1.2 mmol) in DCM (3 ml) was stirred at room temperature for 1 hour. The reaction was then quenched with a saturated aqueous solution of NaHCO₃, and extracted with DCM (2×50 ml). The combined organic fractions were dried over Na₂SO₄, filtered, and then concentrated. The resulting oil was purified by column chromatography (DCM-MeOH=100:1) to give the title compound (0.02 g, 10%). $^1$H NMR (400 MHz, CD₃OD) δ 7.35 (br s, 2H), 7.17 (br s, 1H), 7.01-6.97 (m, 2H), 6.06 (br s, 1H), 5.16-4.99 (m, 1H), 4.30 (br s, 2H), 3.68 (br s, 4H), 3.06 (br s, 2H), 2.48 (br s, 4H), 1.87-1.82 (m, 1H), 1.51 (d, J=6.4 Hz, 3H), 0.91 (br s, 2H), 0.64 (br s, 2H). MS: Calcd.: 511. Found: [M+H]⁺ 512.

Example 73

(S)-6-(5-Cyclopropyl-1H-pyrazol-3-ylamino)-5-fluoro-2-(1-(4-fluorophenyl)ethylamino) nicotinaldehyde (S)-6-(5-Cyclopropyl-1H-pyrazol-3-ylamino)-5-fluoro-2-(1-(4-fluorophenyl) ethylamino)nicotinonitrile (Example 1, 0.4 g, 1.1 mmol) was dissolved in the mixture pyridine-acetic acid-water (1:1:1, 18 ml total volume) at room temperature, to which was added Raney nickel (0.09 g, 1.1 mmol). The reaction was purged with nitrogen, evacuated, and then placed under hydrogen filled balloon for 18 hours. The reaction mixture was flushed with nitrogen, and filtered to remove the catalyst, which was washed with MeOH (30 ml). The filtrate was then extracted with DCM (5×50 ml), washed with aq. NaHCO₃, and purified by reverse phase column chromatography (5-30% ACN) to give the title compound (0.18 g, 45%). $^1$H NMR (400 MHz, CD₃OD) δ 9.40 (s, 1H), 7.45 (d, J=10.4 Hz, 1H), 7.34-7.31 (m, 2H), 7.05-7.01 (m, 2H), 6.11 (s, 1H), 5.26 (s, 1H), 1.92-1.86 (m, 1H), 1.55 (d, J=7.0 Hz, 3H), 1.00-0.98 (m, 2H), 0.71-0.64 (m, 2H). MS: Calcd.: 383. Found: [M+H]⁺ 384.

Example 74

(S)-(6-(5-Cyclopropyl-1H-pyrazol-3-ylamino)-5-fluoro-2-(1-(4-fluorophenyl)ethylamino) pyridin-3-yl)methanol To a solution of (S)-6-(5-cyclopropyl-1H-pyrazol-3-ylamino)-5-fluoro-2-(1-(4-fluorophenyl)ethylamino)nicotinaldehyde (Example 73; 0.10 g, 0.26 mmol) in MeOH (5 ml) at 0° C. was added NaBH₄ (0.012 g, 0.33 mmol). The reaction was stirred for 10 minutes, and then quenched with water and extracted with DCM (2×20 ml). The combined organic fractions were dried over Na₂SO₄, filtered, and then concentrated. The resulting oil was purified by column chromatography (DCM-MeOH=100:1) to give the title compound (0.088 g, 88%). $^1$H NMR (400 MHz, CD₃OD) δ 7.42-7.39 (m, 2H), 7.16-7.01 (m, 1H), 7.01 (br s, 2H), 6.06-5.41 (m, 1H), 5.19-5.02 (m, 1H), 4.52 (br s, 2H), 1.88-1.81 (m, 1H), 1.53 (d, J=6.6 Hz, 3H), 0.97-0.91 (m, 2H), 0.65 (br s, 2H). MS: Calcd.: 385. Found: [M+H]⁺ 386.

Example 75

(S)—N²-(5-Cyclopropyl-1H-pyrazol-3-yl)-3-fluoro-N⁶-(1-(4-fluorophenyl)ethyl)-5-(morpholinomethyl) pyridine-2,6-diamine To a solution of (S)-6-(5-cyclopropyl-1H-pyrazol-3-ylamino)-5-fluoro-2-(1-(4-fluorophenyl)ethylamino)nicotinaldehyde (Example 73, 0.12 g, 0.31 mmol) in DCE (5 ml) was added morpholine (0.1 g, 1.14 mmol) and NaBH(OAc)₃ (0.30 g, 1.5 mmol). The reaction was then stirred for 2 days, quenched with aq. Na₂CO₃ (10 ml), and extracted with DCM (2×20 ml). The combined organic fractions were dried over Na₂SO₄, filtered, and then concentrated. The resulting oil was purified by reverse-phase column chromatography (5-35% ACN) to give the title compound (0.09 g, 67%). $^1$H NMR (400 MHz, CD₃OD) δ 7.41 (br s, 2H), 7.06-7.02 (m, 3H), 6.13 & 5.44 (s, 1H), 5.12 & 4.97 (s, 1H), 3.63 (br s, 4H), 3.42 (br s, 2H), 2.41 (br s, 4H), 1.87-1.82 (m, 1H), 1.54 (d, J=6.5 Hz, 3H), 0.96-0.90 (m, 2H), 0.65-0.64 (m, 2H). MS: Calcd.: 454. Found: [M+H]⁺ 455.

Example 76

(R)-2-(4-Fluorophenyl)-2-(6-(5-methyl-1H-pyrazol-3-ylamino)-3-nitropyridin-2-ylamino)ethanol A mixture of (R)-2-(6-chloro-3-nitropyridin-2-ylamino)-2-(4-fluorophenyl)ethanol (Method 29, 0.36 g, 1.2 mmol), 5-methyl-1H-pyrazol-3-amine (0.14 g, 1.4 mmol), and DIEA (0.25 ml, 1.4 mmol) in n-BuOH (5 ml) was heated in a sealed tube at 90° C. for 6 days. The solvent was removed under reduced pressure and the residue was purified by column chromatography (EtOAc) to give the title compound as a yellow solid (0.31 g, 73%). $^1$H NMR (400 MHz) δ 12.06 (s, 1H), 10.40 (br, 1H), 9.58 (br, 1H), 8.11 (d, J=9.2 Hz, 1H), 7.40 (m, 2H), 7.16 (m, 2H), 6.20 (br, 1H), 6.02 (s, 1H), 5.29 (br, 1H), 5.24 (t, J=4.4 Hz, 1H), 3.85 (m, 1H), 3.74 (m, 1H), 2.20 (s, 3H). MS: Calcd.: 372. Found: [M+H]$^+$ 373.

Example 77

(S)—N$^2$-(1-(4-Fluorophenyl)ethyl)-N$^6$-(5-isopropoxy-1H-pyrazol-3-yl)-3-nitropyridine-2,6-diamine A mixture of (S)-6-chloro-N-(1-(4-fluorophenyl)ethyl)-3-nitropyridin-2-amine (Method 30, 1.08 g, 3.7 mmol), 5-isopropoxy-1H-pyrazol-3-amine (0.57 g, 4.0 mmol), and DIEA (0.80 ml, 4.6 mmol) in n-BuOH (10 ml) was heated in a sealed tube at 115° C. for 72 hours. The solvent was removed under reduced pressure and the residue was purified by chromatography (hexane-EtOAc=3:1) to give the title compound as a yellow solid (0.32 g, 22%). MS: Calcd.: 400. Found: [M+H]$^+$ 401.

Example 78

(R)-2-(4-Fluorophenyl)-2-(6-(5-isopropoxy-1H-pyrazol-3-ylamino)-5-nitropyridin-2-ylamino)ethanol A mixture of 6-chloro-N-(5-isopropoxy-1H-pyrazol-3-yl)-3-nitropyridin-2-amine (Method 28; 0.25 g, 0.84 mmol), (R)-2-amino-2-(4-fluorophenyl)ethanol (0.15 g, 0.97 mmol) and DIEA (0.16 ml, 0.92 mmol) in n-BuOH (3 ml) was heated in a sealed tube at 165° C. for 4 hours. The solvent was removed under reduced pressure and the residue was purified by column chromatography (hexane-EtOAc=1:2) to give the title compound as a yellow solid (0.30 g, 87%). $^1$H NMR (400 MHz) δ 12.12, 12.10 & 11.61 (s, 1H), 10.94, 10.89 & 10.74 (s, 1H), 9.05, 8.82 & 8.73 (d, J=7.2 Hz, 1H), 8.13 & 8.11 (d, J=9.2 Hz, 1H), 7.45-7.32 (m, 2H), 7.20-7.10 (m, 2H), 6.32 & 6.07 (d, J=9.2 Hz, 1H), 5.90, 5.83 & 5.79 (s, 1H), 5.23, 5.12 & 4.78 (m, 2H), 4.71, 4.64 & 4.37 (m, 1H), 3.69 (m, 2H), 1.34 & 1.29 (d, J=6.0 Hz, 6H). MS: Calcd.: 416. Found: [M+H]$^+$ 417.

Example 79

(S)—N-((6-(5-Cyclopropyl-1H-pyrazol-3-ylamino)-5-fluoro-2-(1-(4-fluorophenyl)ethylamino) pyridin-3-yl)methyl)isoxazole-5-carboxamide To a solution of (S)-3-(aminomethyl)-N$^6$-(5-cyclopropyl-1H-pyrazol-3-yl)-5-fluoro-N$^2$-(1-(4-fluorophenyl)ethyl)pyridine-2,6-diamine (Example 3, 0.08 g, 0.21 mmol) in DCM-THF mixture (1:1, 4 ml) at 0° C. was added 1.0 eq. of isoxazole-5-carboxylic acid loaded TFP resin. The resulting mixture was stirred vigorously for 1 hour at 0° C., and then filtered. The remaining resin was then washed with DCM-THF (1:1, 2×10 ml portions) for 30 min, and then filtered. The combined filtrates were concentrated, and the resulting oil was purified by column chromatography to give the title compound (3.4 mg, 4%). MS: Calcd.: 479. Found: [M+H]$^+$ 480.

Example 80-103

The following compounds were prepared by the procedure similar to that of Example 79 using (S)-3-(aminomethyl)-N$^6$-(5-cyclopropyl-1H-pyrazol-3-yl)-5-fluoro-N$^2$-(1-(4-fluorophenyl)ethyl)pyridine-2,6-diamine (Example 3) and a TFP resin loaded reagent.

| Ex. | Compound | NMR and/or LC/MS | TFP loaded resin |
| --- | --- | --- | --- |
| 80 | (S)—N-((6-(5-Cyclopropyl-1H-pyrazol-3-ylamino)-5-fluoro-2-(1-(4-fluorophenyl)ethylamino)pyridin-3-yl)methyl)benzamide | MS: Calcd.: 488; Found: [M + H]$^+$ 489. | benzoic acid |
| 81 | (S)—N-((6-(5-Cyclopropyl-1H-pyrazol-3-ylamino)-5-fluoro-2-(1-(4-fluorophenyl)ethylamino)pyridin-3-yl)methyl)nicotinamide | MS: Calcd.: 489; Found: [M + H]$^+$ 490. | pyridine-3-carboxylic acid |
| 82 | (S)—N-((6-(5-Cyclopropyl-1H-pyrazol-3-ylamino)-5-fluoro-2-(1-(4-fluorophenyl)ethylamino)pyridin-3-yl)methyl)isonicotinamide | MS: Calcd.: 489; Found: [M + H]$^+$ 490. | pyridine-4-carboxylic acid |
| 83 | (S)—N-((6-(5-Cyclopropyl-1H-pyrazol-3-ylamino)-5-fluoro-2-(1-(4-fluorophenyl)ethylamino)pyridin-3-yl)methyl)-5-methylisoxazole-4-carboxamide | MS: Calcd.: 493; Found: [M + H]$^+$ 494. | 5-methylisoxazole-4-carboxylic acid |
| 84 | (S)—N-((6-(5-Cyclopropyl-1H-pyrazol-3-ylamino)-5-fluoro-2-(1-(4-fluorophenyl)ethylamino)pyridin-3-yl)methyl)thiophene-2-carboxamide | MS: Calcd.: 494; Found: [M + H]$^+$ 495. | thiophene-2-carboxylic acid |

| Ex. | Compound | NMR and/or LC/MS | TFP loaded resin |
|---|---|---|---|
| 85 | (S)—N-((6-(5-Cyclopropyl-1H-pyrazol-3-ylamino)-5-fluoro-2-(1-(4-fluorophenyl)ethylamino)pyridin-3-yl)methyl)-2-(4-(dimethylamino)phenyl)acetamide | MS: Calcd.: 545; Found: [M + H]$^+$ 546. | 4-(dimethylamino)phenyl acetic acid |
| 86 | (S)—N-((6-(5-Cyclopropyl-1H-pyrazol-3-ylamino)-5-fluoro-2-(1-(4-fluorophenyl)ethylamino)pyridin-3-yl)methyl)-2-(N-(isopropyl)-N-methylsulfonamido)acetamide | MS: Calcd.: 561; Found: [M + H]$^+$ 562. | (isopropylmethanesulfonylamino)acetic acid |
| 87 | (S)—N-((6-(5-Cyclopropyl-1H-pyrazol-3-ylamino)-5-fluoro-2-(1-(4-fluorophenyl)ethylamino)pyridin-3-yl)methyl)-1-(methylsulfonyl)piperidine-4-carboxamide | MS: Calcd.: 573; Found: [M + H]$^+$ 574. | 1-methanesulfonyl piperidine-4-carboxylic acid |
| 88 | (S)—N-((6-(5-Cyclopropyl-1H-pyrazol-3-ylamino)-5-fluoro-2-(1-(4-fluorophenyl)ethylamino)pyridin-3-yl)methyl)-6-(dimethylamino)nicotinamide | MS: Calcd.: 532; Found: [M + H]$^+$ 533. | 6-dimethylamino nicotinic acid |
| 89 | (S)—N-((6-(5-Cyclopropyl-1H-pyrazol-3-ylamino)-5-fluoro-2-(1-(4-fluorophenyl)ethylamino)pyridin-3-yl)methyl)-6-morpholino nicotinamide | MS: Calcd.: 574; Found: [M + H]$^+$ 575. | (6-morpholin-4-yl)nicotinic acid |
| 90 | (S)—N-((6-(5-Cyclopropyl-1H-pyrazol-3-ylamino)-5-fluoro-2-(1-(4-fluorophenyl)ethylamino)pyridin-3-yl)methyl)-2-(pyridin-3-yl)acetamide | MS: Calcd.: 503; Found: [M + H]$^+$ 504. | (3-pyridyl)acetic acid |
| 91 | (S)—N-((6-(5-Cyclopropyl-1H-pyrazol-3-ylamino)-5-fluoro-2-(1-(4-fluorophenyl)ethylamino)pyridin-3-yl)methyl)tetrahydro-2H-thiopyran-4-carboxamide | MS: Calcd.: 512; Found: [M + H]$^+$ 513. | tetrahydrothiopyran-4-carboxylic acid |
| 92 | (S)—N-((6-(5-Cyclopropyl-1H-pyrazol-3-ylamino)-5-fluoro-2-(1-(4-fluorophenyl)ethylamino)pyridin-3-yl)methyl)-2-(thiophen-2-yl)acetamide | MS: Calcd.: 508; Found: [M + H]$^+$ 509. | 2-thiophene acetic acid |
| 93 | (S)—N-((6-(5-Cyclopropyl-1H-pyrazol-3-ylamino)-5-fluoro-2-(1-(4-fluorophenyl)ethylamino)pyridin-3-yl)methyl)-2-(thiophen-3-yl)acetamide | MS: Calcd.: 508; Found: [M + H]$^+$ 509. | 3-thiophene acetic acid |
| 94 | (S)—N-((6-(5-Cyclopropyl-1H-pyrazol-3-ylamino)-5-fluoro-2-(1-(4-fluorophenyl)ethylamino)pyridin-3-yl)methyl)-3-phenylpropanamide | MS: Calcd.: 516; Found: [M + H]$^+$ 517. | hydrocinnamic acid |
| 95 | (S)—N-(2-((6-(5-Cyclopropyl-1H-pyrazol-3-ylamino)-5-fluoro-2-(1-(4-fluorophenyl)ethylamino)pyridin-3-yl)methylamino)-2-oxoethyl)-N-methylbenzamide | MS: Calcd.: 559; Found: [M + H]$^+$ 560. | N-methylhippuric acid |
| 96 | (S)—N-((6-(5-Cyclopropyl-1H-pyrazol-3-ylamino)-5-fluoro-2-(1-(4-fluorophenyl)ethylamino)pyridin-3-yl)methyl)-2-(N-phenethyl-N-methylsulfonamido)acetamide | MS: Calcd.: 623; Found: [M + H]$^+$ 624. | (methanesulfonylphenethylamino)acetic acid |
| 97 | (S)—N-((6-(5-Cyclopropyl-1H-pyrazol-3-ylamino)-5-fluoro-2-(1-(4-fluorophenyl)ethylamino)pyridin-3-yl)methyl)-4-(dimethylamino)benzamide | MS: Calcd.: 531; Found: [M + H]$^+$ 532. | 4-(dimethylamino)benzoic acid |

-continued

| Ex. | Compound | NMR and/or LC/MS | TFP loaded resin |
|---|---|---|---|
| 98 | (S)—N-((6-(5-Cyclopropyl-1H-pyrazol-3-ylamino)-5-fluoro-2-(1-(4-fluorophenyl)ethylamino)pyridin-3-yl)methyl)benzenesulfonamide | $^1$H NMR (400 MHz, CD$_3$OD) δ 7.90-7.88 (m, 2H), 7.65-7.55 (m, 3H), 7.44-7.41 (m, 2H), 7.03-6.99 (m, 3H), 5.75 (br s, 1H), 5.10-5.08 (m, 1H), 3.88 (dd, J = 35.2, 14.2 Hz, 2H), 1.88-1.84 (m, 1H), 1.55 (d, J = 6.8 Hz, 3H), 0.95-0.93 (m, 2H), 0.67-0.64 (m, 2H). MS: Calcd.: 524; Found: [M + H]$^+$ 525. | benzenesulfonyl chloride |
| 99 | (S)—N-((6-(5-Cyclopropyl-1H-pyrazol-3-ylamino)-5-fluoro-2-(1-(4-fluorophenyl)ethylamino)pyridin-3-yl)methyl)cyclopropanecarboxamide | MS: Calcd.: 452; Found: [M + H]$^+$ 453. | cyclopropane carboxylic acid |
| 100 | (S)—N-((6-(5-Cyclopropyl-1H-pyrazol-3-ylamino)-5-fluoro-2-(1-(4-fluorophenyl)ethylamino)pyridin-3-yl)methyl)-1H-pyrrole-2-carboxamide | MS: Calcd.: 477; Found: [M + H]$^+$ 478. | pyrrole-2-carboxylic acid |
| 101 | N-((6-(5-Cyclopropyl-1H-pyrazol-3-ylamino)-5-fluoro-2-((S)-1-(4-fluorophenyl)ethylamino)pyridin-3-yl)methyl)tetrahydrofuran-2-carboxamide | MS: Calcd.: 482; Found: [M + H]$^+$ 483. | tetrahydrofuran-3-carboxylic acid |
| 102 | (S)—N-((6-(5-Cyclopropyl-1H-pyrazol-3-ylamino)-5-fluoro-2-(1-(4-fluorophenyl)ethylamino)pyridin-3-yl)methyl)furan-2-carboxamide | MS: Calcd.: 478; Found: [M + H]$^+$ 479. | 2-furoic acid |
| 103 | (S)—N-((6-(5-Cyclopropyl-1H-pyrazol-3-ylamino)-5-fluoro-2-(1-(4-fluorophenyl)ethylamino)pyridin-3-yl)methyl)cyclopropanesulfonamide | $^1$H NMR (400 MHz, CD$_3$OD) δ 7.41 (br s, 2H), 7.15 (br s, 1H), 7.01-6.97 (m, 2H), 6.07 & 5.42 (s, 1H), 5.17 & 5.03 (s, 1H), 4.14 (br s, 2H), 2.58 (br s, 1H), 1.88-1.84 (m, 1H), 1.52 (d, J = 6.8 Hz, 3H), 1.10-0.92 (m, 6H), 0.66 (br s, 2H). MS: Calcd.: 488; Found: [M + H]$^+$ 489. | cyclopropylsulfonyl chloride |

Example 104

(S)-2-Amino-N-((6-(5-cyclopropyl-1H-pyrazol-3-ylamino)-5-fluoro-2-((S-1-(4-fluorophenyl)ethylamino)pyridin-3-yl)methyl)-3-methylbutanamide A solution of (S)-3-(aminomethyl)-N$^6$-(5-cyclopropyl-1H-pyrazol-3-yl)-5-fluoro-N$^2$-(1-(4-fluorophenyl)ethyl)pyridine-2,6-diamine (Example 3; 0.10 g, 0.26 mmol), (S)-2-(tert-butoxycarbonylamino)-3-methylbutanoic acid (0.06 g, 0.26 mmol), and HBTU (0.10 g, 0.26 mmol) in DCM (3 ml) was stirred at room temperature for 1 hour. The reaction was then quenched with a saturated aqueous solution of NaHCO$_3$, and extracted with DCM (2×50 ml). The combined organic fractions were dried over Na$_2$SO$_4$, filtered, and then concentrated. The resulting oil was then passed through a silica plug. The resulting foam was placed in dioxane (4 ml) and 4 M HCl in dioxane (1 ml) was then added, and the reaction was stirred for 3 hours. The reaction was then concentrated to give a solid which was dissolved in a minimal amount of MeOH (0.5 ml) with stirring, followed by fast addition of ether (50 ml). The resulting solid was filtered, washed with ether, and dried to give the title compound (0.033 g, 26%). $^1$H NMR (400 MHz, CD$_3$OD) δ 7.58 (d, J=10.7 Hz, 1H), 7.49-7.46 (m, 2H), 7.07-7.02 (m, 2H), 5.80 (s, 1H), 5.09-5.04 (m, 1H), 4.58 (dd, J=15.4, 6.8 Hz, 1H), 4.26 (dd, J=15.4, 5.2 Hz, 1H), 3.71 (d, J=6.0 Hz, 1H), 2.23-2.18 (m, 1H), 2.01-1.97 (m, 1H), 1.63 (d, J=6.8 Hz, 3H), 1.19-1.13 (m, 2H), 1.05-1.03 (m, 6H), 0.85-0.81 (m, 2H). MS: Calcd.: 483. Found: [M+H]$^+$ 484.

Example 105

(S,E)-N$^2$-(5-Cyclopropyl-1H-pyrazol-3-yl)-5-((cyclopropylimino)methyl)-3-fluoro-N$^6$-(1-(4-fluorophenyl)ethylpyridine-2,6-diamine To a solution of (S)-6-(5-cyclopropyl-1H-pyrazol-3-ylamino)-5-fluoro-2-(1-(4-fluorophenyl)ethylamino)nicotinaldehyde (Example 73, 0.10 g, 0.26 mmol) in THF (5 ml) was added cyclopropanamine (0.03 g, 0.52 mmol) and NaBH (OAc)₃ (0.55 g, 0.26 mmol). The reaction was stirred for 3 hours, quenched with aqueous Na₂CO₃ (10 ml), and extracted with DCM (2×20 ml). The combined organic fractions were dried over Na₂SO₄, filtered, and then concentrated. The resulting oil was purified by reverse phase column chromatography (5-35% ACN) to give the title compound (0.068 g, 62%). $^1$H NMR (400 MHz) δ 11.92 (s, 1H), 9.62 (s, 1H), 8.93 (s, 1H), 8.35 (s, 1H), 7.39 (d, J=7.4 Hz, 1H), 7.31-7.27 (m, 2H), 7.16-7.11 (m, 2H), 6.10 (s, 1H), 5.13-5.10 (m, 1H), 2.96-2.94 (m, 1H), 1.89-1.80 (m, 1H), 1.42 (d, J=6.9 Hz, 3H), 0.98-0.88 (m, 2H), 0.76-0.63 (m, 2H). MS: Calcd.: 422. Found: [M+H]⁺ 423.

Example 106

(S)—N²-(5-Cyclopropyl-1H-pyrazol-3-YD-3-fluoro-N⁶-(1-(4-fluorophenyl)ethyl)pyridine-2,6-diamine A mixture of N-(5-cyclopropyl-1H-pyrazol-3-yl)-3,6-difluoropyridin-2-amine (Method 31, 0.10 g, 0.42 mmol) and (S)-1-(4-fluorophenyl)ethanamine (0.3 g, 2.2 mmol) were heated to 185° C. under microwave conditions (30 min×3 cycles). The resulting dark oil was purified by column chromatography (DCM-MeOH=80:1) to give the title compound (0.04 g, 26%). $^1$H NMR (400 MHz, CD₃OD) δ 7.08-6.99 (m, 3H), 6.67-6.62 (m, 2H), 6.22 (dd, J=8.9, 2.3 Hz, 1H), 5.04 (s, 1H), 4.64-4.59 (m, 1H), 1.16-1.12 (m, 4H), 0.30-0.14 (m, 3H), 0.04-0.02 (m, 1H). MS: Calcd.: 355. Found: [M+H]⁺ 356.

Example 107

(S)—N²-(5-Cyclopropyl-1H-pyrazol-3-yl)-3-fluoro-N-(1-(4-fluorophenyl)ethyl)-5-((methylamino)methyl)pyridine-2,6-diamine To a solution of (S)-6-(5-cyclopropyl-1H-pyrazol-3-ylamino)-5-fluoro-2-(1-(4-fluorophenyl)ethylamino)nicotinaldehyde (Example 73, 0.10 g, 0.26 mmol) in THF (5 ml) was added methylamine (2.0 M in THF, 0.52 mmol) and NaBH(OAc)₃ (0.82 g, 0.39 mmol). The reaction was stirred for 3 hours, quenched with water, and extracted with DCM (2×20 ml). The combined organic fractions were dried over Na₂SO₄, filtered, and then concentrated. The resulting crude imine was dissolved in MeOH (5 ml) and NaBH₄ (0.06 g, 0.4 mmol) was added. The reaction was stirred for 10 min, quenched with aq. Na₂CO₃ (10 ml), and extracted with DCM (2×20 ml). The combined organic fractions were dried over Na₂SO₄, filtered, and then concentrated. The resulting oil was purified by reverse phase column chromatography (5-35% ACN) to give the title compound (0.05 g, 48%). $^1$H NMR (400 MHz, CD₃OD) δ 7.41-7.38 (m, 2H), 7.10 (d, J=9.2 Hz, 1H), 7.02-6.98 (m, 2H), 6.00-5.52 (br s, 1H), 5.05 (s, 1H), 3.63 (s, 2H), 2.37 (s, 3H), 1.87-1.82 (m, 1H), 1.51 (d, J=6.9 Hz, 3H), 0.93-0.91 (m, 2H), 0.67-0.63 (m, 2H). MS: Calcd.: 398. Found: [M+H]⁺ 399.

Example 108

(R)-6-(5-Cyclopropyl-1H-pyrazol-3-ylamino)-5-fluoro-2-(1-(4-fluorophenyl)ethylamino) nicotinonitrile A solution of 2-chloro-6-(5-cyclopropyl-1H-pyrazol-3-ylamino)-5-fluoro nicotinonitrile (Method 1, 0.3 g, 1.0 mmol) and (R)-1-(4-fluorophenyl)ethanamine (0.3 g, 2.1 mmol) was added to n-BuOH (2 ml) and DIEA (0.18 g, 1.4 mmol) in a sealed tube. The reaction was heated to 140° C. for 48 hours, then cooled to room temperature and concentrated. The resulting residue was purified by column chromatography (DCM-MeOH=80:1) to give the title compound (0.11 g, 26%). $^1$H NMR (400 MHz, CDCl₃) δ 8.44 (br s, 1H), 7.37-7.33 (m, 2H), 7.27 (d, J=9.6 Hz, 1H), 7.07-7.03 (m, 2H), 6.11 (s, 1H), 5.24-5.20 (m, 2H), 1.87-1.83 (m, 1H), 1.60 (d, J=6.2 Hz, 3H), 1.01-0.98 (m, 2H), 0.79-0.65 (m, 2H). MS: Calcd.: 380. Found: [M+H]⁺ 381.

Example 109

(S)—N-((6-(5-Cyclopropyl-1H-pyrazol-3-ylamino)-5-fluoro-2-(1-(4-fluorophenyl)ethylamino) pyridin-3-yl)methyl)-1,1,1-trifluoromethanesulfonamide To a solution of (S)-3-(aminomethyl)-N⁶-(5-cyclopropyl-1H-pyrazol-3-yl)-5-fluoro-N²-(1-(4-fluorophenyl)ethyl)pyridine-2,6-diamine (Example 3, 0.10 g, 0.26 mmol) in THF (5 ml) at room temperature was added 1.1 equivalent of trifluoromethylsulfonyl chloride loaded TFP resin, and DMAP (0.031 g, 0.26 mmol). The reaction was then stirred at room temperature for 15 hours and filtered. The remaining resin was then washed with THF (2×10 ml for 20 min), and then combined organic fractions were concentrated. The resulting oil was purified by reverse-phase column chromatography (5-50% ACN) to give the title compound (0.02 g, 15%). $^1$H NMR (400 MHz, CD₃OD) δ7.40-7.37 (m, 2H), 7.17 (d, J=10.9 Hz, 1H), 7.02-6.97 (m, 2H), 5.90-5.60 (br s, 1H), 5.14-5.12 (m, 1H), 4.28-4.25 (m, 2H), 1.88-1.84 (m, 1H), 1.54 (d, J=7.0 Hz, 3H), 0.95-0.93 (m, 2H), 0.67-0.64 (m, 2H). MS: Calcd.: 516. Found: [M+H]⁺ 517.

Example 110

(S)-6-(5-Cyclopropyl-1H-pyrazol-3-ylamino)-5-fluoro-2-(1-(5-fluoropyridin-2-yl)ethylamino) nicotinonitrile A suspension of 6-(5-cyclopropyl-1H-pyrazol-3-ylamino)-2,5-difluoronicotinonitrile (Method 32, 5.75 g, 22.0 mmol), in n-BuOH (28.75 ml) was prepared at room temperature in a 48 ml sealed tube. DIEA (4.98 ml, 28.6 mmol) was then added, followed by the addition of (S)-1-(5-fluoropyridin-2-yl)ethanamine (Method 33; 4.0 g, 28.6 mmol). The tube was then sealed, and the suspension was heated to 130° C. over 45 minutes. The reaction was then allowed to stir at 130° C. for 18 hours. The reaction was then cooled to room temperature and concentrated by rotary evaporation at 60° C. to remove n-BuOH. The remaining oil was then taken up in DCM (100 ml) and washed with water (2×100 ml). The combined aqueous fractions were then extracted with DCM (100 ml), and the combined organic fractions were dried over Na₂SO₄, filtered and concentrated. The resulting oil was then purified by column chromatography (DCM, then DCM-MeOH=100:1) to give the title compound (5.2 g, 62%). $^1$H NMR (400 MHz, CD₃OD) δ 8.43 (d, J=2.5 Hz, 1H), 7.60-7.34 (m, 3H), 6.09-5.63 (m, 1H), 5.24 (q, J=7.0 Hz, 1H), 1.91 (septet, 1H), 1.58 (d, J=6.6 Hz, 3H), 1.08-0.90 (m, 2H), 0.79-0.70 (m, 2H). MS: Calcd.: 381. Found: [M+H]⁺ 382.

Example 111

(S)—N²-(5-Cyclopropyl-1H-pyrazol-3-yl)-3-fluoro-N⁶-(1-(4-fluorophenyl)ethyl)-5-isopropylpyridine-2,6-diamine To a solution of (S)-6-(5-cyclopropyl-1H-pyrazol-3-ylamino)-5-fluoro-2-(1-(4-fluorophenyl)ethylamino)nicotinaldehyde (Example 73, 0.15 g, 0.39 mmol) in THF (6 ml) at 0° C. was added methyl magnesiumbromide (1.4 M THF, 0.50 mmol). The reaction was then stirred for 4 hours at room temperature, quenched with water, and extracted with DCM (2×20 ml). The combined organic fractions were dried over $Na_2SO_4$, filtered, and then concentrated. The resulting oil was purified by reverse phase column chromatography (5-50% ACN) to give the title compound (0.10 g, 64%). $^1$H NMR (400 MHz, $CD_3OD$) δ 7.40-7.37 (m, 2H), 7.12 (d, J=11.9 Hz, 1H), 7.02-6.97 (m, 2H), 5.70 (s, 1H), 5.17-5.12 (m, 1H), 2.99-2.96 (m, 1H), 1.87-1.82 (m, 1H), 1.54 (d, J=7.0 Hz, 3H), 1.23-1.21 (m, 6H), 0.94-0.90 (m, 2H), 0.66-0.63 (m, 2H). MS: Calcd.: 397. Found: [M+H]$^+$ 398.

Example 112

(S)-6-(5-Cyclopropyl-1H-pyrazol-3-ylamino)-5-fluoro-2-(1-(4-fluorophenyl)ethylamino)-4-(isopropylamino)nicotinonitrile To a solution of (S)-6-(5-cyclopropyl-1H-pyrazol-3-ylamino)-5-fluoro-2-(1-(4-fluorophenyl)ethylamino)-4-iodonicotinonitrile (Example 134, 0.07 g, 0.14 mmol) and DIEA (0.023 g, 0.18 mol) in n-BuOH (1.5 ml) was added isopropylamine (0.16 g, 2.7 mmol). The reaction was then heated to 185° C. under microwave conditions (1 hour×4 cycles). The reaction was then cooled to room temperature, DCM (10 ml) was added, and washed with 10% aqueous $Na_2S_2O_3$. The organic layer was then dried over $Na_2SO_4$, filtered, and then concentrated. The resulting oil was purified by reverse-phase column chromatography (5-50% ACN) to give the title compound (0.031 g, 51%). $^1$H NMR (400 MHz, $CD_3OD$) δ 7.36-7.33 (m, 2H), 7.04-7.00 (m, 2H), 5.99-5.59 (br s, 1H), 5.14 (s, 1H), 4.29-4.23 (m, 1H), 1.87-1.83 (m, 1H), 1.52 (d, J=7.0 Hz, 3H), 1.25 (d, J=6.2 Hz, 6H), 0.95-0.94 (m, 2H), 0.65-0.63 (m, 2H). MS: Calcd.: 437. Found: [M+H]$^+$ 438.

Example 113

(S)-6-(5-Cyclopropyl-1H-pyrazol-3-ylamino)-5-fluoro-2-(1-(4-fluorophenyl)ethylamino)-4-(methylamino)nicotinonitrile To a solution of (S)-6-(5-cyclopropyl-1H-pyrazol-3-ylamino)-5-fluoro-2-(1-(4-fluorophenyl)ethylamino)-4-iodonicotinonitrile (Example 134, 0.10 g, 0.19 mmol) and DIEA (0.03 g, 0.25 mol) in n-BuOH (1.5 ml) was added methylamine (2.0 M in THF, 1.9 mmol). The reaction was then heated to 185° C. under microwave conditions (1 hour×2 cycles). The reaction was then cooled to room temperature, DCM (10 ml) was added, and washed with 10% aqueous $Na_2S_2O_3$. The organic layer was then dried over $Na_2SO_4$, filtered, and then concentrated. The resulting oil was purified by reverse-phase column chromatography (5-50% ACN) to give the title compound (0.04 g, 49%). $^1$H NMR (400 MHz, $CD_3OD$) δ 7.35 (br s, 2H), 7.04-7.00 (m, 2H), 5.95 (br s, 1H), 5.14 (br s, 1H), 3.15 (d, J=2.7 Hz, 3H), 1.87-1.82 (m, 1H), 1.52 (d, J=6.8 Hz, 3H), 0.95-0.94 (m, 2H), 0.65-0.63 (m, 2H). MS: Calcd.: 409; Found: [M+H]$^+$ 410.

Example 114

(S)-5-Fluoro-2-(1-(4-fluorophenyl)ethylamino)-6-(5-methyl-1H-pyrazol-3-ylamino) nicotinonitrile A suspension of 2,5-difluoro-6-(5-methyl-1H-pyrazol-3-ylamino)nicotinonitrile (Method 41, 0.20 g, 0.85 mmol), DIEA (0.14 g, 1.1 mmol), and (S)-1-(4-fluorophenyl)ethanamine (0.23 g, 1.7 mmol) in n-BuOH (2 ml) was heated to 130° C. for 18 hours. The reaction was then cooled to room temperature, diluted with water (20 ml), and extracted with DCM (2×50 ml). The combined organic fractions were dried over $Na_2SO_4$, filtered, and then concentrated. The resulting oil was purified by column chromatography (DCM-MeOH=100:1) to give the title compound (0.27 g, 91%). $^1$H NMR (400 MHz, $CD_3OD$) δ 7.38-7.32 (m, 3H), 7.03-6.99 (m, 2H), 5.99 (br s, 1H), 5.15-5.14 (m, 1H), 2.24 (s, 3H), 1.53 (d, J=6.8 Hz, 3H). MS: Calcd.: 354. Found: [M+H]$^+$ 355.

Example 115

(S)-5-Fluoro-2-(1-(5-fluoropyridin-2-yl)ethylamino)-6-(5-methyl-1H-pyrazol-3-ylamino) nicotinonitrile A suspension of 2,5-difluoro-6-(5-methyl-1H-pyrazol-3-ylamino)nicotinonitrile (Method 41, 0.24 g, 1.02 mmol), DIEA (0.17 g, 1.3 mmol), and (S)-1-(5-fluoropyridin-2-yl)ethanamine (Method 33, 0.21 g, 1.5 mmol) in n-BuOH (2 ml) was heated to 130° C. for 18 hours. The reaction was cooled to room temperature, diluted with water (20 ml), and extracted with DCM (2×50 ml). The combined organic fractions were dried over $Na_2SO_4$, filtered, and then concentrated. The resulting oil was purified by column chromatography (DCM-MeOH 100:1) to give the title compound (0.20 g, 55%). $^1$H NMR (400 MHz, $CD_3OD$) δ 8.42 (s, 1H), 7.51-7.38 (m, 3H), 6.01 (s, 1H), 5.21-5.19 (m, 1H), 2.27 (s, 3H), 1.58 (d, J=6.7 Hz, 3H). MS: Calcd.: 355. Found: [M+H]$^+$ 356.

Example 116

(S)-6-(5-Cyclopropyl-1H-pyrazol-3-ylamino)-5-fluoro-2-(1-(5-fluoropyridin-2-yl)ethylamino) nicotinamide A solution of (S)-6-(5-cyclopropyl-1H-pyrazol-3-ylamino)-5-fluoro-2-(1-(5-fluoropyridin-2-yl)ethylamino) nicotinonitrile (Example 110, 0.24 g, 0.62 mmol) in MeOH (20 ml) was prepared at room temperature. An aqueous solution (0.7 ml) of KOH (0.17 g, 3.15 mmol) was then added dropwise, followed by the addition of 0.05 ml of 30% $H_2O_2$. The reaction was then heated to 65° C. for 3 hours, cooled to room temperature, and concentrated. The resulting residue was dissolved in EtOAc (50 ml), and washed with water (50 ml). The organic fraction was then dried over $Na_2SO_4$, filtered, and then concentrated. The resulting oil was purified by column chromatography (DCM-MeOH=30:1) to give the title compound (0.13 g, 52%). $^1$H NMR (400 MHz, $CD_3OD$) δ 8.42 (s, 1H), 7.70 (d, J=12.1 Hz, 1H), 7.48-7.38 (m, 2H), 6.02 (s, 1H), 5.25-5.02 (m, 1H), 1.91-1.86 (m, 1H), 1.57 (d, J=7.0 Hz, 3H), 0.97 (br s, 2H), 0.73 (br s, 2H). MS: Calcd.: 399. Found: [M+H]$^+$ 400.

Example 117

(S)—N-((6-(5-Cyclopropyl-1H-pyrazol-3-ylamino)-5-fluoro-2-((S)-1-(4-fluorophenyl) ethylamino)pyridin-3-yl)methyl)-5-oxopyrrolidine-2-carboxamide To a DCM (10 ml) solution of (S)-3-(aminomethyl)-N$^6$-(5-cyclopropyl-1H-pyrazol-3-yl)-5-fluoro-N$^2$-(1-(4-fluorophenyl)ethyl)pyridine-2,6-diamine (Example 3, 0.45 g, 1.17 mmol) and HBTU (0.44 g, 1.17 mmol) cooled at 0° C. was added a solution of (S)-5-oxopyrrolidine-2-carboxylic acid (0.15 g, 1.17 mmol) in DMF (5 ml), followed by the addition of DIEA (0.14 g, 1.17 mmol). The reaction was then stirred at room temperature for 1 hour and quenched with 20 ml of aqueous NaHCO$_3$, and extracted with DCM (2×30 ml). The combined organic fractions were dried over Na$_2$SO$_4$, filtered, and then concentrated. The resulting oil was purified by column chromatography (DCM-MeOH=20:1) to give the title compound (0.30 g, 51%). $^1$H NMR (400 MHz, CD$_3$OD) δ 7.35-7.32 (m, 2H), 7.10 (d, J=10.9 Hz, 1H), 7.00-6.96 (m, 2H), 5.80-5.65 (br s, 1H), 5.06-5.05 (m, 1H), 4.30-4.15 (m, 3H), 2.45-2.24 (m, 3H), 2.05-2.00 (m, 1H), 1.85-1.80 (m, 1H), 1.48 (d, J=6.8 Hz, 3H), 0.91-0.89 (m, 2H), 0.63-0.62 (m, 2H). MS: Calcd.: 495. Found: [M+H]$^+$ 496.

Example 118

(R)—N-((6-(5-Cyclopropyl-1H-pyrazol-3-ylamino)-5-fluoro-2-((S)-1-(4-fluorophenyl) ethylamino)pyridin-3-yl)methyl)-5-oxopyrrolidine-2-carboxamide To a DCM (10 ml) solution of (S)-3-(aminomethyl)-N$^6$-(5-cyclopropyl-1H-pyrazol-3-yl)-5-fluoro-N$^2$-(1-(4-fluorophenyl)ethyl)pyridine-2,6-diamine (Example 3; 0.45 g, 1.17 mmol) and HBTU (0.44 g, 1.17 mmol) cooled at 0° C. was added a solution of (R)-5-oxopyrrolidine-2-carboxylic acid (0.15 g, 1.17 mmol) in DMF (5 ml), followed by the addition of DIEA (0.14 g, 1.17 mmol). The reaction was then stirred at room temperature for 1 hour and quenched with 20 ml aqueous NaHCO$_3$, and extracted with DCM (2×30 ml). The combined organic fractions were dried over Na$_2$SO$_4$, filtered, and then concentrated. The resulting oil was purified by column chromatography (DCM-MeOH=20:1) to give the title compound (0.25 g, 43%). $^1$H NMR (400 MHz, CD$_3$OD) δ 7.37-7.34 (m, 2H), 7.14 (d, J=10.9 Hz, 1H), 7.02-6.97 (m, 2H), 5.80-5.65 (br s, 1H), 5.07 (br s, 1H), 4.33-4.16 (m, 3H), 2.46-2.22 (m, 3H), 2.05-1.98 (m, 1H), 1.88-1.81 (m, 1H), 1.51 (d, J=6.8 Hz, 3H), 0.93-0.92 (m, 2H), 0.66-0.62 (m, 2H). MS: Calcd.: 495. Found: [M+H]$^+$ 496.

Example 119

(S)-5-Fluoro-2-(1-(5-fluoropyridin-2-yl)ethylamino)-6-(5-isopropoxy-1H-pyrazol-3-ylamino) nicotinonitrile A solution of 2,5-difluoro-6-(5-isopropoxy-1H-pyrazol-3-ylamino)nicotinonitrile (Method 42, 0.30 g, 1.07 mmol), DIEA (0.16 g, 1.29 mmol), and (S)-1-(5-fluoropyridin-2-yl) ethanamine (Method 33; 0.22 g, 1.6 mmol) in n-BuOH (3 ml) was heated to 130° C. for 18 hours. The reaction was then cooled to room temperature, diluted with water (20 ml), and extracted with DCM (2×50 ml). The combined organic fractions were dried over Na$_2$SO$_4$, filtered, and then concentrated. The resulting oil was purified by column chromatography (hexanes-EtOAc=3:1) to give the title compound (0.25 g, 58%). $^1$H NMR (400 MHz, CD$_3$OD) δ 8.40 (s, 1H), 7.56-7.55 (m, 2H), 7.45 (d, J=10.5 Hz, 1H), 5.42 (s, 1H), 5.25-5.22 (m, 1H), 4.63 (br s, 1H), 1.60 (d, J=7.0 Hz, 3H), 1.34 (d, J=6.1 Hz, 6H). MS: Calcd.: 399. Found: [M+H]$^+$ 400.

Example 120

6-[(5-Cyclopropyl-1H-pyrazol-3-yl)amino]-2-{[(1S)-1-(3,5-difluoropyridin-2-yl)ethyl]amino}-5-fluoronicotinonitrile Following a similar procedure to the synthesis of Example 1, the title compound was synthesized from 6-[(5-cyclopropyl-1H-pyrazol-3-yl)amino]-2,5-difluoronicotinonitrile (Method 32) and (S)-1-(3,5-difluoropyridin-2-yl)ethanamine (Method 50). $^1$H NMR (400 MHz) δ 0.68 (m, 2H), 0.95 (m, 2H), 1.45 (d, J=6 Hz, 3H), 1.87 (m, 1H), 5.48 (m, 1H), 6.19 (s, 1H), 6.69 (m, 1H), 7.63 (d, 1H), 7.98 (m, 1H), 8.51 (s, 1H), 9.58 (s, 1H), 12.15 (s, 1H). MS: Calcd.: 399. Found: [M+H]$^+$ 400.

Example 121

(S)-5-Chloro-6-(5-cyclopropyl-1H-pyrazol-3-ylamino)-2-(1-(5-fluoropyrimidin-2-yl)ethylamino) nicotinonitrile A mixture of 2,5-dichloro-6-(5-cyclopropyl-1H-pyrazol-3-ylamino)nicotinonitrile (Method 43, 0.17 g, 0.58 mmol), (S)-1-(5-fluoropyrimidin-2-yl)ethanamine HCl salt (Method 55, 0.186 g, 0.87 mmol), and DIEA (0.60 ml, 3.5 mmol) in n-BuOH (3 ml) was heated in a sealed tube at 130° C. for 44 hours. The solvent was removed under reduced pressure and the residue was purified by column chromatography (hexane-EtOAc=1:1) to give the title compound as a white solid (0.095 g, 41%). $^1$H NMR (400 MHz) δ 12.16 (s, 1H), 8.88 (s, 2H), 8.52 (s, 1H), 7.84 (s, 1H), 7.05 (d, J=7.2 Hz, 1H), 5.98 (s, 1H), 5.28 (m, 1H), 1.84 (m, 1H), 1.57 (d, J=7.2 Hz, 3H), 0.96 (m, 2H), 0.71 (m, 2H). MS: Calcd.: 398. Found: [M+H]$^+$ 399.

Example 122

N-{5-[(1R)-1-({3-Cyano-6-[(5-cyclopropyl-1H-pyrazol-3-yl)amino]-5-fluoropyridin-2-yl}amino) ethyl]-2-fluorophenyl}methanesulfonamide and Example 123

N-{5-[(1S)-1-({3-Cyano-6-[(5-cyclopropyl-1H-pyrazol-3-yl)amino]-5-fluoropyridin-2-yl}amino)ethyl]-2-fluorophenyl}methanesulfonamide To a 10-ml microwave vessel was added, 2-chloro-6-[(5-cyclopropyl-1H-pyrazol-3-yl)amino]-5-fluoronicotinonitrile (Method 1, 600 mg, 2.3 mmol), N-[5-(1-aminoethyl)-2-fluorophenyl]methanesulfonamide (Method 61, 500 mg, 2.3 mmol), DIEA (0.5 ml, 2.76 mmol), and n-butanol (5 ml). The vessel was sealed and subjected to microwave heating at 150° C. for 5 hours (CEM Discover System). The resulting mixture was then purified by silica gel chromatography using 5% MeOH/DCM. The racemic product obtained was then chirally purified by HPLC on Chiralcel OJ column (500×50 mm, 20 microns) using 50:25:25:0.1% of hexane/MeOH/EtOH/diethylamine at 118 ml/min. The chiral purification gave 220 mg of N-{5-[(1R)-1-({3-cyano-6-[(5-cyclopropyl-1H-pyrazol-3-yl)amino]-5-fluoropyridin-2-yl}amino) ethyl]-2-fluorophenyl}methanesulfonamide $^1$H NMR: δ 11.77-12.26 (br s, 1H), 9.51 (s, 1H), 9.34-9.48 (br s, 1H), 7.62 (d, J=10.55 Hz, 1H), 7.39 (d, J=8.29 Hz, 1H), 7.02-7.23 (m, 3H), 6.00 (s, 1H), 5.07-5.24 (m, 1H), 2.95 (s, 3H), 1.81-1.95 (m, 1H), 1.49 (d, J=7.54 Hz, 3H), 0.88-0.97 (m, 2H), 0.57-0.68 (m, 2H). MS: Calcd.: 473. Found: [M+H]$^+$ 474 and 223 mg of N-{5-[(1S)-1-({3-cyano-6-[(5-cyclopropyl-1H-pyrazol-3-yl)amino]-5-fluoropyridin-2-yl}amino)ethyl]-2-fluorophenyl}methanesulfonamidel; $^1$H NMR: 11.73-12.38 (br s, 1H), 9.42 (s, 1H), 8.41-9.12 (br s, 1H), 7.61 (d, J=11.30 Hz, 1H), 7.37 (d, J=7.54 Hz, 1H), 6.96-7.24 (m, 3H), 6.02 (s, 1H), 5.05-5.26 (m, 1H), 2.90 (s, 3H), 1.79-1.96 (m, 1H), 1.49 (d, J=6.78 Hz, 3H), 0.89-0.98 (m, 2H), 0.59-0.67 (m, 2H). MS: Calcd.: 473. Found: [M+H]$^+$ 474.

Example 124

5-Chloro-2-{[(1S)-1-(5-fluoropyridin-2-yl)ethyl]
amino}-6-[(5-methyl-1H-pyrazol-3-yl)amino]nicotinonitrile To a 10-ml microwave vessel was added, 2,5-dichloro-6-[(5-methyl-1H-pyrazol-3-yl)amino]nicotinonitrile (Method 60, 8 mmol), [(1S)-1-(5-fluoropyridin-2-yl)ethyl]amine (Method 33, 8 mmol, 97 wt % solution in dioxane), DIEA (0.3 ml, 1.66 mmol), and n-butanol (4 ml). The vessel was then sealed and subjected to microwave heating at 150° C. for 3 hours. After 3 hours, more 2-pyridyl amine (100 mg, 0.69 mmol) was added. The resulting mixture was purified by silica gel chromatography (Biotage Horizon System) using an isocratic system of 15:0.5:0.5% of DCM/EtOAc/MeOH to give 312 mg of the title compound. $^1$H NMR: 12.04 (br s, 1H), 8.41-8.63 (m, 2H), 7.84 (s, 1H), 7.56-7.71 (m, 1H), 7.40 (dd, J=8.67, 4.14 Hz, 1H), 7.28 (s, 1H), 5.86 (s, 1H), 5.06-5.25 (m, 1H), 2.17 (s, 3H), 1.51 (d, J=7.54 Hz, 3H). MS: Calcd.: 371/373. Found: [M+H]$^+$ 372/374.

Example 125

N-{5-[1-({3-Cyano-6-[(5-cyclopropyl-1H-pyrazol-3-yl)amino]-5-fluoropyridin-2-yl}amino)ethyl]-2-fluorophenyl}acetamide To a 10-ml microwave reaction vessel was added, 6-[(5-cyclopropyl-1H-pyrazol-3-yl)amino]-2,5-difluoronicotinonitrile (Method 32, 300 mg, 1.13 mmol), N-[5-(1-aminoethyl)-2-fluorophenyl]acetamide (Method 66, 331 mg, 1.7 mmol), and DIEA (0.8 ml, 4.6 mmol) in n-butanol (4 ml). The resulting suspension was set to microwave heating (CEM Discover System) at 150° C. for 3 hours. The reaction was concentrated in vacuo and purified by silica gel chromatography (Biotage Horizon System) using a gradient elution of 25-35% EtOAc (20% v/v MeOH) in hexanes to give 180 mg (36% isolated yield) of the title compound. $^1$H NMR: 9.66 (br s, 1H) 9.43 (s, 1H) 7.81 (d, J=6.03 Hz, 2H) 7.60 (d, J=11.30 Hz, 1H) 6.92-7.21 (m, 3H) 5.98 (s, 1H) 5.13 (t, J=7.16 Hz, 1H) 2.05 (s, 3H) 1.76-1.92 (m, 1H) 1.46 (d, J=6.78 Hz, 3H) 0.82-0.95 (m, J=8.29 Hz, 2H) 0.54-0.66 (m, 2H). MS: Calcd.: 437. Found: [M+H]$^+$ 438.

Example 126

N-{5-[1-({3-Cyano-6-[(5-cyclopropyl-1H-pyrazol-3-yl)amino]-5-fluoropyridin-2-yl}amino)ethyl]-2-fluorophenyl}cyclopropanecarboxamide To a 10-ml microwave reaction vessel was added 6-[(5-cyclopropyl-1H-pyrazol-3-yl)amino]-2,5-difluoronicotinonitrile (Method 32, 431 mg, 1.65 mmol), N-[5-(1-aminoethyl)-2-fluorophenyl]cyclopropanecarboxamide (Method 69, 550 mg, 2.5 mmol), and DIEA (1.15 ml, 6.6 mmol) in n-butanol (5 ml). The resulting suspension was set to microwave heating (CEM Discover System) at 150° C. for 3 hours. The reaction was concentrated in vacuo and purified by silica gel chromatography (Biotage Horizon System) using a gradient elution of 25-35% EtOAc (20% v/v MeOH) in hexanes to give 267 mg (35% isolated yield) of the title compound. $^1$H NMR: 11.99 (s, 1H) 9.91 (s, 1H) 9.42 (s, 1H) 7.88 (d, J=6.03 Hz, 1H) 7.59 (d, J=10.55 Hz, 1H) 6.95-7.20 (m, 3H) 5.99 (s, 1H) 5.02-5.21 (m, 1H) 1.89-2.03 (m, 1H) 1.76-1.89 (m, 1H) 1.45 (d, J=7.54 Hz, 3H) 0.87 (t, J=8.67 Hz, 2H) 0.75 (d, J=6.03 Hz, 4H) 0.54-0.66 (m, 2H). MS: Calcd.: 463. Found: [M+H]$^+$ 464.

Example 127

6-[(5-Cyclopropyl-1H-pyrazol-3-yl)amino]-5-fluoro-2-{[(1S)-1-(6-fluoropyridin-3-yl)ethyl]
amino}nicotinonitrile and

Example 128

6-[(5-Cyclopropyl-1H-pyrazol-3-yl)amino]-5-fluoro-2-{[(1R)-1-(6-fluoropyridin-3-yl)ethyl]
amino}nicotinonitrile To a 10-ml microwave reaction vessel was added 6-[(5-cyclopropyl-1H-pyrazol-3-yl)amino]-2,5-difluoronicotinonitrile (Method 32, 1 g, 4 mmol), 1-(6-fluoropyridin-3-yl)ethanamine (Method 76, 560 mg, 4 mmol), and DIEA (0.84, 4.8 mmol) in n-butanol (5 ml). The resulting suspension was set to microwave heating (CEM Discover System) at 150° C. for 3 hours. The reaction was then concentrated in vacuo and purified by silica gel chromatography (Biotage Horizon System) using a gradient elution of 1-4% MeOH in DCM to give 380 mg (25% isolated yield) of 6-[(5-cyclopropyl-1H-pyrazol-3-yl)amino]-5-fluoro-2-{[1-(6-fluoropyridin-3-yl)ethyl]amino}nicotinonitrile. The racemic product obtained was then chirally purified by HPLC on Chiralpak AS column (500×50 mm, 20 microns) using 80:10:10:0.1% of hexane-MeOH-EtOH-diethylamine at 118 ml/min. The chiral purification gave 145 mg of 6-[(5-cyclopropyl-1H-pyrazol-3-yl)amino]-5-fluoro-2-{[(1S)-1-(6-fluoropyridin-3-yl)ethyl]amino}nicotinonitrile: $^1$H NMR: 9.43 (s, 1H) 8.08 (s, 1H) 7.84-8.00 (m, 1H) 7.61 (d, J=11.30 Hz, 1H) 7.18 (d, J=7.54 Hz, 1H) 7.04-7.13 (m, 1H) 5.94 (s, 1H) 5.15 (t, J=7.54 Hz, 1H) 1.81-1.97 (m, 1H) 1.51 (d, J=7.54 Hz, 3H) 0.92 (d, J=6.03 Hz, 2H) 0.64 (s, 2H). MS: Calcd.: 381. Found: [M+H]$^+$ 382; and 137 mg of 6-[(5-cyclopropyl-1H-pyrazol-3-yl)amino]-5-fluoro-2-{[(1R)-1-(6-fluoropyridin-3-yl)ethyl]
amino}nicotinonitrile: $^1$H NMR: 9.42 (s, 1H) 8.08 (s, 1H) 7.93 (t, J=8.29 Hz, 1H) 7.61 (d, J=10.55 Hz, 1H) 7.18 (d, J=8.29 Hz, 1H) 7.08 (dd, J=8.29, 3.01 Hz, 1H) 5.94 (s, 1H) 5.15 (t, J=7.54 Hz, 1H) 1.81-1.96 (m, 1H) 1.51 (d, J=7.54 Hz, 3H) 0.91 (d, J=8.29 Hz, 2H) 0.64 (s, 2H). MS: Calcd.: 381. Found: [M+H]$^+$ 382.

Example 129

5-Fluoro-2-{[1-(5-fluoropyrimidin-2-ylethyl]
amino}-6-[(5-methyl-1H-pyrazol-3-yl)amino]nicotinonitrile A mixture of 1-(5-fluoropyrimidin-2-yl)ethanamine (Method 72, 0.05 g, 0.35 mmol), 2,5-difluoro-6-[(5-methyl-1H-pyrazol-3-yl)amino]nicotinonitrile (Method 41, 0.06 g, 0.25 mmol), and DIEA (0.12 ml, 0.7 mmol) in n-BuOH (3 ml) was charged into a microwave reaction vessel. The vessel was sealed and heated in microwave reactor at 160° C. for 6 hours. The solvent was removed under reduced pressure and the residue was purified by silica gel chromatography (DCM-EtOAc=1:1) to give the title compound as a yellow solid (0.016 g, 15%). LC-MS, 357 (M+1). $^1$H NMR (400 MHz, MeOD) δ 8.70 (s, 2H), 7.45 (d, 1H), 6.40 (br, 1H), 5.45 (q 1H), 2.35 (s, 3H), 1.65 (d, 3H).

Example 130

5-Chloro-2-{[1-(5-fluoropyrimidin-2-yl)ethyl]amino}-6-[(5-methyl-1H-pyrazol-3-yl)amino]nicotinonitrile A mixture of 1-(5-fluoropyrimidin-2-yl)ethanamine (Method 72, 0.05 g, 0.35 mmol), 2,5-dichloro-6-[(5-methyl-1H-pyrazol-3-yl)amino]nicotinonitrile (Method 60, 0.06 g, 0.25 mmol), and DIEA (0.12 ml, 0.7 mmol) in n-BuOH (10 ml) was charged into a microwave reaction vessel. The vessel was sealed and heated in microwave reactor at 160° C. for 6 hours. The solvent was removed under reduced pressure and the residue was purified by silica gel chromatography (DCM-EtOAc=1:1) to give the title compound as a yellow solid (0.017 g, 15%). LC-MS, 373 (M+1). $^1$H NMR (400 MHz, MeOD) δ 8.75 (s, 2H), 7.45 (s, 1H), 6.40 (s, 1H), 5.45 (br 1H), 2.35 (s, 3H), 1.60 (d, 3H).

Example 131

N-{5-[(1S)-1-({3-Cyano-5-fluoro-6-[(5-methyl-1H-pyrazol-3-yl)amino]pyridin-2-yl}amino)ethyl]-2-fluorophenyl}methanesulfonamide and

Example 132

N-{5-[(1R)-1-({3-Cyano-5-fluoro-6-[(5-methyl-1H-pyrazol-3-yl)amino]pyridin-2-yl}amino)ethyl]-2-fluorophenyl}methanesulfonamide A mixture of N-[5-(1-aminoethyl)-2-fluorophenyl]methanesulfonamide (Method 61, 0.2 g, 0.86 mmol), 2,5-difluoro-6-[(5-methyl-1H-pyrazol-3-yl)amino]nicotinonitrile (Method 41, 0.2 g, 0.8 mmol), and DIEA (0.3 ml, 2.1 mmol) in n-BuOH (4 ml) was charged into a microwave reaction vessel. The vessel was sealed and heated in microwave reactor at 160° C. for 6 hours. The solvent was removed under reduced pressure and the residue was purified by silica gel chromatography (DCM-EtOAc=1:1) to give the title compound as a yellow solid (0.16 g, 35%). The resulting racemic compound was separated by a Chiralpak AS-H SFC HPLC column (25% MeOH) to two enantiomers (The retention time of the first elute Example 131 (S-isomer) was 7 min, and the retention time of the second elute Example 132 (R-isomer) was 8.5 min). LC-MS, 448 (M+1). $^1$H NMR (400 MHz, MeOD) δ 7.45 (d, 1H), 7.40 (d, 1H), 7.20 (s, 1H), 7.10 (t, 1H), 6.00 (s, 1H), 5.20 (br 1H), 2.90 (s, 3H), 2.20 (s, 3H), 1.60 (d, 3H).

Example 133

5-Fluoro-2-{[1-(5-fluoropyrimidin-2-yl)ethyl]amino}-6-[(5-isopropoxy-1H-pyrazol-3-yl)amino]nicotinonitrile A mixture of 1-(5-fluoropyrimidin-2-yl)ethanamine (Method 72, 0.05 g, 0.35 mmol), 2,5-difluoro-6-[(5-methyl-1H-pyrazol-3-yl)amino]nicotinonitrile (Method 41, 0.05 g, 0.25 mmol), and DIEA (0.12 ml, 0.7 mmol) in n-BuOH (4 ml) was charged into a microwave reaction vessel. The vessel was sealed and heated in microwave reactor at 160° C. for 6 hrs. The solvent was removed under reduced pressure and the residue was purified by silica gel chromatography (DCM-EtOAc=1:1) to give the title compound as a yellow solid (0.006 g, 5%). LC-MS, 401 (M+1). $^1$H NMR (400 MHz, MeOD) δ 8.70 (s, 2H), 7.50 (d, 1H), 5.50 (s, 1H), 5.45 (br, 1H), 4.60 (m, 1H), 1.60 (d, 3H), 1.25 (d, 6H).

Example 134

(S)-6-(5-Cyclopropyl-1H-pyrazol-3-ylamino)-5-fluoro-2-(1-(4-fluorophenyl)ethylamino)-4-iodonicotinonitrile A solution of 2-chloro-6-(5-cyclopropyl-1H-pyrazol-3-ylamino)-5-fluoro-4-iodonicotinonitrile (Method 39, 0.28 g, 0.69 mmol), (S)-1-(4-fluorophenyl)ethanamine (0.19 g, 1.3 mmol), and DIEA (0.11 g, 0.90 mmol) in n-BuOH (1 ml) was heated to 140° C. for 18 hours. The reaction was diluted with water (10 ml), extracted with DCM (2×20 ml) and the combined organic fractions were dried over Na$_2$SO$_4$, filtered, and then concentrated. The resulting oil was purified by column chromatography (DCM-MeOH=100:1) to give the title compound (0.07 g, 20%). MS: Calcd.: 506. Found: [M+H]$^+$ 507.

Preparation of Starting Materials

Method 1

2-Chloro-6-(5-cyclopropyl-1H-pyrazol-3-ylamino)-5-fluoronicotinonitrile

A solution of 5-cyclopropyl-1H-pyrazol-3-amine (1.9 g, 16.0 mmol) in CH$_3$CN (20 ml) was added dropwise to a solution of 2,6-dichloro-5-fluoronicotinonitrile (3.0 g, 16.0 mmol) and triethylamine (2.1 g, 20.0 mmol) in CH$_3$CN (80 ml) at 25° C. The resulting solution was then heated to 82° C. for 18 hrs, and then cooled to 25° C., at which point the product precipitated from solution. The resulting solid was filtered, and washed with CH$_3$CN (100 ml) to give the title compound (3.2 g, 73%). MS: Calcd.: 277. Found: [M+H]$^+$ 278.

Method 2

2-Chloro-5-fluoro-6-(5-isopropoxy-1H-pyrazol-3-ylamino)nicotinonitrile

A solution of 5-isopropoxy-1H-pyrazol-3-amine (0.96 g, 6.8 mmol), 2,6-dichloro-5-fluoronicotinonitrile (1.3 g, 6.8 mmol), and triethylamine (0.9 g, 8.8 mmol) in THF (30 ml) was heated to 60° C. for 4 days, and then cooled to 25° C., at which point the product precipitated. The resulting solid was filtered and washed with hexanes (100 ml) to give the title compound (1.0 g, 50%). MS: Calcd.: 295. Found: [M+H]$^+$ 296.

Method 3

3,5,6-Trichloro-N-(5-cyclopropyl-1H-pyrazol-3-yl)pyridin-2-amine

A solution of 2,3,5,6-tetrachloropyridine (0.20 g, 0.9 mmol), 5-cyclopropyl-1H-pyrazol-3-amine (0.20 g, 1.8 mmol), and triethylamine (0.10 g, 1.4 mmol) in NMP (2 ml) was heated in a microwave at 200° C. for 30 min. The reaction was cooled to 25° C., quenched with water (10 ml), and extracted with MTBE (4×30 ml). The combined organic fractions were then dried, filtered, and concentrated. The resulting solid was purified by column chromatography (DCM-MeOH=50:1) to give the title compound (0.035 g, 12%). MS: Calcd.: 303. Found: [M+H]$^+$ 303.

Method 4

(2-Chloro-pyridin-4-yl)-(5-cyclopropyl-1H-pyrazole-3-yl)-amine

A mixture of 4-iodo-2-chloropyridine (0.26 g, 1.1 mmol), 3-amino-5-cyclopropyl-pyrazole-1-carboxylic acid tert-butyl ester (0.20 g, 0.89 mmol), Pd$_2$dba$_3$ (0.016 g, 2 mol %), Xantphos (0.031 g, 6 mol %), and Cs$_2$CO$_3$ (0.41 g, 1.3 mmol) in degassed toluene (4 ml) was purged with N$_2$ and heated to 100° C. in a sealed tube for 2 days. The mixture was diluted with THF and filtered to remove Cs$_2$CO$_3$. The filtrate was concentrated under reduced pressure and purified by column chromatography (hexane-EtOAc=3:1) to give the title compound (0.10 g, 48%). MS: Calcd.: 234. Found: [M+H]$^+$ 235.

Method 5

(S)-6-Chloro-N-(1-(4-fluorophenyl)ethyl)-3-nitropyridin-2-amine

To a mixture of 2,6-dichloro-3-nitropyridine (2.26 g, 10.8 mmol) and potassium carbonate (1.29 g, 9.34 mmol) in anhydrous CH$_3$CN (20 ml), was added (S)-1-(4-fluoro-phenyl)-ethylamine (1.00 g, 7.19 mmol) dropwise at 0° C. The reaction mixture was stirred at 25° C. for 17 hrs. The solid was removed by filtration and the resulted cake was washed with EtOAc (20 ml). The combined filtrate was concentrated and purified by column chromatography (hexane-EtOAc=10:1) to give the title compound as a yellow solid (1.74 g, 82%). $^1$H NMR (400 MHz) δ 8.65 (d, J=7.6 Hz, 1H), 8.43 (d, J=8.4 Hz, 1H), 7.51 (m, 2H), 7.16 (m, 2H), 6.81 (d, J=8.8 Hz, 1H), 5.37 (m, 1H), 1.59 (d, J=6.8 Hz, 3H).

Methods 6-9

Following a similar procedure to Method 5, the following compounds were synthesized from a 2,6-dichloro-3-nitropyridine by reacting it with an amine.

Method 11

2-(4-Fluorophenyl)-2-nitroproane-1,3-diol

To a solution of 1-fluoro-4-(nitromethyl)benzene (Method 12; 10.0 g, 80% pure; 52 mmol) and TEA (15.1 ml, 108.3 mmol) in dioxane (50 ml) was added formaldehyde (8.6 ml, 116 mmol) dropwise at 0° C. After addition, the reaction was slowly warmed up to 25° C. overnight. The solvent was removed under reduced pressure and the residue was purified by column chromatography (hexane:EtOAc=10:1) to give the title compound as a white solid (4.5 g, 41%). NMR (400 MHz) 7.41 (m, 2H), 7.22 (m, 2H), 5.39 (t, J=5.2 Hz, 2H), 4.22 (m, 4H).

Method 12

1-Fluoro-4-(nitromethyl)benzene

A mixture of 1-(bromomethyl)-4-fluorobenzene (11.52 g, 61 mmol) and AgNO$_2$ (11.3 g, 73 mmol) in benzene (200 ml) was stirred vigorously at 25° C. for 25 hrs. The solid was removed by filtration and washed with ether (500 ml). The combined organic was concentrated to give the title compound (10.0 g, 80% pure; 85%) which was used without further purification. NMR (400 MHz, CDCl$_3$) 7.44 (m, 2H), 7.18 (m, 2H), 5.42 (s, 2H).

Method 13

(S)-5,6-Chloro-N-(1-(4-fluorophenyl)ethyl)-3-nitropyridin-2-amine

To a mixture of 2,3,6-trichloro-5-nitropyridine (1.00 g, 4.40 mmol) and potassium carbonate (0.79 g, 5.7 mmol) in anhydrous acetonitrile (10 ml) was added (S)-1-(4-fluoro-

| Method | Product | NMR/MS | Amine |
|---|---|---|---|
| 6 | 6-Chloro-N-(4-fluorobenzyl)-3-nitropyridin-2-amine | (400 MHz, CDCl$_3$) 8.58 (br s, 1H), 8.37 (d, J = 8.4 Hz, 1H), 7.36 (m, 2H), 7.04 (m, 2H), 6.67 (d, J = 8.4 Hz, 1H), 4.78 (d, J = 5.6 Hz, 2H) | (4-fluoro-phenyl)methanamine |
| 7 | (2R)-2-[(6-Chloro-3-nitropyridin-2-yl)amino]-2-(4-fluorophenyl)ethanol | (400 MHz) 8.96 (d, J = 7.6 Hz, 1H), 8.46 (d, J = 8.4 Hz, 1H), 7.45 (m, 2H), 7.15 (m, 2H), 6.81 (d, J = 8.8 Hz, 1H), 5.27 (m, 2H), 3.80 (m, 2H) | (R)-2-amino-2-(4-fluorophenyl)ethanol |
| 8 | 2-[(6-Chloro-3-nitropyridin-2-yl)amino]-2-(4-fluorophenyl)propane-1,3-diol | (400 MHz) 9.13 (s, 1H), 8.44 (d, J = 8.4 Hz, 1H), 7.39 (m, 2H), 7.06 (m, 2H), 6.73 (d, J = 8.8 Hz, 1H), 5.16 (t, J = 5.6 Hz, 2H), 4.07 (m 2H), 3.96 (m, 2H). MS: Calcd.: 341; Found: [M + H]$^+$ 342 | Method 10 |
| 9 | 6-Chloro-N-[(1R)-1-(4-fluorophenyl)ethyl]-3-nitropyridin-2-amine | MS: Calcd.: 295; Found: [M + H]$^+$ 296 | (R)-1-(4-fluoro phenyl)ethanamine |

Method 10

2-Amino-2-(4-fluorophenyl)propane-1,3-diol

A suspension of 2-(4-fluorophenyl)-2-nitroproane-1,3-diol (Method 11; 4.5 g, 20.9 mmol) and Raney nickel (0.45 g, 5.23 mmol) in MeOH (50 ml) was degassed and stirred under H$_2$ (48 psi) for 2 hours. The catalyst was removed by filtration. The filtrate was concentrated and recrystallized from hexane:EtOAc (1:1) to give the title compound (2.35 g, 61%) as a white solid. NMR (400 MHz) 7.55 (m, 2H), 7.07 (m, 2H), 4.65 (t, J=5.2 Hz, 2H), 3.49 (m, 4H), 1.76 (s, 2H).

phenyl)-ethylamine (0.64 g, 4.62 mmol) dropwise at 0° C. After addition, the reaction mixture was stirred at 25° C. for 17 hours. The solid was removed by filtration and washed with EtOAc (20 ml). After evaporation of the solvent, the resulted residue was purified by column chromatography (hexane:EtOAc=10:1) to give the title compound as a yellow solid (0.61 g, 79% pure, 33%). NMR (400 MHz, CDCl$_3$) 8.46 (br s, 2H), 7.36 (m, 2H), 7.03 (m, 2H), 5.40 (m, 1H), 1.63 (d, J=6.8 Hz, 3H).

Methods 14-15

Following a similar procedure to Method 13, the following compounds were synthesized from a 2,3,6-trichloro-5-nitropyridine by reacting it with an amine.

| Method | Product | NMR/MS | Amine |
|---|---|---|---|
| 14 | (2R)-2-[(5,6-Dichloro-3-nitropyridin-2-yl)amino]-2-(4-fluorophenyl)ethanol | (400 MHz) 8.91 (d, J = 7.2 Hz, 1H), 8.66 (s, 1H), 7.45 (m, 2H), 7.15 (m, 2H), 5.25 (m, 2H), 3.80 (m, 2H) | (R)-2-amino-2-(4-fluoro phenyl)ethanol |
| 15 | 3,6-Dichloro-N-(5-cyclopropyl-1H-pyrazol-3-yl)-5-nitropyridin-2-amine | (400 MHz) 12.37 (s, 1H), 9.83 (s, 1H), 8.54 (s, 1H), 6.27 (s, 1H), 1.94 (m, 1H), 0.95 (m, 2H), 0.70 (m, 2H). MS: Calcd.: 313; Found: [M + H]+ 314 | 5-cyclopropyl-1H-pyrazol-3-amine |

Method 16

6-Chloro-N-(5-cyclopropyl-1H-pyrazol-3-yl)-3-nitropyridin-2-amine

To a solution of 2,6-dichloro-3-nitropyridine (0.67 g, 3.2 mmol) and DIEA (0.46 ml, 2.65 mmol) in EtOH (20 ml) was added 5-cyclopropyl-1H-pyrazol-3-amine (0.26 g, 2.12 mmol) solution in EtOH (5 ml) dropwise at 0° C. After addition, the reaction mixture was stirred at 25° C. for 24 hrs. The solvent was removed under reduced pressure and the resulted residue was purified by column chromatography (hexane-EtOAc=5:1) to give the title compound as a yellow solid (0.58 g, 98%). $^1$H NMR (400 MHz) δ12.36 (s, 1H), 10.20 (s, 1H), 8.54 (d, J=8.4 Hz, 1H), 7.01 (d, J=8.4 Hz, 1H), 6.39 (d, J=1.6 Hz, 1H), 1.94 (m, 1H), 0.96 (m, 2H), 0.71 (m, 2H). MS: Calcd.: 279. Found: [M+H]+ 280.

Method 17

5,6-Chloro-N-(5-cyclopropyl-1H-pyrazol-3-yl)-3-nitropyridine-2-amine

To a solution of 2,3,6-trichloro-5-nitropyridine (1.62 g, 7.10 mmol) and DIEA (1.24 ml, 7.1 mmol) in THF (25 ml) was added dropwise a solution of 5-cyclopropyl-1H-pyrazol-3-amine (0.70 g, 5.68 mmol) in THF (5 ml) at 0° C. After addition, the reaction mixture was stirred at 25° C. for 24 hours. The solvent was removed under reduced pressure and the resulted residue was purified by column chromatography (hexane:EtOAc=1.5:1) to give the title compound as a yellow solid (0.83 g, 47%). NMR (400 MHz) 12.39 (s, 1H), 10.12 (s, 1H), 8.77 (d, J=1.2 Hz, 1H), 6.35 (s, 1H), 1.95 (m, 1H), 0.96 (m, 2H), 0.71 (m, 2H). MS: Calcd.: 313. Found: [M+H]+ 314.

Method 18

Following a similar procedure to Method 17, the following compound was synthesized from a 2,3,6-trichloro-5-nitropyridine by reacting it with the appropriate amine Method 19

6-Bromo-N-(4-fluorobenzyl)pyridin-2-amine

To a suspension of 6-bromopyridin-2-amine (500 mg, 2.89 mmol), sodium tert-butoxide (695 mg, 7.24 mmol) in anhydrous toluene (20 ml) was added 4-fluorobenzylchloride (415 mg, 2.90 mmol) at room temperature. The reaction mixture was heated at 100° C. overnight. EtOAc was added and the mixture was washed with brine and was concentrated. Flash chromatography (10-14% EtOAc in hexanes) gave the title compound (506 mg, 63%). $^1$H NMR (CDCl$_3$) δ 4.40 (m, 2H), 4.95 (br s, 1H), 6.20 (m, 1H), 6.73 (m, 1H), 7.00 (m, 2H), 7.25 (m, 3H).

Method 20

6-Chloro-N-[(1S)-1-(4-fluorophenyl)ethyl]pyridin-2-amine

To a 25 ml round bottom flask was added Pd(OAc)$_2$ (45 mg, 0.2 mmol), (biphenyl-2-ylmethylene)bis(dimethylphosphine) (120 mg, 0.4 mmol) and sodium tert-butoxide (480 mg, 5.0 mmol). The flask was sealed and refilled with N$_2$. To the mixture was added a solution of 2,6-dichloropyridine (300 mg, 2.0 mmol) and [(1S)-1-(4-fluorophenyl)ethyl]amine (306 mg, 2.2 mmol) in toluene (4 ml). The reaction mixture was heated at 85° C. overnight. The solvent was removed and EtOAc was added and the mixture was washed with brine and was concentrated. Flash chromatography (10-40% EtOAc in hexanes) gave the title compound (339 mg, 68%). $^1$H NMR (CDCl$_3$) δ 1.55 (m, 3H), 4.66 (m, 1H), 5.07 (br s, 1H), 6.01 (m, 1H), 6.54 (m, 1H), 7.00 (m, 2H), 7.25 (m, 3H).

Method 21 tert-Butyl 5-cyclopropyl-3-[(6-{[(1S)-1-(4-fluorophenyl)ethyl]amino}pyridin-2-yl)amino]-1H-pyrazole-1-carboxylate To a 25 ml round bottom flask was added Pd$_2$(dba)$_3$ (84 mg, 0.092 mmol), (biphenyl-2-ylmethylene)bis(dimethylphosphine) (55 mg, 0.184 mmol) and sodium tert-butoxide (132 mg, 1.38 mmol). The flask was sealed and refilled with N$_2$. To the mixture was added a solution of 6-chloro-N-[(1S)-1-(4-fluorophenyl)ethyl]pyridin-2-amine (Method 20; 230 mg,

| Meth | Product | NMR/MS | Amine 1 |
|---|---|---|---|
| 18 | (R)-2-(3,6-Dichloro-5-nitropyridin-2-ylamino)-2-(4-fluorophenyl)ethanol | (400 MHz) 8.46 (s, 1H), 8.22 (d, J = 8.0 Hz, 1H), 7.45 (m, 2H), 7.16 (m, 2H), 5.22 (m, 1H), 5.05 (t, J = 6.0 Hz, 1H), 3.87 (m, 1H), 3.72 (m, 1H) | (R)-2-amino-2-(4-fluoro phenyl)ethanol |

0.92 mmol) and tert-butyl 3-amino-5-cyclopropyl-1H-pyrazole-1-carboxylate (223 mg, 1.0 mmol) in toluene (4 ml). The reaction mixture was heated at 110° C. overnight. Solvent was removed and EtOAc was added and the mixture was washed with brine and was concentrated. Flash chromatography (15-40% EtOAc in hexanes) gave the title compound (146 mg, 36%). $^1$H NMR (CDCl$_3$) δ 0.80-1.00 (m, 4H), 1.60 (m, 3H), 1.65 (s, 9H), 1.95 (m, 1H), 4.71 (m, 1H), 4.75 (m, 1H), 5.75 (m, 1H), 6.09 (m, 1H), 6.21 (s, 1H), 7.00 (m, 2H), 7.23 (m, 2H), 7.30 (m, 1H), 9.40 (s, 1H).

Method 22 tert-Butyl (2-{[(6-[(5-cyclopropyl-1H-pyrazol-3-yl) amino]-5-fluoro-2-{[(1S)-1-(4-fluorophenyl)ethyl] amino}pyridin-3-yl)methyl]amino}-2-oxoethyl)carbamate A round bottom flask was charged with (S)-3-(aminomethyl)-$N^6$-(5-cyclopropyl-1H-pyrazol-3-yl)-5-fluoro-$N^2$-(1-(4-fluorophenyl)ethyl)pyridine-2,6-diamine (Example 3; 0.07 g, 0.18 mmol), 2-(tert-butoxycarbonyl)acetic acid loaded TFP resin (1.15 mmol/g loading, 0.18 mmol), and a THF-DCM solution (1:1, 4 ml) at 0° C. The resulting solution was shaken vigorously at 0° C. for 2 hrs and filtered. The resulting resin was washed with a THF-DCM solution (1:1, 3×5 ml for 30 min. each). The resulting organic layers were combined and concentrated. The resulting solid was purified by reverse-phase column chromatography (5-50% $CH_3CN$ in $H_2O$ over 400 ml) to give the title compound (0.035 g, 35%). MS: Calcd.: 541. Found: $[M+H]^+$ 542.

Method 23

(S)-5,6-Difluoro-N-(1-(4-fluorophenyl)ethyl)-3-nitropyridin-2-amine

A solution of 2,3,6-trifluoro-5-nitropyridine (Method 24, 2.0 g, 11.2 mmol) in THF (50 ml) was cooled to 0° C. (S)-1-(4-Fluorophenyl)ethanamine (1.56 g, 11.2 mmol) was added and the reaction was stirred at 0° C. for 30 minutes. The reaction was quenched with water (50 ml) and then extracted with DCM (2×75 ml). The combined organic fractions were dried over $Na_2SO_4$, filtered, and then concentrated. The resulting oil was purified by column chromatography (hexane-DCM=1:1) to give the title compound (2.3 g, 70%).

Method 24

2,3,6-Trifluoro-5-nitropyridine

To neat 2,3,6-trifluoropyridine (12.0 g, 90 mmol) was slowly added fuming $HNO_3$ (142 g, 2254 mmol) and $H_2SO_4$ (133 g, 1353 mmol) slow enough to keep the internal temperature below 40° C. Upon completion of the addition, the resulting solution was heated to 60° C. for 30 minutes, and then cooled to 0° C. Ice water (21) was added, and the reaction was extracted with hexanes (2×300 ml) and then DCM (1×300 ml). The combined organic fractions were dried over $Na_2SO_4$, filtered, and concentrated to give the title compound (8.1 g, 50%), which was used without further purification.

Method 25

(S)-2-(5,6-Difluoro-3-nitropyridin-2-ylamino)-2-(4-fluorophenyl)ethanol

A solution of 2,3,6-trifluoro-5-nitropyridine (1.2 g, 6.7 mmol) in THF (40 ml) was cooled to 0° C. (R)-2-amino-2-(4-fluorophenyl)ethanol (1.0 g, 6.7 mmol) was then added and the reaction was stirred at 0° C. for 30 minutes. The reaction was quenched with water (50 ml) and then extracted with DCM (2×75 ml). The combined organic fractions were dried over $Na_2SO_4$, filtered, and then concentrated. The resulting oil was purified by column chromatography (DCM-MeOH=100:1) to give the title compound (1.2 g, 57%). The product was carried over to the next step without characterization.

Method 26

5,6-Dichloro-N-(5-isopropoxy-1H-pyrazol-3-yl)-3-nitropyridin-2-amine

To a mixture of 2,3,6-trichloro-5-nitropyridine (2.61 g, 11.4 mmol) and DIEA (1.90 ml, 11.4 mmol) in THF (50 ml) was added the 5-isopropoxy-1H-pyrazol-3-amine (1.20 g, 8.50 mmol) at 0° C. After addition, the reaction mixture was stirred at 25° C. for 5 days. The solvent was removed under reduced pressure and the resulting residue was purified by column chromatography (hexane-EtOAc=2.5:1) to give the title compound as a yellow solid (0.77 g, 27%). $^1$H NMR (400 MHz) δ 12.26 & 11.64 (s, 1H), 10.42 & 10.04 (s, 1H), 8.81 & 8.77 (s, 1H), 6.02 & 5.94 (s, 1H), 4.70 & 4.48 (m, 1H), 1.32 (d, J=6.0 Hz, 3H), 1.27 (d, J=6.0 Hz, 1H). MS: Calcd.: 331. Found: $[M+H]^+$ 332.

Method 27

3,6-Dichloro-N-(5-isopropoxy-1H-pyrazol-3-yl)-5-nitropyridin-2-amine

To a mixture of 2,3,6-trichloro-5-nitropyridine (2.61 g, 11.4 mmol) and DIEA (1.90 ml, 11.4 mmol) in THF (50 ml) was added 5-isopropoxy-1H-pyrazol-3-amine (1.20 g, 8.50 mmol) at 0° C. After addition, the reaction mixture was stirred at 25° C. for 5 days. The solvent was removed under reduced pressure and the resulted residue was purified by column chromatography (hexane-EtOAc=1:1) to give the title compound as a yellow solid (0.51 g, 18%). $^1$H NMR (400 MHz) δ 12.22 & 11.35 (s, 1H), 10.12 & 9.80 (s, 1H), 8.64 & 8.54 (s, 1H), 5.95 & 5.84 (s, 1H), 4.70 & 4.46 (m, 1H), 1.27-1.32 (m, 6H). MS: Calcd.: 331. Found: $[M+H]^+$ 332.

Method 28

6-Chloro-N-(5-isopropoxy-1H-pyrazol-3-yl)-3-nitropyridin-2-amine

To a solution of 2,6-dichloro-3-nitropyridine (0.51 g, 2.7 mmol) and DIEA (0.39 ml, 2.2 mmol) in THF (10 ml) was added the 5-isopropoxy-1H-pyrazol-3-amine (0.25 g, 1.8 mmol) solution at 0° C. After addition, the reaction mixture was stirred at 25° C. for 3 days and 60° C. for 24 hours. The solvent was removed under reduced pressure and the resulting residue was purified by column chromatography (hexane-EtOAc=3:1) to give the title compound as a yellow solid (0.33 g, 63%). $^1$H NMR (400 MHz) δ 12.25 & 11.66 (s, 1H), 10.46 & 10.13 (s, 1H), 8.58 & 8.55 (d, J=8.8 Hz, 1H), 7.11 & 7.02 (d, J=8.8 Hz, 1H), 6.08 & 5.97 (s, 1H), 4.70 & 4.48 (m, 1H), 1.32 & 1.27 (d, J=6.0 Hz, 6H). MS: Calcd.: 297. Found: $[M+H]^+$ 298.

Method 29

(R)-2-(6-Chloro-3-nitropyridin-2-ylamino)-2-(4-fluorophenyl)ethanol

To a mixture of 2,6-dichloro-3-nitropyridine (0.933 g, 4.83 mmol) and potassium carbonate (0.58 g, 4.19 mmol) in anhydrous acetonitrile (10 ml) was added (R)-2-amino-2-(4-fluoro phenyl)ethanol (1.00 g, 7.19 mmol) at 0° C. The resulting reaction mixture was stirred at 25° C. for 18 hours. The solid was removed by filtration and washed with EtOAc (20 ml). After evaporation of the solvent, the resulting residue was purified by column chromatography (hexane-EtOAc=5:1) to give the title compound as a yellow solid (0.77 g, 61%). $^1$H NMR (400 MHz) δ 8.96 (d, J=7.6 Hz, 1H), 8.46 (d, J=8.4 Hz, 1H), 7.45 (m, 2H), 7.15 (m, 2H), 6.81 (d, J=8.8 Hz, 1H), 5.27 (m, 2H), 3.80 (m, 2H).
Method 30

(S)-6-Chloro-N-(1-(4-fluorophenyl)ethyl)-3-nitropyridin-2-amine

To a mixture of 2,6-dichloro-3-nitropyridine (2.26 g, 10.8 mmol) and potassium carbonate (1.29 g, 9.34 mmol) in anhydrous $CH_3CN$ (20 ml), was added (S)-1-(4-fluoro-phenyl)-ethylamine (1.00 g, 7.19 mmol) dropwise at 0° C. The reaction mixture was stirred at 25° C. for 17 hours. The solid was removed by filtration and the resulted cake was washed with EtOAc (20 ml). The combined filtrate was concentrated and purified by column chromatography (hexane-EtOAc=10:1) to give the title compound as a yellow solid (1.74 g, 82%). $^1H$ NMR (400 MHz) δ 8.65 (d, J=7.6 Hz, 1H), 8.43 (d, J=8.4 Hz, 1H), 7.51 (m, 2H), 7.16 (m, 2H), 6.81 (d, J=8.8 Hz, 1H), 5.37 (m, 1H), 1.59 (d, J=6.8 Hz, 3H).
Method 31

N-(5-Cyclopropyl-1H-pyrazol-3-yl)-3,6-difluoropyridin-2-amine

A solution of tert-butyl 5-amino-3-cyclopropyl-1H-pyrazole-1-carboxylate (1.00 g, 4.49 mmol) in THF (15 ml) was cooled to −78° C. t-BuLi (1.7 M in THF, 4.15 mmol) was added dropwise and the resulting solution was stirred for 30 min. at −78° C. A solution of 2,3,6-trifluoropyridine (0.46 g, 3.4 mmol) in THF (5 ml) was added, and the resulting solution was stirred for 5 min at −78° C., and then the reaction was warmed to 0° C., and stirred at that temperature for 30 min. The reaction was quenched with aq. $NH_4Cl$ and extract with EtOAc (2×20 ml). The organic fractions were dried over $Na_2SO_4$, filtered, and concentrated. The resulting oil was then placed in ACN (15 ml) at 0° C., and N-trimethylsilylimidazole (0.5 ml) was added. The reaction was stirred for 20 min, and then concentrated. The resulting oil was purified by column chromatography (DCM-MeOH=100:1) to give the title compound (0.10 g, 12%). MS: Calcd.: 236. Found: $[M+H]^+$ 237.
Method 32

6-(5-Cyclopropyl-1H-pyrazol-3-ylamino)-2,5-difluoronicotinonitrile

A solution of 2,5,6-trifluoronicotinonitrile (30.0 g, 189.8 mmol) in ACN (240 ml) was prepared in a 1l 3-neck flask at room temperature and then cooled to −5° C. using an ice-salt bath. An addition funnel containing triethylamine (29.1 ml, 208.8 mmol) and a second addition funnel containing a solution of 5-cyclopropyl-1H-pyrazol-3-amine (25.7 g, 208.8 mmol) in ACN (160 ml) were placed on top of the reaction flask. A total of 5 ml of triethylamine was added quickly dropwise to the reaction. The reaction was allowed to stir for min, followed by the simultaneous dropwise addition of the remaining triethylamine and 5-cyclopropyl-1H-pyrazol-3-amine solution at a rate slow enough to keep the internal temperature at or below 5° C. Upon completion of the addition, the reaction was allowed to stir for 1 hour at 0° C., at which point no starting material remained, and the reaction was filtered through a fritted funnel. The remaining solids were washed with 0° C. ACN (3×100 ml). The solid product was then dried under vacuum for 30 minutes to give the title compound (25.2 g, 51%) which was used without further purification. $^1H$ NMR (400 MHz, $CD_3OD$) δ 7.81-7.77 (m, 1H), 6.33 (s, 1H), 1.91 (septet, 1H), 0.99-0.98 (m, 2H), 0.76-0.73 (m, 2H). MS: Calcd.: 261. Found: $[M+H]^+$ 262.
Method 33

(S)-1-(5-Fluoropyridin-2-yl)ethanamine

To the solution of (S)-tert-butyl-1-(5-fluoropyridin-2-yl) ethylcarbamate (Method 34, 12.8 g, 53.3 mmol) in DCM (100 ml) was added HCl/dioxane solution (107 ml, 4 N, 428 mmol). The reaction was stirred at room temperature for 3 hours. The solvent was removed and 50 ml of saturated sodium bicarbonate was added. The resulting aqueous solution was extracted with ether (6×400 ml), dried over sodium sulfate and concentrated to give the title compound (7.30 g, 98%) as pale yellow oil. $^1H$ NMR (400 MHz) δ 8.44 (d, J=2.8 Hz, 1H), 7.66 (m, 1H), 7.53 (m, 1H), 4.01 (q, J=6.8 Hz, 1H), 1.94 (b, 2H), 1.26 (d, J=6.8 Hz, 3H). MS: Calcd.: 140. Found: $[M+H]^+$ 141.
Method 34

(S)-tert-Butyl-1-(5-fluoropyridin-2-yl)ethylcarbamate

The solution of (S)—N-(1-(5-fluoropyridin-2-yl)ethyl)acetamide (Method 35, 11.0 g, 60.37 mmol), DMAP (1.48 g, 12.07 mmol) and $Boc_2O$ (26.35 g, 120.7 mmol) in THF (100 ml) was stirred at 50° C. for 20 hours. After cooled to room temperature, lithium hydroxide monohydrate (5.19 g, 123.8 mmol) and water (100 ml) were added. The reaction was stirred at room temperature for 5 hours and diluted with ether (200 ml). The organic layer was separated, washed with brine (100 ml), and dried over sodium sulfate. After removal of solvent, the resulted residue was purified by column chromatography (Hexane-EtOAc=5:1) to give the title compound as a pale yellow oil (13.6 g, 94%). $^1H$ NMR (400 MHz) δ 8.46 (d, J=2.8 Hz, 1H), 7.69 (m, 1H), 7.35-7.41 (m, 2H), 4.67 (m, 1H), 1.37 (s, 9H), 1.32 (d, J=7.2 Hz, 3H). MS: Calcd.: 240. Found: $[M+H]^+$ 241.
Method 35

(S)—N-(1-(5-Fluoropyridin-2-yl)ethyl)acetamide

N-(1-(5-fluoropyridin-2-yl)vinyl)acetamide (Method 36, 11.0 g, 61.1 mmol) in MeOH (120 ml) under $N_2$ was added (+)-1,2-bis((2S,5S)-2,5-diethylphospholano)benzene (cyclooctadiene)rhodium(I)trifluoromethanesulfonate (0.441 g, 0.611 mmol). The solution was transferred to a high pressure bomb and charged 150 psi $H_2$. The reaction stirred at room temperature and maintained inside pressure between 120-150 psi for 7 hours. The solvent was removed and the resulted residue was purified by column chromatography (EtOAc) to give the title compound as a white solid (9.8 g, 88%). $^1H$ NMR (400 MHz) δ 8.49 (d, J=2.4 Hz, 1H), 8.32 (d, J=7.6 Hz, 1H), 7.66 (m, 1H), 7.39 (dd, J=4.4 and 8.8 Hz, 1H), 4.95 (m, 1H), 1.85 (s, 3H), 1.34 (d, J=7.2 Hz, 3H). MS: Calcd.: 182. Found: $[M+H]^+$ 183. Enantiomeric excess determined by HPLC (Chiralpak IA; 70:30 $CO_2$/MeOH), 95.3% ee.
Method 36

N-(1-(5-Fluoropyridin-2-yl)vinyl)acetamide

A solution of MeMgBr (170.3 ml, 510.98 mmol) in ether was diluted with 170 ml of anhydrous THF and cooled to 0° C. 5-Fluoropicolinonitrile (Method 37, 53.6 g, 425.82 mmol) in THF (170 ml) was added dropwise. The reaction was stirred at 0° C. for 30 minutes, then diluted with DCM (170 ml). Acetic anhydride (48.3 ml, 510.98 mmol) in DCM (100 ml) was added dropwise at 0° C. After addition, the reaction was warmed to room temperature and stirred at room temperature for 8 hours. Saturated sodium bicarbonate solution (50 ml) was added and extracted with EtOAc (2×200 ml). The combined organic was dried over sodium sulfate. After removal of solvent, the resulted residue was purified by column chromatography (hexane-EtOAc=2.5:1) to give the title compound as a white solid (26.6 g, 35%). $^1$H NMR (400 MHz) δ 9.37 (s, 1H), 8.57 (d, J=2.8 Hz, 1H), 7.81 (m, 2H), 6.01 (s, 1H), 5.52 (s, 1H), 2.08 (s, 3H). MS: Calcd.: 180. Found: [M+H]$^+$ 181.

Method 37

5-Fluoropicolinontrile

2-Bromo-5-fluoropyridine (93.0 g, 528 mmol), Zn dust (8.29 g, 127 mmol), zinc cyanide (40.3 g, 343 mmol), diphenylphosphinoferrocene (11.7 g, 21.1 mmol) and Pd$_2$ dba$_3$ (9.68 g, 10.6 mmol) in anhydrous DMA (300 ml) was heated at 95° C. for 3 hours. After cooled to room temperature, brine (100 ml) and ether (500 ml) was added. The solid formed was removed by filtration and washed with ether (300 ml). The organic layer was separated, washed with brine (200 ml) and dried over sodium sulfate, and concentrated. After removal of solvent, the resulted residue was purified by column chromatography (hexane-DCM=1:1) to give the title compound as a white solid (49 g, 72%). $^1$H NMR (400 MHz) δ 8.82 (d, J=2.8 Hz, 1H), 8.21 (dd, J=4.4 and 8.8 Hz, 1H), 8.05 (dd, J=2.8 and 8.8 Hz, 1H).

Method 38

6-Fluoro-N-methoxy-N-methylnicotinamide

To a solution of 6-fluoronicotinic acid (10 g, 70.9 mmol) in DCM (200 ml), was added N,O-Dimethylhydroxylamine hydrochloride (7.3 g, 74.8 mmol), N-(3-Dimethylaminopropyl)-N'-ethylcarbodiimide hydrochloride (15 g, 78.5 mmol), and triethylamine (22 ml, 156 mmol). The reaction mixture was allowed to stir at room temperature for 16 hours. The reaction was partitioned with water, layers were cut, and organic layer was dried over Na$_2$SO$_4$, filtered, and concentrated in vacuo. The crude residue obtained was purified by a silica gel filtration using EtOAc-DCM (4:1) to give 7.2 g (55% isolated yield) of the title compound. $^1$H NMR: 8.48 (s, 1H) 8.21 (t, J=8.29 Hz, 1H) 7.27 (dd, J=8.29, 3.01 Hz, 1H) 3.54 (s, 3H) 3.27 (s, 3H).

Method 39

2-Chloro-6-(5-cyclopropyl-1H-pyrazol-3-ylamino)-5-fluoro-4-iodonicotinonitrile

The crude 2,6-dichloro-5-fluoro-4-iodonicotinonitrile (8.0 g, 25.2 mmol), Et$_3$N (3.3 g, 32.8 mmol) and 5-cyclopropyl-1H-pyrazol-3-amine (3.1 g, 25.2 mmol) were placed in ACN (50 ml) and the resulting solution was heated to 80° C. for 24 hours. The reaction was cooled to room temperature, filtered, and the resulting solid was washed with cold ACN, dried, and collected to give the title compound (3.0 g, 29%). MS: Calcd.: 403. Found: [M+H]$^+$ 404.

Method 40

2,6-Dichloro-5-fluoro-4-iodonicotinonitrile

To a solution of diisopropylamine (15.9 g, 157 mmol) in THF (400 ml) at −78° C. was added n-butyllithium (2.5 M hexanes, 154 mmol), and the solution was stirred at −78° C. for 30 minutes. The lithium diisopropylamide solution was then added slowly dropwise to a −78° C. solution of 2,6-dichloro-5-fluoronicotinonitrile (10.0 g, 52.3 mmol) and iodine (26.5 g, 104 mmol) in THF (175 ml). Upon completion of the addition, the reaction was allowed to warm slowly to room temperature, and stirred at room temperature for 12 hours. An aqueous 10% Na$_2$S$_2$O$_3$ solution (500 ml) was added and the reaction was extracted with EtOAc (3×300 ml). The combined organic fractions were dried over Na$_2$SO$_4$, filtered, and then concentrated to give the title compound (14.5 g, 87%) as a brown solid that was used without further purification.

Method 41

2,5-Difluoro-6-(5-methyl-1H-pyrazol-3-ylamino) nicotinonitrile

To a solution of 2,5,6-trifluoronicotinonitrile (1.0 g, 6.3 mmol) and triethylamine (0.83 g, 8.2 mmol) in ACN (30 ml) at 0° C. was added 5-methyl-1H-pyrazol-3-amine (0.67 g, 6.9 mmol). The reaction was stirred at 0° C. for 1 hour, at which point the reaction was filtered. The resulting solid was washed with cold ACN, dried and collected to give the title compound (0.44 g, 29%). MS: Calcd.: 235. Found: [M+H]$^+$ 236.

Method 42

2,5-Difluoro-6-(5-isopropoxy-1H-pyrazol-3-ylamino)nicotinonitrile

To a solution of 2,5,6-trifluoronicotinonitrile (3.0 g, 19.0 mmol) and triethylamine (2.5 g, 24.7 mmol) in ACN (30 ml) at 0° C. was added 5-isopropoxy-1H-pyrazol-3-amine (2.95 g, 20.9 mmol) in ACN (15 ml). The reaction was stirred at 0° C. for 1 hour, at which point the reaction was diluted with water (50 ml) and extracted with DCM (2×50 ml). The combined organic fractions were dried over Na$_2$SO$_4$, filtered, and then concentrated. The resulting oil was purified by column chromatography (DCM-MeOH=100:1) to give the title compound (0.48 g, 9%). MS: Calcd.: 279. Found: [M+H]$^+$ 280.

Method 42 (Alternative Procedure)

2,5-Difluoro-6-(5-isopropoxy-1H-pyrazol-3-ylamino)nicotinonitrile tert-Butyl 5-(5-cyano-3,6-difluoropyridin-2-ylamino)-3-isopropoxy-1H-pyrazole-1-carboxylate (Method 79, 10.6 g, 27.9 mmol), was placed in DCM (500 ml) at room temperature. A 4.0 M solution of HCl (16.3 g, 447 mmol) in dioxane was added dropwise, and upon completion of the addition the reaction was allowed to stir for an additional 30 minutes. The reaction was concentrated to dryness, and dissolved in DCM (300 ml) with a minimal amount of MeOH (5 ml) to aid solubility. A saturated aqueous solution of Na$_2$CO$_3$ (300 ml) was added, and the reaction was stirred vigorously for 30 minutes. The layers were allowed to separate, and the organic fraction was dried (Na$_2$SO$_4$), filtered, and concentrated. The resulting residue was slurried with cold DCM (approx. 50 ml), filtered, and the remaining solid was washed with DCM and dried to give the title compound (5.5 g, 70%). MS: Calcd.: 279. Found: [M+H]$^+$ 280.

Method 43

2,5-Dichloro-6-(5-cyclopropyl-1H-pyrazol-3-ylamino)nicotinonitrile

To a solution of 2,5,6-trichloronicotinonitrile (Method 44, 1.0 g, 4.8 mmol) and DIEA (0.81 g, 6.2 mmol) in n-BuOH (5 ml) was added 5-cyclopropyl-1H-pyrazol-3-amine (2.3 g, 19.3 mmol). The reaction was heated to 60° C. for 2 hours, at which point the reaction was cooled to room temperature and concentrated. The resulting residue was diluted with 10 ml ACN, and stored at 0° C. for 1 hour. The solids that formed were then filtered, washed with cold ACN, dried and collected to give the title compound (0.62 g, 43%). MS: Calcd.: 294. Found: [M+H]$^+$ 295.

Method 44

2,5,6-Trichloronicotinonitrile

A suspension of 2,5,6-trichloronicotinamide (Method 45, 2.3 g, 10.2 mmol) in POCl$_3$ (20 ml) was heated to 90° C. for 1 hour. The reaction was then cooled to room temperature, and the POCl$_3$ was removed under vacuum. The resulting residue was taken up in DCM (50 ml) and ice water (50 ml) was then added, followed by the careful addition of an aqueous solution of Na$_2$CO$_3$ until pH 8 was achieved. The organic fraction was then dried over Na$_2$SO$_4$, filtered, and concentrated to give the title compound (2.1 g, 80%) which was used without further purification. $^1$H NMR (400 MHz, CD$_3$OD) δ 8.54 (s, 1H).

Method 44 (Alternative Procedure)

2,5,6-Trichloronicotinonitrile

To a solution of 2,4,5,6-tetrachloronicotinonitrile (7.6 g, 31.4 mmol) in MeOH/THF (230 ml/230 ml) was added zinc dust (4.0 g, 62.8 mmol) slowly at 0° C. and the saturated NH$_4$Cl solution (105 ml) and the mixture was stirred for 30 minutes. TLC indicated that the reaction is complete. Saturated NH$_4$OAc solution (180 ml) was added to the mixture and the mixture was allowed to stir at room temperature for 30 minutes. The mixture was filtered and was washed with EtOAc (500 ml). The filtrate was washed with brine and dried and concentrated to give a solid. ISCO column purification gave the title compound (4.63 g, 71%). $^1$H NMR (CDCl$_3$): δ 8.97 (s, 1H).

Method 45

2,5,6-Trichloronicotinamide

A solution of 2,5,6-trichloronicotinoyl chloride (Method 46, 2.5 g, 10.2 mmol) in dioxane (20 ml) was added dropwise to 10 ml ammonium hydroxide (28% NH$_3$ in water) at 0° C. Upon completion of the addition, the reaction was allowed to stir for an additional 10 minutes, and then extracted with DCM (3×50 ml). The combined organic fractions were dried over Na$_2$SO$_4$, filtered, and concentrated to give the title compound (2.3 g, 100%), which was used without further purification.

Method 46

2,5,6-Trichloronicotinoyl chloride

To a suspension of 2,5,6-trichloronicotinic acid (Method 47, 2.3 g, 10.2 mmol) in DCM (25 ml) at room temperature was added oxalyl chloride (3.0 g, 24.4 mmol) and 3 drops of dry DMF. After 30 minutes, the resulting clear solution was concentrated to dryness to give the title compound (2.5 g, 100%), which was immediately used without further purification.

Method 47

2,5,6-Trichloronicotinic acid

A suspension of 2,3,6-trichloro-5-methylpyridine (Method 48, 11.8 g, 60.0 mmol) in water (400 ml) was heated to 100° C. Portionwise, KMnO$_4$ (28.5 g, 180.2 mmol) was then added over 12 hours. The reaction was then allowed to stir for 2 days at 100° C., over which time an additional 10 g of KMnO$_4$ was added portionwise. When no starting material remained, the hot reaction was filtered, washed with hot water (2×75 ml), and the resulting filtrate was allowed to cool to room temperature. The aqueous filtrate was then extracted with EtOAc (3×100 ml), and then concentrated to a 50 ml volume. This aqueous solution was then cooled to 0° C. and adjusted to pH 1-2 with 6.0 M HCl. The resulting solid was then collected by filtration, washed with cold water, and dried to give the title compound (2.5 g, 18%) that was used without further purification.

Method 48

2,3,6-Trichloro-5-methylpyridine

A well powdered mixture of 3-methylpiperidine-2,6-dione (Method 49, 15.0 g, 118 mmol) and PCl$_5$ (155.0 g, 743 mmol) was slowly heated to 150° C. and kept at that temperature for 2 hours. The resulting solution was then cooled to room temperature, and slowly poured onto ice. The resulting precipitate was filtered, washed with cold water, and dried. The resulting precipitate was then recrystallized from a mixture of EtOH-petroleum ether (1:8) to give the title compound (11.8 g, 51%).

Method 49

3-Methylpiperidine-2,6-dione

A solution of H$_2$SO$_4$ (80 ml), acetic acid (500 ml) and 2-methylpentanedinitrile (128.0 g, 1184 mmol) was stirred at room temperature. An aqueous solution of acetic acid (100 ml in 32 ml water) was then added dropwise. Upon completion of the addition, the reaction was heated to 130° C. for 1 hour. The reaction was then allowed to cool to room temperature and filtered to remove solids, which were washed with acetic acid (100 ml). The filtrate was then concentrated until a residue resulted. This residue was poured into water (0.75 l), and adjusted to pH 5 with Na$_2$CO$_3$. The resulting solid was collected by filtration and washed with cold water to give the title compound (101 g, 67%) which was used without further purification.

Method 50

(S)-1-(3,5-Difluoropyridin-2-yl)ethanamine

To a solution of (S)-tert-butyl-1-(3,5-difluoropyridin-2-yl) ethylcarbamate (Method 51, 2.05 g, 7.94 mmol) in DCM (15 ml) was added HCl/dioxane (15.9 ml, 4 N, 63.5 mmol). The reaction was stirred at room temperature for 3 hours. The solvent was removed and 10 ml of saturated sodium bicarbonate was added. The resulting aqueous solution was extracted with ether (5×100 ml), dried over sodium sulfate and concentrated to give the title compound (1.1 g, 88%) as a pale yellow oil. $^1$H NMR (400 MHz) δ 8.46 (d, J=2.0 Hz, 1H), 7.85 (m, 1H), 4.23 (q, J=6.8 Hz, 1H), 1.90 (b, 2H), 1.27 (d, J=6.8 Hz, 3H). MS: Calcd.: 158. Found: [M+H]$^+$ 159.

Method 51

(S)-tert-Butyl-1-(3,5-difluoropyridin-2-yl)ethylcarbamate

A solution of (S)—N-(1-(3,5-difluoropyridin-2-yl)ethyl) acetamide (Method 52, 2.0 g, 9.99 mmol), DMAP (0.244 g, 2.00 mmol), and Boc$_2$O (6.54 g, 30.0 mmol) in THF (20 ml) was stirred at 50° C. for 40 hours. After cooling to room temperature, lithium hydroxide monohydrate (0.671 g, 16.0 mmol) and water (20 ml) were added. The reaction was stirred at room temperature for 18 hours. To which was added ether (100 ml). The organic layer was separated, washed with brine (50 ml) and dried over sodium sulfate. After removal of solvent, the resulted residue was purified by column chromatography (hexane-EtOAc=5:1) to give the title compound as a colourless oil (2.05 g, 79%). $^1$H NMR (400 MHz) δ 8.45 (s, 1H), 7.87 (m, 1H), 7.24 (d, J=7.6 Hz 1H), 4.92 (m, 1H), 1.34 (s, 9H), 1.32 (d, J=7.2 Hz, 3H). MS: Calcd.: 258. Found: [M+H]$^+$ 259. Enantiomeric excess was determined by HPLC (Chiralpak ADH; 98:2 $CO_2$/MeOH), 93.6% ee.

Method 52

(S)—N-(1-(3,5-Difluoropyridin-2-yl)ethyl)acetamide

To a solution of N-(1-(3,5-difluoropyridin-2-yl)vinyl)acetamide (Method 53, 2.2 g, 11.1 mmol) in MeOH (20 ml) under $N_2$ was added (+)-1,2-bis((2S,5S)-2,5-dimethyl phospholano)benzene (cyclooctadiene)rhodium(I)trifluoromethanesulfonate (0.074 g, 0.111 mmol). The solution was transferred to a high-pressure bomb and charged 150 psi $H_2$. The reaction stirred at room temperature and maintained inside pressure between 120-150 psi for 24 hours. The solvent was removed and the resulted residue was purified by column chromatography (EtOAc) to give the title compound as a white solid (2.0 g, 90%). $^1$H NMR (400 MHz) δ 8.47 (d, J=2.4 Hz, 1H), 8.34 (d, J=7.2 Hz, 1H), 7.89 (m, 1H), 5.21 (m, 1H), 1.81 (s, 3H), 1.34 (d, J=6.8 Hz, 3H). MS: Calcd.: 200. Found: [M+H]$^+$ 201.

Method 53

N-(1-(3,5-Difluoropyridin-2-yl)vinyl)acetamide

To a mixture of (Z)-1-(3,5-difluoropyridin-2-yl)ethanone oxime (Method 54, 12.5 g, 72.6 mmol), acetic anhydride (54.8 ml, 581 mmol), and iron powder (32.4 g, 581 mmol) in DMF (100 ml) was added TMSCl (0.01 ml, 0.073 mmol). The reaction mixture was stirred at room temperature for 18 hours, then diluted with ether (300 ml) and filtered through a short pad of celite. The filtrate was concentrated and the residue was partitioned between 200 ml of EtOAc and 50 ml of saturated sodium bicarbonate. The organic layer was separated and dried over sodium sulfate. After removal of solvent, the resulted residue was purified by column chromatography (hexane-EtOAc=2:1) to give the title compound as a white solid (2.70 g, 19%). $^1$H NMR (400 MHz) δ 9.55 (s, 1H), 8.51 (d, J=2.0 Hz, 1H), 7.97 (m, 1H), 5.87 (s, 1H), 5.14 (s, 1H), 1.99 (s, 3H). MS: Calcd.: 198. Found: [M+H]$^+$ 199.

Method 54

(Z)-1-(3,5-Difluoropyridin-2-yl)ethanone oxime

To a solution of 3,5-difluoropicolinonitrile (10.0 g, 71.4 mmol) in THF (200 ml) was added methylmagnesium bromide (61.2 ml, 85.7 mmol) in THF solution at 0° C. The reaction was stirred at room temperature for 1.5 hours. Saturated sodium bicarbonate solution (50 ml) was added, extracted with ether (100 ml), and dried over sodium sulfate. The solvent was removed. The residue (11.2 g, 71.28 mmol), hydroxylamine hydrochloride (9.907 g, 142.6 mmol) and sodium acetate (11.70 g, 142.6 mmol) in EtOH (100 ml) and water (50 ml) was heated at reflux for 3 hours. The solvent was removed and diluted with 50 ml of saturated sodium bicarbonate and extracted with EtOAc (2×200 ml). After dried over sodium sulfate, the solvent was removed and the title compound was used directly in next step without purification.

Method 55

(S)-1-(5-Fluoropyrimidin-2-yl)ethanamine

To a solution of (S)-tert-butyl-1-(5-fluoropyrimidin-2-yl) ethylcarbamate (Method 56, 0.21 g, 0.87 mmol) in DCM (5 ml) was added HCl (1.3 ml, 5.2 mmol) in dioxane. The reaction was stirred at room temperature for 3 hours. The solvent was removed give (S)-1-(5-fluoropyrimidin-2-yl) ethanamine as HCl salt as white solid (quantitative). MS: Calcd.: 141. Found: [M+H]$^+$ 142.

Method 56

(S)-tert-Butyl-1-(5-fluoropyrimidin-2-yl)ethylcarbamate (S)—N-(1-(5-fluoropyrimidin-2-yl)ethyl)acetamide (Method 57, 0.20 g, 1.09 mmol), DMAP (0.027 g, 0.22 mmol) and $Boc_2O$ (0.60 g, 2.73 mmol) in THF (10 ml) was stirred at 50° C. for 40 hours. After cooled to room temperature, lithium hydroxide monohydrate (0.094 g, 2.24 mmol) and water (10 ml) was added. The reaction was stirred at room temperature for 9 hours. Ether (30 ml) was added, organic layer was separated, washed with brine (20 ml) and dried over sodium sulfate. After removal of solvent, the resulted residue was purified by column chromatography (Hex-EtOAc=5:1) to give the title compound as a pale yellow oil (0.21 g, 80%). $^1$H NMR (400 MHz) 8.84 (s, 2H), 7.24 (d, J=7.6 Hz, 1H), 4.74 (m, 1H), 1.35 (s, 12H). MS: Calcd.: 241. Found: [M+H]$^+$ 242.

Method 57

(S)—N-(1-(5-Fluoropyrimidin-2-yl)ethyl)acetamide

N-(1-(5-Fluoropyrimidin-2-yl)vinyl)acetamide (Method 58, 0.10 g, 0.55 mmol) in MeOH (5 ml) under $N_2$ was added (+)-1,2-bis((2S, 5S)-2,5-diethylphospholano)benzene (cyclooctadiene)rhodium(I)trifluoromethanesulfonate (0.04 g, 0.0055 mmol). The solution was transferred to a high pressure bomb and charged 150 psi $H_2$. The reaction stirred at room temperature for 4 hours. The solvent was removed and the resulted residue was purified by column chromatography (EtOAc) to give the title compound as a white solid (0.096 g, 95%). $^1$H NMR (400 MHz) 8.84 (d, J=0.8 Hz, 2H), 8.34 (d, J=7.6 Hz, 1H), 5.00 (m, 1H), 1.84 (s, 3H), 1.37 (d, J=6.8 Hz, 3H). MS: Calcd.: 183. Found: [M+H]$^+$ 184. Enantiomeric excess determined by HPLC (Chiralpak IA; 95:5 $CO_2$/MeOH), >99% ee.

Method 58

N-(1-(5-Fluoropyrimidin-2-yl)vinyl)acetamide

5-Fluoropyrimidine-2-carbonitrile (Method 59, 1.0 g, 8.1 mmol) in THF (10 ml) was added a solution of MeMgBr (3.3 ml, 9.75 mmol) in ether drop wise at 0° C. After addition, the reaction was warmed to room temperature, stirred at room temperature for 1 hour and then diluted with DCM (10 ml). Acetic anhydride (1.23 ml, 13.0 mmol) was added in one portion. The reaction was stirred at room temperature for 1 hour and 40° C. for 1 hour. Saturated sodium bicarbonate solution (10 ml) was added and extracted with EtOAc (2×20 ml). The combined organic was dried over sodium sulfate. After removal of solvent, the resulted residue was purified by column chromatography (hexane-EtOAc=2.5:1) to give the title compound as a white solid (0.38 g, 26%). $^1$H NMR (400

MHz) 9.34 (s, 1H), 8.95 (s, 2H), 6.25 (s, 1H), 6.03 (s, 1H), 2.11 (s, 3H). MS: Calcd.: 181. Found: [M+H]$^+$ 182.
Method 59

5-Fluoropyrimidine-2-carbonitrile

A 10 ml microwave vial was charged with 2-chloro-5-fluoropyrimidine (2.0 g, 15.09 mmol), Pd$_2$(dba)$_3$ (0.549 g, 0.6 mmol), DPPF (0.67 g, 1.21 mmol), zinc cyanide (1.15 g, 9.81 mmol), and zinc dust (0.237 mg, 3.62 mmol). The flask was evacuated and backfilled with N$_2$, and anhydrous dimethylacetamide. The vial was mounted onto a Personal Chemistry microwave reactor and heated at 100° C. for 10 hours. The reaction mixture was diluted with EtOAc and then washed with brine three times. The organic layer was obtained and evaporated to dryness. The dried residue was purified by silica gel chromatography (By ISCO Combiflash with gradient EtOAc and hexanes) to afford the title compound as a creamy solid (1.50 g, 80%). GC-MS: 123 (M); $^1$H NMR (CDCl$_3$) δ 8.80 (s, 2H).
Method 60

2,5-Dichloro-6-[(5-methyl-1H-pyrazol-3-yl)amino]nicotinonitrile

To a 25-ml, round-bottom flask, was added 2,5,6-trichloronicotinonitrile (Method 44, 1 g, 4.8 mmol), 5-methyl-1H-pyrazol-3-amine (466 mg, 4.8 mmol), DIEA (1.1 ml, 6.3 mmol), and EtOH (5 ml) and set to heat at 55° C. for 16 hours. The resulting mixture was then purified by silica gel chromatography (Biotage Horizon System) using 25-75% EtOAc/hexanes to give 770 mg of the title compound. $^1$H NMR: 12.36 (s, 1H) 9.68 (s, 1H) 8.39 (s, 1H) 6.32 (s, 1H) 2.29 (s, 3H). MS: Calcd.: 268. Found: [M+H]$^+$ 267/269.
Method 61

N-[5-(1-Aminoethyl)-2-fluorophenyl]methanesulfonamide

N-{2-Fluoro-5-[(1Z)-N-hydroxyethanimidoyl]phenyl}methanesulfonamide (Method 62, 200 mg, 812 μmol) was dissolved in 15 ml THF, to which was added Raney nickel 2800 slurry in water (200 μl). The mixture was charged with nitrogen and stirred over 1 atm of hydrogen. After 1 hour, MeOH (4 ml) was added and the reaction mixture was stirred overnight. The following morning the solution was filtered through celite, and the cake washed with MeOH, and the organic layer was concentrated to a yellow solid which was dried under high vacuum (181 mg, 96%). $^1$H NMR: 1.26 (d, 3H, CH$_3$), 2.92 (s, 3H, SO$_2$Me), 3.33 (HOD), 4.04 (q, 1H, CH), 5.70 (br, 2H, NH$_2$), 7.06-7.16 (m, 2H, Ar), 7.35 (m, 1H, Ar). LC/MS: 0.79 min, 231.08 (M−H)$^-$.
Method 62

N-{2-Fluoro-5-[(1Z)-N-hydroxyethanimidoyl]phenyl}methanesulfonamide

In a 100 ml Round bottom flask was added. N-(5-acetyl-2-fluorophenyl)methanesulfonamide (Method 63, 1.41 g, 6.10 mmol), hydroxylamine hydrochloride (847 mg, 12.2 mmol), sodium acetate (1.25 g, 15.24 mmol) and 30 ml water. The mixture was heated to 50° C. and then 10 ml EtOH was added to dissolve the contents. The mixture was continued heating at 50° C. for 1 hour, then fitted with a reflux condenser and refluxed at 80° C. for 2 hours. (note: the solution turns homogeneous at 80° C.). The solution was cooled to room temperature (note: crystals develop), rotovapped to remove traces of EtOH, cooled on an ice bath and filtered off-white crystals. The crystalline product was washed with ice cold water and air dried to obtain the white crystalline product (1.47 g, 98%.) TLC (1:1 Hexanes:EtOAc): R$_f$ 0.50. $^1$H NMR: 2.12 (s, 3H, Me), 3.02 (s, 3H, SO$_2$Me), 3.32 (HOD), 7.29 (m, 1H, Ar), 7.48 (m, 1H, Ar), 7.68 (m, 1H, Ar), 9.67 (s, 1H, NH), 11.31 (s, 1H, OH). LC/MS: 1.70 min, 247.04 (M+1)$^+$.
Method 63

N-(5-Acetyl-2-fluorophenyl)methanesulfonamide

3-Amino-4-fluoroacetophenone (Method 64, 1.00 g, 6.53 mmol) and pyridine (503 μl, 6.53 mmol) were stirred in 10 ml DCM over a blanket of nitrogen at 0° C. Methanesulfonylchloride (505 μl, 6.53 mmol) was added dropwise and the reaction was stirred at 0° C. for 5 minutes and warmed to room temperature and stirred for 3 hours. Quenched with 30 ml 1N HCl, and extracted with 30 ml DCM. Washed organic layer with Brine, dried over Na$_2$SO$_4$ and concentrated to orange oil, and dried under high vacuum. Yellow solid/crystals develop which were triturated with hexanes, redissolved in DCM and evaporated and dried under high vacuum to obtain an off-white/yellow solid (1.42 g, 94%.) TLC (1:1 Hexanes:EtOAc): R$_f$ 0.46. $^1$H NMR (CDCl$_3$): δ 2.60 (s, 3H, COMe), 3.08 (s, 3H, SO$_2$Me), 6.56 (br, 1H, NH), 7.23 (dd, 1H, Ar), 7.81 (m, 1H, Ar), 8.16 (m, 1H, Ar). LC/MS: 1.66 min, 230.08 (M−1)$^-$
Method 64

3-Amino-4-fluoroacetophenone

In a 250 ml round bottom flask was added 3-nitro-4-Fluoroacetophenone (5.00 g, 27.3 mmol) and HCl (12M, 13 ml.) The solution was cooled to 0° C. on an ice bath, and SnCl$_2$ (15.5 g, 81.9 mmol) dissolved in 20 ml of water, was added dropwise over a 15 minute period. (Note: The reference material indicates the reaction is exothermic after 1 equivalent addition of Tin Chloride.) After complete addition the reaction mixture was stirred at 0° C. for 10 min, warmed to room temp, brought to reflux for 15 minutes, cooled back to room temp and stirred for 2 hours. The mixture was poured over ice (150 g) and adjusted to pH 12 with 50% NaOH at 0° C. The resulting yellow emulsion was extracted with ether (2×150 ml), washed with brine (1×30 ml), dried over sodium sulfate and concentrated to a yellow solid. The solid was triturated with hexanes and dried to obtain a yellow solid (3.61 g, 86%). TLC (1:1 Hexanes:EtOAc): R$_f$ 0.63. $^1$H NMR (CDCl$_3$): δ 7.44 (m, 1H, Ar), 7.34 (m, 1H, Ar), 7.04 (m, 1H, Ar), 4.32 (br, 2H, NH), 2.54 (s, 3H, Me). LC/MS 1.67 min, 154.07 (M+1)$^+$
Method 65

1-(6-Fluoropyridin-3-yl)ethanone

To a cold solution (−78° C.) of 6-fluoro-N-methoxy-N-methylnicotinamide (Method 38, 7.2 g, 39 mmol) in THF (130 ml), was added methyl magnesium bromide (20 ml, 59 mmol, 3M solution in ether) dropwise. The cooling bath was removed and reaction mixture was allowed to warm to room temperature and stir for 2 hours. The reaction was quenched with 3N HCl solution, layers were cut, and organic layer was dried over Na$_2$SO$_4$, filtered, and concentrated in vacuo to afford 3.8 g (70% yield) of the title compound. $^1$H NMR (CDCl$_3$) δ 8.80 (s, 1H) 8.29-8.43 (m, 1H) 6.98-7.06 (m, 1H) 2.62 (s, 3H).
Method 66

N-[5-(1-Aminoethyl)-2-fluorophenyl]acetamide

To a round, bottom flask was added N-{2-fluoro-5-[(1Z)-N-hydroxyethanimidoyl]phenyl}acetamide (Method 67, 715 mg, 3.4 mmol) and AcOH (0.5 ml) in EtOH (20 ml), followed by the addition of Palladium on carbon (146 mg, 10 wt %) under $N_2$ atmosphere. Once the catalyst was added, the system was evacuated and purged with hydrogen (atmospheric pressure). This process was performed several times to ensure complete saturation of hydrogen to the system. The reaction was then allowed to stir for 16 hours at room temperature. The heterogeneous mixture was then filtered over a pad of Celite and the filtrate was concentrated in vacuo to give quantitative yield of the title compound. $^1$H NMR: 9.67 (s, 1H) 7.80 (d, J=7.54 Hz, 1H) 7.07-7.19 (m, 2H) 4.00 (q, J=6.28 Hz, 1H) 2.06 (s, 3H) 1.15-1.30 (m, 3H).

Method 67

N-{2-Fluoro-5-[(1Z)-N-hydroxyethanimidoyl]phenyl}acetamide

To a round, bottom flask was added N-(5-acetyl-2-fluorophenyl)acetamide (Method 68, 1.17 g, 6 mmol), hydroxyl amine hydrochloride salt (834 mg, 12 mmol), and NaOAc (1.2 g, 15 mmol) in water:EtOH solution (20 ml, 3:1). The resulting mixture was then set to heat at 50° C. for 1 hour. The reaction was allowed to cool to room temperature and partitioned with EtOAc. The layers were cut and the organic layer was then dried over $Na_2SO_4$, filtered and concentrated in vacuo. The crude residue obtained was then purified by silica gel chromatography (Biotage Horizon System) using a gradient elution of 5-50% EtOAc in DCM to give 815 mg of the title compound (60% overall yield, 2 steps). $^1$H NMR: 11.22 (s, 1H) 9.75 (s, 1H) 8.22 (dd, J=7.54, 1.88 Hz, 1H) 7.30-7.46 (m, 1H) 7.24 (dd, J=10.93, 8.67 Hz, 1H) 1.98-2.18 (m, 6H).

Method 68

N-(5-Acetyl-2-fluorophenyl)acetamide

To a round, bottom flask was added 3-amino-4-fluoroacetophenone (Method 64, 1 g, 6.54 mmol) in DMF (15 ml), followed by the addition of acetyl chloride (0.56 ml, 7.84 mmol) and DIEA (2.3 ml, 13.08 mmol). The solution was set to stir at room temperature. The reaction appeared complete by TLC after 30 min. The reaction was then quenched with water and partitioned with EtOAc. The layers were cut, followed by an additional wash of the aqueous with EtOAc. The combined organic layers were dried over $Na_2SO_4$, filtered and concentrated in vacuo. The crude residue obtained (1.17 g), was used directly in the next step. $^1$H NMR (CDCl$_3$) δ 8.94 (d, J=7.54 Hz, 1H) 7.71 (d, 1H) 7.43 (s, 1H) 7.15 (s, 1H) 2.56-2.60 (m, 3H) 2.21-2.28 (m, 3H).

Method 69

N-[5-(1-Aminoethyl)-2-fluorophenyl]cyclopropanecarboxamide

To a round, bottom flask was added N-{2-fluoro-5-[(1Z)-N-hydroxyethanimidoyl]phenyl}cyclopropanecarboxamide (Method 70, 458 mg, 1.94 mmol) and HOAc (1 ml) in EtOH (25 ml), followed by the addition of Palladium on carbon (100 mg, 10 wt %) under $N_2$ atmosphere. Once the catalyst was added, the system was evacuated and purged with hydrogen (atmospheric pressure). This process was performed several times to ensure complete saturation of hydrogen to the system. The reaction was then allowed to stir for 16 hours at room temperature. The heterogenous mixture was then filtered over a pad of celite and the filtrate was concentrated in vacuo to give quantitative yield of the title compound. $^1$H NMR: 9.99 (s, 1H) 7.85 (d, J=8.29 Hz, 1H) 7.17 (s, J=8.29 Hz, 2H) 4.03 (d, J=6.03 Hz, 1H) 1.90-2.04 (m, 1H) 1.26 (d, J=6.78 Hz, 3H) 0.78 (d, J=6.03 Hz, 4H)

Method 70

N-{2-Fluoro-5-[(1Z)-N-hydroxyethanimidoyl]phenyl}cyclopropanecarboxamide

To a round, bottom flask was added N-(5-acetyl-2-fluorophenyl)cyclopropanecarboxamide (Method 71, 458 mg, 2.07 mmol), hydroxyl amine hydrochloride salt (288 mg, 4.14 mmol), and NaOAc (424 mg, 5.17 mmol) in water-EtOH solution (7 ml, 3:1). The reaction mixture was set to heat at 50° C. for 1 hour. As the reaction reached desired temperature, no dissolution was observed, thus more EtOH (7 ml) was added for dissolution to occur. The reaction was complete after 1 hour and concentrated in vacuo. The title compound (458 mg, 94% yield) was used directly in next step. $^1$H NMR: 11.32 (s, 1H) 10.10 (s, 1H) 8.19 (d, J=6.03 Hz, 1H) 7.30-7.44 (m, 1H) 7.23 (s, 1H) 2.09 (s, 3H) 2.01 (s, 1H) 0.79 (s, 4H).

Method 71

N-(5-Acetyl-2-fluorophenyl)cyclopropanecarboxamide

To a round, bottom flask was added 3-amino-4-fluoroacetophenone (Method 64, 1 g, 6.54 mmol), cyclopropyl carboxylic acid (0.62 ml, 7.84 mmol), HATu (2.5 g (6.57 mmol), and DIEA (2.3 ml, 13.08 mmol) in DMF (15 ml). The reaction mixture was allowed to stir at room temperature for 16 hours. The reaction mixture was quenched with water and partitioned with EtOAc. The layers were cut, followed by an additional wash of the aqueous with EtOAc. The combined organic layers were dried over $Na_2SO_4$, filtered and concentrated in vacuo. The crude residue obtained was then purified by silica gel chromatography (Biotage Horizon System) using a gradient elution of 5-15% EtOAc in DCM to give 458 mg of the title compound (32% isolated yield). $^1$H NMR: 10.16 (s, 1H) 8.53 (dd, J=7.91, 2.26 Hz, 1H) 7.67-7.82 (m, 1H) 7.40 (dd, J=10.55, 8.67 Hz, 1H) 2.54 (s, 3H) 1.95-2.09 (m, 1H) 0.78-0.88 (m, 4H).

Method 72

1-(5-Fluoro-pyrimidin-2-yl)ethanamine

A round-bottom flask containing 2-(1-azidoethyl)-5-fluoropyrimidine (Method 73, 0.60 g, 3.59 mmol) was charged with 10% Pd/C (0.191 g) and was evacuated and backfilled with $H_2$ via a filled balloon. MeOH (10 ml) was added, and the mixture was allowed to stir at room temperature for 3 hours. The mixture was filtered through a plug of diatomaceous earth, which was subsequently washed well with MeOH. The filtrates were concentrated to give the title compound as a pale yellow oil (0.50 g, 99%). $^1$H NMR (CDCl$_3$) δ 8.60 (s, 2H), 4.65 (br s 2H), 4.10 (m, 1H), 1.20 (d, 3H).

Method 73

2-(1-Azidoethyl)-5-fluoropyrimidine

A round-bottom flask containing 1-(5-fluoropyrimidin-2-yl)ethanol (Method 74, 0.79 g, 5.55 mmol) was charged with triethylamine (0.67 g, 6.66 mmol) and anhydrous DCM (10 ml). The solution was cooled to 0° C., and methanesulfonyl chloride (0.70 g, 4.1 mmol) was added dropwise. The resulting mixture was allowed to stir at room temperature for 2 hours, at which point the volatile components were removed using a rotary evaporator. The residue was dissolved in DMF (15 ml) and treated with sodium azide (0.72 g, 11.1 mmol).

The resulting mixture was stirred at room temperature for 60 hours. It was then partitioned between EtOAc and brine. The organic layer was obtained, dried ($Na_2SO_4$), and evaporated to dryness. The crude material was purified by silica gel chromatography (by ISCO Combiflash with gradient EtOAc and hexanes) to afford the title compound as a colourless oil (0.60 g, 65% yield over two steps). GC-MS, 167 (M), 138 (M-$N_2$), 125 (M-$N_3$); $^1$H NMR (CDCl$_3$) δ 8.60 (s, 2H), 4.60 (m, 1H), 1.65 (d, 3H).

Method 74

1-(5-Fluoropyrimidin-2-yl)ethanol 1-(5-Fluoropyrimidin-2-yl)ethanone (Method 75, 0.77 g) was dissolved in MeOH (15 ml), and the solution was cooled to 0° C. NaBH$_4$ (0.210 g, 5.55 mmol) was added. The mixture was stirred at room temperature for 1 hour and then partitioned between EtOAc and H$_2$O. The organic extract was washed with brine, dried ($Na_2SO_4$), filtered, and concentrated to give the title compound as a yellowish oil (0.79 g, 99%). $^1$H NMR (CDCl$_3$) δ 8.65 (s, 2H), 5.20 (m, 1H), 4.00 (br s, 1H), 1.80 (d, 3H).

Method 75

1-(5-Fluoropyrimidin-2-yl)ethanone

A round-bottom-flask containing 5-fluoropyrimidine-2-carbonitrile (Method 59, 1.50 g, 12.19 mmol) was charged with anhydrous THF (30 ml) under $N_2$. The solution was cooled to 0° C., and a solution of MeMgBr (4.90 ml of a 3.0 M solution in ether, 14.62 mmol) was added dropwise. After 2 hours at 0° C., the reaction mixture was quenched with ice water and extracted with EtOAc. The organic extract was washed with brine, dried over $Na_2SO_4$, and evaporated to dryness to give the title compound as an oil (0.778 g, yield 46%). GC-MS, 140 (M); $^1$H NMR (CDCl$_3$) δ 8.65 (s, 2H), 2.65 (s, 2H).

Method 76

1-(6-Fluoro-pyridin-3-yl)ethanamine

To a slurry of Raney Nickel in EtOH solution (75 ml), under inert atmosphere, was added 1-(6-fluoropyridin-3-yl)ethanone oxime (Method 77, 2.3 g, 14.9 mmol). The system was purged with hydrogen and evacuated several times to ensure complete saturation with hydrogen. The reaction, after 2 hours stirring at room temperature, was filtered over celite and filtrate collected was concentrated in vacuo to give 2 g (95% isolated yield) of the title compound. $^1$H NMR: 8.16 (s, 1H) 7.97 (t, J=8.29 Hz, 1H) 7.09 (dd, J=8.29, 3.01 Hz, 1H) 4.03 (q, J=6.78 Hz, 1H) 1.23 (d, J=6.03 Hz, 3H).

Method 77

1-(6-Fluoropyridin-3-yl)ethanone oxime

To a 200-ml, round bottom flask was added, 1-(6-fluoro-pyridin-3-yl)ethanone (Method 65, 2.5 g, 17.9 mmol), hydroxylamine hydrochloride (2.5 g, 35.8 mmol), and NaOAc (3.7 g, 44.8 mmol) in a solution of water-EtOH (65 ml, 3.3:1). The resulting mixture was heated to 50° C. for 1 hour. The reaction was then allowed to cool to room temperature, partitioned with EtOAc, layers were cut, and organic layer was dried over $Na_2SO_4$, filtered, and concentrated in vacuo to afford the title compound in quantitative yield. $^1$H NMR: 11.49 (s, 1H) 8.47 (s, 1H) 8.17-8.27 (m, 1H) 7.21 (dd, J=8.29, 3.01 Hz, 1H) 2.17 (s, 3H).

Method 78 tert-Butyl 5-amino-3-isopropoxy-1H-pyrazole-1-carboxylate

A solution of 5-isopropoxy-1H-pyrazol-3-amine (3.5 g, 24.8 mmol) in DCM (100 ml) was prepared at room temperature. A 4.5M aqueous KOH solution (11.1 g, 198 mmol) was added dropwise, followed by the addition of di-tert-butyl dicarbonate (5.68 g, 26 mmol) in DCM (20 ml). The resulting reaction was then stirred vigorously for 30 hours, at which point water (200 ml) was added and the layers were allowed to separate. The organic fraction was separated, dried ($Na_2SO_4$), filtered, and then concentrated. The resulting oil was purified by column chromatography (100:1 DCM: MeOH) to give the title compound (5.4 g, 90%). MS: Calcd.: 241. Found: [M+H]$^+$ 242.

Method 79 tert-Butyl 5-(5-cyano-3,6-difluoropyridin-2-ylamino)-3-isopropoxy-1H-pyrazole-1-carboxylate A solution of tert-butyl 5-amino-3-isopropoxy-1H-pyrazole-1-carboxylate (Method 78, 4.0 g, 16.4 mmol) in THF (45 ml) was cooled to −78° C. A 1.0M THF solution of LiHMDS (2.61 g, 15.6 mmol) was added dropwise and the reaction was stirred at −78° C. for 30 minutes. A −78° C. solution of 2,5,6-trifluoronicotinonitrile (1.3 g, 8.2 mmol) in THF (20 ml) was added dropwise via cannula to the above anion solution. Upon completion of the addition, the resulting reaction was allowed to stir for 10 minutes at −78° C., and was then quenched with water (100 ml). The reaction was allowed to warm to room temperature, extracted with DCM (3×100 ml), dried ($Na_2SO_4$), filtered, and then concentrated to give the title compound (95% conversion by LCMS) which was used without further purification. MS: Calcd.: 379. Found: [M+H]$^+$ 380.

Utility

The compounds of the present invention have utility for the treatment of cancer by inhibiting the tyrosine kinases, particularly the Trks and more particularly Trk A and B. Methods of treatment target tyrosine kinase activity, particularly the Trk activity and more particularly Trk A and B activity, which is involved in a variety of cancer related processes. Thus, inhibitors of tyrosine kinase, particularly the Trks and more particularly Trk A and B, are expected to be active against neoplastic disease such as carcinoma of the breast, ovary, lung, colon, prostate or other tissues, as well as leukemias and lymphomas, tumours of the central and peripheral nervous system, and other tumour types such as melanoma, fibrosarcoma and osteosarcoma. Tyrosine kinase inhibitors, particularly the Trk inhibitors and more particularly Trk A and B inhibitors are also expected to be useful for the treatment other proliferative diseases including but not limited to autoimmune, inflammatory, neurological, and cardiovascular diseases.

In addition, the compounds of the invention are expected to be of value in the treatment or prophylaxis of cancers selected with up regulated of constitutively activated Trk kinases, including but not limited to, oncogenic rearrangements leading to ETV6-TrkC fusions, TRP-TrkA fusions proteins, AML-ETO (t8; 21), autocrine or paracrine signalling leading to elevated serum levels of NGF, BDNF, neurotropins or tumours with constitutively active Trk associated with disease aggressiveness, tumour growth and proliferation or survival signalling.

Compounds of the present invention have been shown to inhibit tyrosine kinases, particularly the Trks and more particularly Trk A and B, as determined by the Trk A Assay described herein.

Compounds provided by this invention should also be useful as standards and reagents in determining the ability of a potential pharmaceutical to inhibit tyrosine kinases, particularly the Trks and more particularly Trk A and B. These would be provided in commercial kits comprising a compound of this invention Trk A Assay Format Trk A kinase activity was measured for its ability to phosphorylate synthetic tyrosine residues within a generic polypeptide substrate using an Amplified Luminescent Proximity Assay (Alphascreen) technology (PerkinElmer, 549 Albany Street, Boston, Mass.).

To measure Trk A kinase activity, the intracellular domain of a HIS-tagged human Trk A kinase (amino acids 442-796 of Trk A, Swiss-Prot Primary Accession Number P04629) was expressed in SF9 cells and purified using standard nickel column chromatography. After incubation of the kinase with a biotinylated substrate and adenosine triphosphate (ATP) for 20 minutes at room temperature, the kinase reaction was stopped by the addition of 30 mM ethylenediaminetetraacetic acid (EDTA). The reaction was performed in 384 well microtitre plates and the reaction products were detected with the addition of strepavidin coated Donor Beads and phosphotyrosine-specific antibodies coated Acceptor Beads using the EnVision Multilabel Plate Reader after an overnight incubation at room temperature.

| | |
|---|---|
| Peptide substrate | PolyEY-biotin (PGT-bio.) |
| ATP Km | 70 μM |
| Assay conditions | 0.838 ng/ml Trk A, 9 mM HEPES, 45 μg/ml BSA, 10 mM MnCl$_2$, 5 nM PGT-bio, 0.01% Triton ® X-100, 70 μM ATP |
| Incubation | 20 minutes, room temperature |
| Termination/Detection conditions | 6.3 mM HEPES, 30 mM EDTA, 525 μg/ml BSA, 40 mM NaCl, 0.007% Triton ® X-100, 12 ng/ml of Donor Beads, 12 ng/ml of Acceptor Beads |
| Detection incubation | overnight, room temperature |
| Fluometer settings | Excitation = 680 nM Emission = 570 nM Excitation Time = 180 ms Total Measurement Time = 550 ms |

Although the pharmacological properties of the compounds of the formula (I) vary with structural change, in general activity possessed by compounds of the formula (I) may be demonstrated at IC$_{50}$ concentrations (concentrations to achieve 50% inhibition) or doses in the range of (0.01 μM to 10 μM).

When tested in the above in-vitro assay the Trk inhibitory activity of the following examples was measured at the following IC$_{50}$s.

| Ex | IC$_{50}$ (μM) |
|---|---|
| 21 | 0.611 |
| 24 | 0.109 |
| 47 | 0.063 |

The invention claimed is:

1. (S)-5-Fluoro-2-(1-(5-fluoropyridin-2-yl)ethylamino)-6-(5-isopropoxy-1H-pyrazol-3-ylamino)nicotinonitrile, or a pharmaceutically acceptable salt thereof.

2. A method of inhibiting Trk activity comprising administering to a host in need of such treatment a therapeutically effective amount of (S)-5-fluoro-2-(1-(5-fluoropyridin-2-yl)ethylamino)-6-(5-isopropoxylH-pyrazol-3-ylamino)nicotinonitrile, or a pharmaceutically acceptable salt thereof.

3. A pharmaceutical composition comprising (S)-5-fluoro-2-(1-(5-fluoropyridin-2-yl)ethylamino)-6-(5-isopropoxylH-pyrazol-3-ylamino)nicotinonitrile, or a pharmaceutically acceptable salt thereof, together with at least one pharmaceutically acceptable carrier, diluent or excipient.

* * * * *